United States Patent [19]
Kiely et al.

[11] Patent Number: 5,874,443
[45] Date of Patent: Feb. 23, 1999

[54] ISOQUINOLINE DERIVATIVES AND ISOQUINOLINE COMBINATORIAL LIBRARIES

[75] Inventors: John S. Kiely; Michael C. Griffith, both of San Diego, Calif.

[73] Assignee: Trega Biosciences, Inc., San Diego, Calif.

[21] Appl. No.: 734,516

[22] Filed: Oct. 18, 1996

Related U.S. Application Data

[60] Provisional application No. 60/037,974, Oct. 19, 1995.
[51] Int. Cl.$^6$ .......................... C07D 217/02; A61K 31/47
[52] U.S. Cl. ............................................. 514/309; 546/141
[58] Field of Search .............................. 546/141; 514/309

[56] References Cited

U.S. PATENT DOCUMENTS

| | | | |
|---|---|---|---|
| 5,010,175 | 4/1991 | Rutter et al. ............................. | 530/334 |
| 5,182,366 | 1/1993 | Huebner et al. ......................... | 530/334 |
| 5,288,514 | 2/1994 | Ellman ........................................ | 427/2 |
| 5,324,483 | 6/1994 | Cody et al. .............................. | 422/131 |

FOREIGN PATENT DOCUMENTS

| | | |
|---|---|---|
| 0 590 455 | 9/1993 | European Pat. Off. . |
| WO 94/01102 | 1/1994 | WIPO . |
| WO 95/02566 | 1/1995 | WIPO . |
| WO 95/04277 | 2/1995 | WIPO . |

OTHER PUBLICATIONS

Gordon et al., "Application of combinatorial technologies to drug discovery. 2. Combinatorial organic synthesis, library screening strategies, and future directions." *J. of Med. Chem.*, 37(10):1386–1401 (1994).

Gallop et al., "Applications of combinatorial technologies to drug discovery. 1. Background and peptide combinatorial libraries." *J. of Med. Chem.*, 37(9):1233–1251 (1994).

Houghten et al., "Generation and use of synthetic peptide combinatorial libraries for basic research and drug discovery." *Nature*, 354:94–96 (1991).

Goff and Zuckerman, "Solid–phase synthesis of highly substituted peptide 1(2H)–Isoquinolinones," *J. Org. Chem.*, 60:5748–5749 (Sep. 8, 1995).

Ostresh et al., "Libraries from libraries: Chemical transformation of combinatorial libraries to extend the range and repertoire of chemical diversity." *Proc. Natl. Acad. Sci. USA*, 9:11138–11142 (1994).

Smith and Atigada, "Condensation of homophthalic anhydrides with heterocyclic imines and DMAD under mild conditions." *J. Heterocyclic Chem.*, 28:1813–1815 (1991).

Cushman and Castagnoli, "The Synthesis of trans–3–methylnicotine." *J. Org. Chem.*, 37(8):1268–1271 (1972).

Cushman and Castagnoli, "Synthesis of pharmacologically active nitrogen analogs of the tetrahydrocannabinols." *J. Org. Chem.*, 39(11):1546–1550 (1974).

Cushman and Castagnoli, "The condensation of succinic anhydrides with schiff bases. Scope and mechanism." *J. Org. Chem.*, 36(22):3404–3406 (1971).

Castagnoli, "The condensation of succinic anhydride with benzylidinemethylamine. A stereoselective synthesis of trans–and
cis–1–Methyl–4–carboxy–5–phenyl–2–pyrrolidinone."*J. of Org. Chem.*, 34(10):3187–3189 (1969).

Cushman and Madaj, "A study and mechanistic interpretation of the electronic and steric effects that determine the stereochemical outcome of the reaction of schiff bases with homophthalic anhydride and a 3–phenylsuccinic anhydride." *J. Org. Chem.*, 52(5):907–914 (1987).

Cushman and Castagnoli, "A novel approach to the synthesis of nitrogen analogs of the tetrahydrocannabinols." *J. Org. Chem.*, 38(3):440–448 (1973).

Tamura et al., "Cycloaddition of homophthalic anhydride: A new and simple route to linearly condensed phenolic compounds," *Tetrahedron Letters*, 22(43):4283–4286 (1981).

Wenker, Henry, "Syntheses from ethanolamine. V. Synthesis of $\Delta$–Oxazoline and of 2,2'–$\Delta^2$–Di–oxazoline." *J. of Am. Chem. Society*, 60(8):2152–2153 (1938).

Smith et al., "Synthetic approaches to hexahydropyrrolo[1, 2–b]isoquinolones." *J. Heterocyclic Chem.*, 26:1815–1817 (1989).

Coppola, Gary, "Novel heterocycles. 8. Fused isoquinolines derived from the reaction of homophthalic anhydride with cyclic imino ethers." *J. Heterocyclic Chem.*, 18:767–770 (1981).

Haimova et al., "A highly stereoselective synthesis of 3,4–dihydro–1(2H)–isoquinolinones and 8–oxoberbines from homophthalic anhydrides and azomethines." *Tetrahedron*, 33:331–336 (1977).

Tamura et al., "Strong base induced cycloaddition of homophthalic anhydrides leading to peri–hydroxy polycyclic compounds." *J. Org. Chem.*, 49:473–478 (1984).

Lee et al., "Cycloaddition of Homophthalic Anhydrides to Azodicarboxylate and Alkylidenecarbamates." *Chemical Abstracts*, 106(3):18331a (1987).

*Primary Examiner*—Zinna Northington-Davis
*Attorney, Agent, or Firm*—Campbell & Flores LLP

[57] ABSTRACT

The present invention provides the synthesis of heterocyclic compounds based on the isoquinoline ring. More specifically, the invention provides novel isoquinolines as well as novel libraries comprised of many such compounds, and methods of synthesizing the libraries.

12 Claims, No Drawings

ISOQUINOLINE DERIVATIVES AND ISOQUINOLINE COMBINATORIAL LIBRARIES

This application is a based on Provisional Application Ser. No. 60/037,974 filed Oct. 19, 1995 now pending.

BACKGROUND OF THE INVENTION

1. Field of the Invention

The present invention relates generally to the synthesis of heterocyclic compounds based on the isoquinoline ring. More specifically, the invention provides novel isoquinolines as well as novel libraries comprised of many such compounds, and methods of synthesizing the libraries.

2. Background Information

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as isoquinolines.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide.

Combinatorial chemical methods have been applied to a limited number of heterocyclic compounds, as described, for example, in U.S. Pat. No. 5,288,514 to Ellman, U.S. Pat. No. 5,324,483 to Cody et al. and Goff and Zuckermann, *J. Org. Chem.*, 60:5748–5749 (1995). However, the heterocyclic libraries to date contain compounds of limited diversity and complexity. For example, the isoquinolines prepared by the methods of Goff and Zuckermann are limited, due to steric hindrance in the ringforming reactions utilized with respect to the types of substituents which can be incorporated onto the isoquinoline ring. The reactions utilized by Goff and Zuckermann were easily hindered by the steric bulk of the substituents to be added to the compounds, thus limiting the complexity of the resulting library of isoquinolines. Moreover, with heterocyclic combinatorial libraries to date, only a small number of compounds can be prepared in a given library.

Substituent limitations have been overcome for mixtures of peptides and peptidomimetics through the use of solid phase techniques versus solution-phase. An important step in the development of solid-phase techniques was the discovery of methods to identify active individual compounds from soluble mixtures of large numbers of compounds, as described, for example, by Rutter in U.S. Pat. No. 5,010,175 and Simon in WO PCT 91/19735. These soluble mixture methods, however, have rarely been applied to the syntheses of complex heterocyclic structures. There exists a need to develop more complex "organic" libraries based on heterocyclic medicinal compounds which would require less time and effort in the synthesis and testing needed to bring an organic pharmaceutical product to fruition. In short, improved methods for generating therapeutically useful heterocyclic compounds, such as isoquinoline derivatives, are desired.

This invention satisfies these needs and provides related advantages as well. The present invention overcomes the known limitations to classical organic synthesis of isoquinolines as well as the shortcomings of combinatorial chemistry with heterocycles. The present invention combines the techniques of solid-phase synthesis of heterocycles and the general techniques of synthesis of combinatorial libraries to prepare new isoquinoline compounds.

SUMMARY OF THE INVENTION

The present invention relates to novel isoquinoline compounds of the following formula, libraries containing such compounds, and to the generation of such combinatorial libraries composed of such compounds:

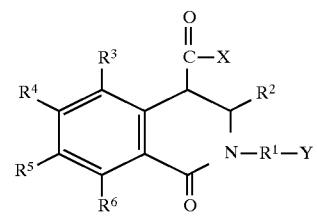

FORMULA I wherein $R^1$, $R^2$, $R^3$, $R^4$, $R^5$, $R^6$, X and Y have the meanings provided below.

DETAILED DESCRIPTION OF THE INVENTION

The present invention provides novel derivatives and libraries of novel derivatives of variously substituted isoquinoline compounds of Formula I:

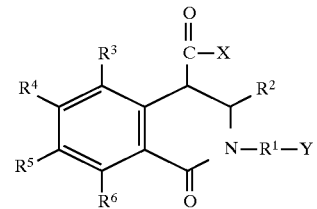

FORMULA I

In the above Formula I:

$R^1$ is $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, phenyl, substituted phenyl, substituted naphthyl, $C_7$ to $C_{12}$ phenylalkyl, $C_7$ to $C_{12}$ substituted phenylalkyl or a group of the formula:

wherein n and m are independently selected from a number 0 to 6; and Ar is an aryl group selected from the group consisting of phenyl, substituted phenyl, heteroaryl or substituted heteroaryl;

$R^2$ is hydrogen atom, $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, phenyl, substituted phenyl, naphthyl, substituted naphthyl, $C_3$ to $C_7$ cycloalkyl, $C_3$ to $C_7$ substituted cycloalkyl, $C_7$ to $C_{12}$ phenylalkyl, $C_5$ to $C_7$ cylcoalkenyl, $C_5$ to $C_7$ substituted cycloalkenyl, $C_7$ to $C_{12}$ substituted phenylalkyl or a heterocyclic ring;

$R^3$ $R^4$, $R^5$ and $R^6$ are, independently, a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ alkylsulfonyl, $C_1$ to $C_4$ alkylsulfoxide, phenylthio, substituted phenylthio, phenylsulfoxide, substituted phenylsulfoxide, phenylsulfonyl or substituted phenylsulfonyl;

X is hydroxy, protected carboxy, amino, protected amino, (monosubstituted)amino, (disubstituted)amino, an amino acid, aniline, substituted aniline or an amino-substituted heterocyclic ring; and Y is $CO_2H$, SH, $NHR^7$ or $C(O)$ $NHR^7$, wherein $R^7$ is a hydrogen atom, $C_1$ to $C_6$ alkyl or $C_1$ to $C_6$ substituted alkyl.

For $R^1$ defined above, n and m are independently selected from a number 0 to 6. Preferably, n and m are independently selected from 0 to 4 and, more preferably, from 0 to 3.

In one embodiment of the above isoquinoline compounds, $R^1$, $R^2$, $R^3$, $R^4$, $R^5$, $R^6$, $R^7$, X and Y are as defined above, with the exception that $R^2$ is other than a hydrogen atom and, therefore, $R^2$ is $C_1$ to $C_6$ alkyl, $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, phenyl, substituted phenyl, naphthyl, substituted naphthyl, $C_3$ to $C_7$ cycloalkyl, $C_3$ to $C_7$ substituted cycloalkyl, $C_1$ to $C_7$ cylcoalkenyl, $C_5$ to $C_7$ substituted cycloalkenyl, $C_7$ to $C_{12}$ phenylalkyl, $C_7$ to $C_{12}$ substituted phenylalkyl or a heterocyclic ring.

Also, another embodiment is where $R^1$, $R^2$, $R^3$, $R^4$, $R^5$, $R^6$, $R^7$, X and Y are as defined for Formula I or as defined by any of the above-preferred embodiments, with the exception that $R^5$ is other than $C_1$ to $C_7$ alkoxy and, more preferably, is not methoxy, and even more preferably, when $R^2$ is a hydrogen atom, $R^5$ is other than $C_1$ to $C_7$ alkoxy.

In yet a further embodiment of the present invention, $R^1$, $R^2$, $R^3$, $R^4$, $R^5$, $R_6$, $R^7$, X and Y are as defined for Formula I, with the exception that X is not amino or protected amino and is, therefore, hydroxy, protected carboxy, (monosubstituted)amino, (disubstituted)amino, an amino acid, aniline, substituted aniline or an amino-substituted heterocyclic ring.

Another embodiment of the invention is where $R^1$, $R^3$, $R^4$, $R^5$, $R^6$, $R^7$, X and Y are as defined above and $R^2$ is other than hydrogen or $C_1$ to $C_6$ alkyl and is, therefore:

$R^2$ is $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, phenyl, substituted phenyl, naphthyl, substituted naphthyl, $C_3$ to $C_7$ cycloalkyl, $C_3$ to $C_7$ substituted cycloalkyl, $C_5$ to $C_7$ cylcoalkenyl, $C_5$ to $C_7$ substituted cycloalkenyl, $C_7$ to $C_{12}$ phenylalkyl, $C_7$ to $C_{12}$ substituted phenylalkyl or a heterocyclic ring.

Another embodiment of the invention is where $R^1$, $R^3$, $R^4$, $R^5$, $R^6$, $R^7$ and Y are as defined above and $R^2$ is other than hydrogen or $C_1$ to $C_6$ alkyl and is, therefore:

$R^2$ is $C_1$ to $C_6$ substituted alkyl, $C_2$ to $C_7$ alkenyl, $C_2$ to $C_7$ substituted alkenyl, $C_2$ to $C_7$ alkynyl, $C_2$ to $C_7$ substituted alkynyl, phenyl, substituted phenyl, naphthyl, substituted naphthyl, $C_3$ to $C_7$ cycloalkyl, $C_3$ to $C_7$ substituted cycloalkyl, $C_5$ to $C_7$ cylcoalkenyl, $C_5$ to $C_7$ substituted cycloalkenyl, $C_7$ to $C_{12}$ phenylalkyl, $C_7$ to $C_{12}$ substituted phenylalkyl or a heterocyclic ring; and X is hydroxy, protected carboxy, (monosubstituted) amino, (disubstituted) amino, an amino acid, aniline, substituted aniline or an amino-substituted heterocyclic ring.

In yet another embodiment of the invention, the isoquinoline compounds have $R^1$, $R^2$, $R^3$, $R^4$, $R^5$, $R_6$, $R^7$, X and Y as defined above following Formula I, or as defined in any of the above preferred embodiments, with the proviso that X is not a guanidinium group or, alternatively, with the proviso that when X is an amino acid it is other than the amino acid Lys, Arg, or a functional equivalent thereof containing a guanidium group.

In a preferred embodiment of this invention, the isoquinoline compounds are wherein:

$R^1$ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2-ethyl),

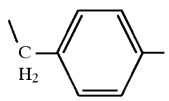

and

and, more preferably is 1,6-hexyl;

$R^2$ is selected from the group consisting of 1,4-benzodioxan-6-yl, 1-methylindol-3-yl, 2,3-difluorophenyl, 2-bromophenyl, 2-chloro-5- nitrophenyl, 2-furyl, 2-imidazolyl, 2-naphthyl, 2-pyridinyl, 2-thiophenyl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophenyl, 4-(3-dimethylaminoprop-1-oxy)phenyl, 4-(dimethylamino)phenyl, 4-(methylthio)phenyl, 4-(trifluoromethyl)phenyl, 4-biphenyl, 4-bromo-2-thiophenyl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl, and, more preferably is 5-(4'-methoxybenzyl)-furan-2-yl;

$R^3$, $R^4$, $R^5$, $R^6$ are independently a hydrogen atom;

X is selected from the group consisting of aminocyclopropyl, aminoisopropyl, 3-aminopropyl, aminoethanolyl, (aminomethyl)cyclopropyl, pyrrolidilyl, aminodiethyl, amino-2-methoxyethyl, aminocyclopentyl, piperidinyl, 1-(pyrrolidin-3-ol), aminoamyl, amino-(2-(N,N-dimethyl))ethyl, azetidinyl, aminofurfuryl, aminodiallyl, 2-aminothiazolyl, 1-aminopiperidinyl, 1-methylpiperazinyl, 4-aminomorpholinyl, aminodiethanol, 2-(aminomethyl)pyridinyl, histaminyl, 1-(2-aminoethyl)pyrrolidinyl, (+)-3-hydroxy piperidine, (s)-1-amino-2-(methoxymethyl)pyrrolidine, 1-amino-4-methylpiperazinyl, tris(hydroxymethyl)aminomethyl, 1-aminopyrrolidinyl, 1-(3-aminopropyl)imidazolyl, 1-(2-hydroxyethyl)piperazinyl, trans-aminocyclohexan-2-olyl, tryptaminyl, 1-aminomethyladamantanyl, amino-2-(trimethylammonium)ethyl chloride, α-N-glycinyl, α-N-lysinyl, α-N-aspartyl, α-N-tyrosinyl, α-N-serinyl, (+)-3-aminopropyl-1,2-diol, (−)-3-amino-propyl-1,2-diol, (+)-aminotetrahydrofurfuryl, (−)-aminotetrahydrofurfuryl, (+)-exo-2-aminonorbornanyl, (−)-exo-2-aminonorbornanyl, cis-decahydroquinolinyl, trans-decahydroquinolinyl, (+)-3-aminoquinuclidinyl and (−)-3-aminoquinuclidinyl and, more preferably, is 1-aminomethyladamantanyl or (aminomethyl)cyclohexyl; and Y is $C(O)NH_2$.

In yet another preferred embodiment, $R^1$ is selected from the group consisting of methylene, 1,2-ethyl, 1,4-butyl, 1,6-hexyl, (s)-1-(amino)-1,-ethyl, (s)-1-(amino)-1,5-pentyl, (r)-(1-methyl)-1,2-ethyl, (s)-(1-(methyl)-1,2-ethyl),

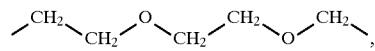

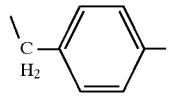

and

$R^2$ is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophenyl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophenyl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophenyl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

$R^3$, $R^4$, $R^5$, $R^6$ are independently a hydrogen atom;

X is selected from the group consisting of anilinyl, 2-fluoroanilinyl, 3-fluoroanilinyl, 4-fluoroanilinyl, 2-chloroanilinyl, 3-chloroanilinyl, 4-chloroanilinyl, 2-bromoanilinyl, 3-bromoanilinyl, 4-bromoanilinyl, 2-methoxyanilinyl, 3-methoxyanilinyl, 4-methoxyanilinyl, 2-hydroxyanilinyl, 3-hydroxyanilinyl, 4-hydroxyanilinyl, 2-carboethoxyanilinyl, 3-carboethoxyanilinyl, 4-carboethoxyanilinyl, 2-trifluoromethylanilinyl, 3-trifluoromethylanilinyl, 4-trifluoromethylanilinyl, 2-dimethylaminoanilinyl, 3-dimethylaminoanilinyl, 4-dimethylaminoanilinyl, 2-phenoxyanilinyl, 3-phenoxyanilinyl, 4-phenoxyanilinyl, 3,4-methylenedioxyanilinyl, 2,3-methylenedioxyanilinyl, 2,3-difluoroanilinyl, 2,3-dibromoanilinyl, 3,4-dibromoanilinyl, 2,3-dimethoxyanilinyl, 3,4-dimethoxyanilinyl, 1-amino-5,6,7,8-tetrahydronaphthyl, 2-hydroxy-3-amino-5,6,7,8-tetrahydronaphthyl, 2-aminonaphthyl, 1-amino-4-chloronaphthyl, 1-amino-4-bromonaphthyl, 5-amino-1-hydroxynaphthyl, 1-amino-2-hydroxynaphthyl, 5-aminoindanyl, 1-aminofluorenyl, 2-aminofluorenyl and N-methylanilinyl; and Y is $C(O)NH_2$.

In yet another preferred embodiment, $R^1$ is selected from the group consisting of methylene, 1,2-ethyl, 1,3-propyl, 1,4-butyl, 1,5-pentyl, 1,6-hexyl, (S)-1-amino-1,2-ethyl, (S)-1-amino-1,5-pentyl, (R)-1-methyl-1,2-ethyl, (S)-1-methyl-1,2-ethyl,

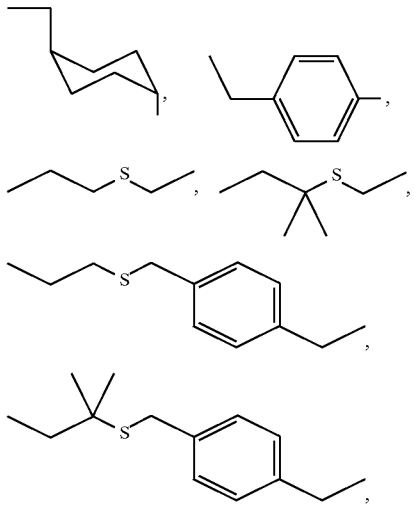

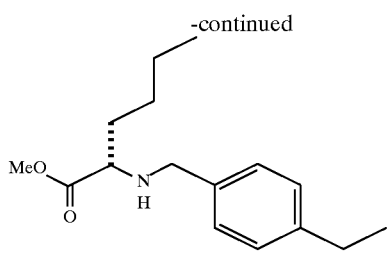

$R^2$ is selected from the group consisting of phenyl, 2-bromophenyl, 2-cyanophenyl, 2-fluorophenyl, 2-hydroxyphenyl, 2-methoxyphenyl, 3-bromophenyl, 3-carboxyphenyl, 3-cyanophenyl, 3-fluorophenyl, 3-hydroxyphenyl, 3-methoxyphenyl, 3-methylphenyl, 3-nitrophenyl, 3-(trifluoromethyl)phenyl, 4-acetamidophenyl, 4-bromophenyl, 4-carboxyphenyl, 4-cyanophenyl, 4-(3-dimethylaminopropoxy)phenyl, 4-fluorophenyl, 4-(dimethylamino)phenyl, 4-hydroxyphenyl, 4-isopropylphenyl, 4-methoxyphenyl, 4-methylphenyl, 4-(methylcarboxylate)phenyl, 4-methylsulphonylphenyl, 4-(methylthio)phenyl, 4-nitrophenyl, 4-propoxyphenyl, 4-(trifluoromethyl)phenyl, 3,5-bis(trifluoromethyl)phenyl, 3,5-dimethoxyphenyl, 3,5-dihydroxyphenyl, 3,5-dichlorophenyl, 2,3-difluorophenyl, 2,4-dichlorophenyl, 2-chloro-5-nitrophenyl, 2-chloro-6-fluorophenyl, 2,6-difluorophenyl, 3-bromo-4-fluorophenyl, 3,4-dihydroxyphenyl, 3,4-dichlorophenyl, 3,4-difluorophenyl, 3-fluoro-4-methoxyphenyl, 3-nitro-4-chlorophenyl, 3-hydroxy-4-methoxyphenyl, 3-hydroxy-4-nitrophenyl, 4-methoxy-3-(sulfonyl)phenyl, 3-methyl-4-methoxyphenyl, 2,3,4-trifluorophenyl, 2,3,5-trichlorophenyl, 3,5-dimethyl-4-hydroxyphenyl, 3-methoxy-4-hydroxy-5-bromophenyl, 3-methoxy-4-hydroxy-5-nitrophenyl, 1,4-benzodioxan-6-yl, 2,3-(methylenedioxy)phenyl, 3,4-(methylenedioxy)phenyl, 3,4-(methylenedioxy)-6-nitrophenyl, 8-hydroxyjulolidin-9-yl, 3-(3,4-dichlorophenoxy)phenyl, 3-(4-methoxyphenoxy)phenyl, 3-phenoxyphenyl, 4-phenoxyphenyl, 4-biphenyl, 1-naphthyl, 2-naphthyl, 4-methoxy-1-naphthyl, 2-quinolinyl, 3-quinolinyl, 4-quinolinyl, 8-hydroxyquinoline-2-yl, 9-ethyl-3-carbazolyl, 2-thiophenyl, 3-thiophenyl, 5-methyl-2-thiophenyl, 2-furyl, 3-furyl, 5-methylfur-2-yl, 2-pyridinyl, 3-pyridinyl, 4-pyridinyl, 6-methyl-2-pyridinyl, pyrrol-2-yl, 1-methyl-2-pyrrolyl, 2-imidazolyl, 2-thiazolyl, 5-(4'-methoxybenzyl)-2-fur-2-yl, and 5-nitro-2-fur-2-yl;

$R^3$, $R^4$, $R^5$, $R^6$ are independently a hydrogen atom;

X is selected from the group consisting of pyridoxamino, 4-(dimethylamino)benzylamino, 2-chloro-4-fluoroanilino, 3-pyridylmethylamino, 4-(dimethylamino)anilino, 1-adamantanemethylamino, 4-isopropylanilino, 3,4-dichlorobenzylamino, N-benzylethanolamino, 4-(α,α,60-trifluoro-m-tolyl)piperazino, 4-nitrobenzylamino, 5-indanylamino, cyclohexylamino, 4-(2-pyridyl)piperazino, 4-methoxyphenethylamino, 1-naphthalenemethylamino, 2,4-dimethoxybenzylamino, (±)-exo-2-norbornaneamino, 2-(2-chlorophenyl)ethylamino, 2-(4-methoxyphenyl)-2-phenylethylamino, 1,4-benzodioxan-6-amino, 5-bromo-2-fluorobenzylamino, 4-pyridylmethylamino, 4-phenylpiperazino, 2-fluoreneamino, 3,4-dimethoxybenzylamino, 2-(4-chlorophenyl)ethylamino, diphenylmethylamino, phenethylamino, N-benzylmethylamino, 4-iodoanilino, 3-nitrobenzylamino (±)-endo-2-norbornaneamino, 2-(3-chlorophenyl)ethylamino, 3-phenyl-1-propylamino, 3,5-dimethylanilino, 1,2,3,4-tetrahydroisoquinolino, 1,3,3-trimethyl-6-azabicyclo[3.2.1]octyl, 2-chloro-5-methylanilino, 3-chloro-4-methoxyanilino, 4-(4-methoxyphenyl)-4-phenylpiperidino, 5-fluoro-2-methylanilino, 4-phenoxyanilino, tryptamino, cycloheptylamino, 2,4-difluorobenzylamino, 2-fluoro-5-methylanilino, 3,4-difluorobenzylamino, 1-methyl-3-phenylpropylamino, 2,4-dichlorophenethylamino, 2-indanamino, 3,4,5-trimethoxybenzylamino, 2-bromobenzylamino, 2-bromo-4-methylanilino, trans-2-phenylcyclopropylamino, 3-amino-2,6-dimethoxypyridino, 5-chloro-2-methoxyanilino, 2-iodoanilino, 2,3-dimethoxybenzylamino, 2,6-difluorobenzylamino, 2,4-dimethoxyanilino, 4-chloro-2-methoxy-5-methylanilino, 1-amino-4-bromonaphthalene, 3-trifluoromethylbenzylamino, 3-chloro-2-methylanilino, 3-carboxamidoanilino, 2-fluorophenethylamino, 3-bromobenzylamino, 3-iodoanilino, 3-phenoxyanilino, 3,4-dimethoxyphenethylamino, 4-morpholinoanilino, 2-ethoxyanilino, tyramino, 2-trifluoromethylbenzylamino, 4-bromobenzylamino, 4-pentylanilino, 6,7-dimethoxy-1,2,3,4-tetrahydroisoquinolino, 3-(1-(4-methoxyphenyl)ethyl)anilino, 1-adamantanamino, 2-thiazoleamino, 3-hydroxyanilino, 2-(4-aminophenyl)-6-methylbenzothiazolo, 3-methylsulphonylanilino, 4-propylanilino, 2-fluoro-4-methylanilino, 4-chlorobenzylamino, 3-fluorobenzylamino, 4-bromo-3-methylanilino, (±)-α-(methylaminomethyl)benzyl alcohol, 5,6,7,8-tetrahydronaphthalene-1-amino, 3-methylbenzylamino, 4-(methylmercapto)anilino, 5-chloro-2-methylanilino, 4-(diethylamino)anilino, (±)-α-methylbenzylamino, 2-chlorobenzylamino, 4-fluorobenzylamino, 2-methoxybenzylamino, 2-methylbenzylamino, 3-bromo-4-methylanilino, 4-fluorophenethylamino, 4-ethoxyanilino, 2,5-difluorobenzylamino, 2,3-dimethylanilino, benzylamino, 4-aminopyridino, 4-chloroanilino, 3-fluorophenethylamino, 4-bromoanilino, 4-hydroxyanilino, 4-bromo-2-methylanilino, benzothiazol-2-amino, 6-methoxybenzothiazol-2-amino, 4-methylbenzylamino, 2,4-dimethylanilino, 6-fluorobenzothiazol-2-amino, 3-(methylmercapto)anilino, 2-methylanilino, 4-picolin-2-amino, 3-chloro-4-fluoroanilino, 4-fluoroanilino, 4-methoxybenzylamino, 3-ethoxyanilino, 4-methoxy-2-methylanilino, 4-methylanilino, 2,5-dimethylanilino, 2-methoxyanilino, 2-fluoroanilino, 3,5-dimethoxyanilino, 2-methoxy-5-methylanilino, 2-methoxy-5-nitroanilino, 2-(methylmercapto)anilino, cytosino, 3-trifluoromethylanilino, anilino, 3,4-dimethylanilino, 3,4,5-trimethoxyanilino, 2,5-dimethoxyanilino, 3-fluoroanilino, 3,4-dimethoxyanilino, 4-carboxamidoanilino, 2,4-difluoroanilino, 3-methoxyanilino, and 4-methoxyanilino; and Y is $C(O)NH_2$.

In the above Formula I, the $R^1$—Y substituents are such that Y is always bonded to the 1-position of the $R^1$ radical.

All naming hereinafter reflects this positioning between the two substituents.

In the above Formula I, the stereochemistry of chiral centers associated with the $R^1$ through $R^7$ groups can independently be in the R or S configuration, or a mixture of the two.

In the above Formula I, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_2$ to $C_7$ alkenyl" denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "$C_2$ to $C_7$ alkynyl" denotes such radicals as ethynyl, propynyl, butynyl, pentynyl, hexynyl, heptynyl, as well as di- and tri-ynes of straight and branched chains.

The term "$C_1$ to $C_6$ substituted alkyl," "$C_2$ to $C_7$ substituted alkenyl," and "$C_2$ to $C_7$ substituted alkynyl," denotes that the above $C_1$ to $C_6$ alkyl groups and $C_2$ to $C_7$ alkenyl and alkynyl groups are substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, $C_1$ to $C_7$ alkoxy, $C_1$ to $C_7$ acyl, $C_1$ to $C_7$ acyloxy, nitro, $C_1$ to $C_7$ alkyl ester, carboxy, protected carboxy, carbamoyl, carboxamide, protected carboxamide, N-($C_1$ to $C_6$ alkyl)carboxamide, protected N-($C_1$ to $C_6$alkyl) carboxamide, N,N-di($C_1$ to $C_6$ alkyl)carboxamide, cyano, methylsulfonylamino, thio, $C_1$ to $C_4$ alkylthio or $C_1$ to $C_4$ alkyl sulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "$C_1$ to $C_7$ alkoxy" as used herein denotes groups such as methoxy, ethoxy, n-propoxy, isopropoxy, n-butoxy, t-butoxy and like groups. A preferred alkoxy is methoxy.

The term "$C_1$ to $C_7$ acyloxy" denotes herein groups such as formyloxy, acetoxy, propionyloxy, butyryloxy, pentanoyloxy, hexanoyloxy, heptanoyloxy and the like.

Similarly, the term "$C_1$ to $C_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The substituent term "$C_3$ to $C_7$ cycloalkyl" includes the cyclopropyl, cyclobutyl, cycloheptyl, cyclohexyl or cycloheptyl rings. The substituent term "$C_3$ to $C_7$ substituted cycloalkyl" indicates the above cycloalkyl rings substituted by one or two halogen, hydroxy, protected hydroxy, $C_1$ to $C_6$ alkyl, $C_1$ to $C_7$ alkoxy, oxo, protected oxo, (monosubstituted)amino, (disubstituted)amino, trifluoromethyl, carboxy, protected carboxy, phenyl, substituted phenyl, amino, or protected amino groups.

The term "$C_5$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_5$ to $C_7$ cycloalkenyl" denotes the above $C_5$ to $C_7$ cycloalkenyl rings substituted by a $C_1$ to $C_6$ alkyl radical, halogen, hydroxy, protected hydroxy, $C_1$ to $C_7$ alkoxy, trifluoromethyl, carboxy, protected carboxy, oxo, protected oxo, (monosubstituted)amino, protected (monosubstituted) amino(disubstituted)amino, phenyl, substituted phenyl, amino, or protected amino.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully saturated or partially unsaturated, with fully saturated rings being preferred. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophen-yl.

The abbreviation "Ar" stands for an aryl group. Aryl groups which can be used with present invention include phenyl, substituted phenyl, as defined above, heteroaryl, and substituted heteroaryl. The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino carboxamide, protected carboxamide, N-($C_1$ to $C_6$alkyl) carboxamide, protected N-($C_1$ to $C_6$ alkyl)carboxamide, N, N-di($C_1$ to $C_6$ alkyl), trifluoromethyl, N-(($C_1$ to $C_6$ alkyl) sulfonyl)amino or N-(phenylsulfonyl)amino groups.

The term "$C_7$ to $C_{12}$ phenylalkyl" denotes a $C_1$ to $C_6$ alkyl group substituted at any position by a phenyl ring. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, monosubstituted) amino, protected (monosubstituted)amino, (disubstituted) amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N,N-($C_1$ to $C_6$dialkyl)carboxamide, cyano, N-($C_1$ to $C_6$ alkylsulfonyl) amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N, N-di($C_1$ to $C_6$ alkyl)carboxamide, trifluoromethyl, N-(($C_1$ to $C_6$ alkyl)sulfonyl)amino, N-(phenylsulfonyl)amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxy phenyl)-n-hexyl, 2-(5-cyano-3-methoxyphenyl)-n-pentyl, 3-(2,6-dimethylphenyl)-n-propyl, 4-chloro-3-aminobenzyl, 6-(4-methoxyphenyl)-3-carboxy(n-hexyl), 5-(4-aminomethylphenyl)-3-(aminomethyl)-n-pentyl, 5-phenyl-3-oxo-n-pent-1-yl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2,3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted aniline" specifies an aniline group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ $C_6$ alkyl)carboxamide, N,N-di($C_1$ to $C_6$ alkyl)carboxamide, trifluoromethyl, N-(($C_1$ to $C_6$ alkyl)sulfonyl)amino and N-(phenylsulfonyl)amino.

Examples of substituted aniline includes, for example, 2-fluoroanilinyl, 3-fluoroanilinyl, 4-fluoroanilinyl, 2-chloroanilinyl, 3-chloroanilinyl, 4-chloroanilinyl, 2-bromoanilinyl, 3-bromoanilinyl, 4-bromoanilinyl, 2-methoxyanilinyl, 3-methoxyanilinyl, 4-methoxyanilinyl, 2-hydroxyanilinyl, 3-hydroxyanilinyl, 4-hydroxyanilinyl, 2-carboethoxyanilinyl, 3-carboethoxyanilinyl, 4-carboethoxyanilinyl, 2-trifluoromethylanilinyl, 3-trifluoromethylanilinyl, 4-trifluoromethylanilinyl, 2-dimethylaminoanilinyl, 3-dimethylaminoanilinyl, 4-dimethylaminoanilinyl, 2-phenoxyanilinyl, 3-phenoxyanilinyl, 4-phenoxyanilinyl, 3,4-methylenedioxyanilinyl, 2,3-methylenedioxyanilinyl, 2,3-difluoroanilinyl, 2,3-dibromoanilinyl, 3,4-dibromoanilinyl, 2,3-dimethoxyanilinyl, 3,4-dimethoxyanilinyl, 1-amino-5,6, 7,8-tetrahydronaphthyl, 2-hydroxy-3-amino-5,6,7,8-tetrahydronaphthyl, 2-aminonaphthyl, 1-amino-4-chloronaphthyl, 1-amino-4-bromonaphthyl, 5-amino-1-hydroxynaphthyl, 1-amino-2-hydroxynaphthyl, 5-aminoindanyl, 1-aminofluorenyl, 2-aminofluorenyl and N-methylanilinyl.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)amino or N-(phenylsulfonyl)amino.

Examples of the term "substituted naphthyl" includes a mono or di(halo)naphthyl group such as 1, 2, 3, 4, 5, 6, 7 or 8-chloronaphthyl, 2,6-dichloronaphthyl, 2,5-dichloronaphthyl, 3,4-dichloronaphthyl, 1, 2, 3, 4, 5, 6, 7 or 8-bromonaphthyl, 3,4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2,4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1,2,4-dimethylnaphthyl, 1, 2, 3, 4, 5, 6, 7 or 8-(isopropyl)naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy) naphthyl group, for example, 2,6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy) naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2,4-di(-protected carboxy) naphthyl; a mono-or di(hydroxymethyl)naphthyl or (protected hydroxymethyl)naphthyl such as 1, 2, 3, 4, 5, 6, 7 or 8-(protected hydroxymethyl)naphthyl or 3,4-di (hydroxymethyl)naphthyl; a mono- or di(amino)naphthyl or (protected amino)naphthyl such as 1, 2, 3, 4, 5, 6, 7 or 8-(amino)naphthyl or 2,4-(protected amino)-naphthyl, a mono- or di(aminomethyl)naphthyl or (protected aminomethyl)naphthyl such as 2, 3, or 4-(aminomethyl) naphthyl or 2,4-(protected aminomethyl)-naphthyl; or a mono- or di-(N-methylsulfonylamino)naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The terms "halo" and "halogen" refer to the fluoro, chloro, bromo or iodo groups. There can be one or more halogen, which are the same or different. Preferred halogens are chloro and fluoro.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_2$ to $C_7$ substitued alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino."

The term "(disubstituted)amino" refers to amino groups with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, dithiasuccinoyl ("Dts"), the 2-(nitro)phenylsulfenyl group ("Nps"), the diphenylphosphine oxide group and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6- trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, isopropylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_4$ alkylsulfonyl" encompasses groups such as methylsulfonyl, ethylsulfonyl, n-propylsulfonyl, isopropylsulfonyl, n-butylsulfonyl, t-butylsulfonyl and the like.

By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the the cyclic $C_2$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, carbamoyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstitued)amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the phenyl is fused to a pyridino, pyrano, pyrrolo, pyridinyl, dihydropyrrolo, or dihydropyridinyl ring. Examples of fused cyclic groups which each contain one oxygen atom and one or two double bonds are when the phenyl ring is fused to a furo, pyrano, dihydrofurano, or dihydropyrano ring. Examples of fused cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

One or more of the isoquinoline derivatives, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.*, 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the above Formulae can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more isoquinoline derivatives, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the α-($C_1$ to $C_7$)alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_4$ alkylthiomethyl groups, for example methylthiomethyl, ethylthiomethyl, isopropylthiomethyl and the like; the acyloxymethyl groups, for example pivaloyloxymethyl, pivaloyloxyethyl, α-acetoxymethyl and the like; the ethoxycarbonyl-1-methyl group; the α-acetoxyethyl; the 1-($C_1$ to $C_7$ alkyloxycarbonyloxy)ethyl groups such as the 1-(ethoxycarbonyloxy)ethyl group; and the 1-($C_1$ $C_7$ alkylaminocarbonyloxy)ethyl groups such as the 1-(methylaminocarbonyloxy)ethyl group.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), β-Alanine, L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration.

As used herein, the phrase "any one of the twenty naturally-occurring amino acids" means any one of the following: Ala, Arg, Asn, Asp, Cys, Gln, Glu, Gly, His, Ile, Leu, Lys, Met, Phe, Pro, Ser, Thr, Trp, Tyr, and Val. As used herein, the language "the D-form of a naturally-occurring amino acid" means the D-isomer of any one of these naturally-occurring amino acids, with the exception of Gly, which does not occur as D or L isomers.

The compounds of Formula I and combinatorial libraries containing the same can be prepared as set forth in the Reaction Schemes below. The substituents $R^1$, $R^2$, $R^7$, X and Y in the Reaction Schemes have the same meaning as those described above. Moreover, it should be appreciated from the Reaction Schemes that homophthalic anhydride, wherein each of $R^3$, $R^4$, $R^5$, and $R^6$ are a hydrogen atom, is only an exemplary anhydride in the Reaction Schemes and that other anhydrides having the above-defined $R^3$, $R^4$, Rand $R^6$ substituents can alternatively be used. Further, the Y representation that Y is carboxamide is also exemplary and other Y groups can be used.

In brief, the isoquinoline compounds of the present invention can be prepared according to Reaction Scheme I. As depicted therein, a solid support resinbound amine (1) (resin identified by ®) is reacted, in situ, with an aldehyde (2) and, thereby, converted to the corresponding imine (3). Addition of a cyclic anhydride, such as homophthalic anhydride (3), yields isoquinoline (4).

REACTION SCHEME I

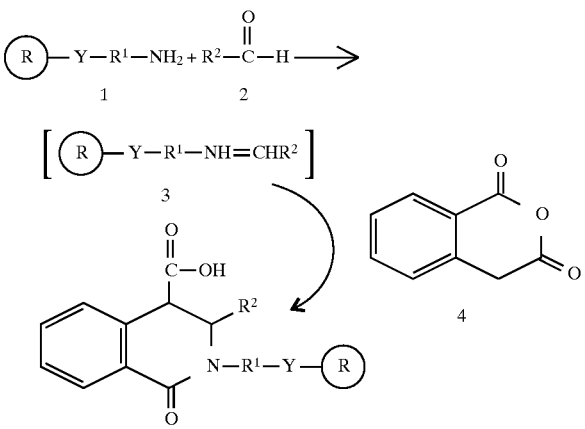

More specifically, as shown by Reaction Scheme II below, preparation of the isoquinolines and libraries containing the same are prepared by the following more detailed steps. First, diverse amino carboxylic acids which are amino-protected are coupled to resin, such as MBHA, MBA, Tentagel™ and the like as described below, using a carbodiimide coupling agent, such as dicyclohexylcarbodiimide, diisopropylcarbodiimide, N-dimethylaminoethyl-N'-ethyl-carbodiimide and the like and an activator such as 1-hydroxybenzotriazole, 7-aza-1-hydroxybenzotriazole and the like in an aprotic polar solvent such as dichloromethane, dimethylformamide and the like at between 10° C. and 100° C., preferably at 25° C., for 2 to 24 hrs, preferably 8 to 16 hrs. Thereafter, the amino carboxylic acid is deprotected at the nitrogen with a secondary amine base using known conditions, such as, preferably piperidine (20% v/v), in DMF, (for Fmoc), trifluoroacetic acid (10–50% v/v) in dichloromethane (for Boc), for 5 to 60 min. Deprotection is followed by the free amino group being condensed with an aldehyde to the individual or mixtures of resin-bound amino carboxylic acids using, an orthoformate such as trimethyl or triethyl orthoformate as a scavenger for water, in a polar solvent such as dimethylformamide, dimethylacetamide, N-methylpyrrolidinone or the like for a period of 1 to 24 hrs, usually 3 to 5 hrs at 20° C. to 75° C. and preferably at 25° C. Aldehyde condensation is followed by reaction under standard conditions with cyclic anhydride, in the case of Reaction Scheme II, homophthalic anhydride, and an amine base (e.g. a trialkylamine) in an aprotic solvent such as chloroform, dimethylformamide, dimethylacetamide, N-methylpyrrolidinone for 2 to 36 hrs and preferably 16 hrs at 20° C. to 125° C., preferably at 20° C. to 30° C. to arrive at novel isoquinoline derivatives. Finally, the compounds were cleaved from the resin by the methods common to those skilled in the art and tested for biological activity. It should be appreciated by those of skill in the art that with certain resins, cleavage from the resin results in the functional group on the resin coming off the resin and being maintained with the cleaved compounds. For example, with an amino-resin, such as methylbenzhydrylamine resin, the amine group from the resin is cleaved off the resin and makes the isoquinoline(s) of interest an amide.

aminoethoxyethoxy)acetic acid, trans-4-(aminomethyl) cyclohexanecarboxylic acid and 4-(aminomethyl)benzoic acid.

Exemplary aldehydes used in the above Reaction Scheme II are 1,4-benzodioxan-6-carboxaldehyde, 1-methylindole-3-carboxaldehyde, 2,3-difluorobenzaldehyde, 2-bromobenzaldehyde, 2-chloro-5-nitrobenzaldehyde, 2-furaldehyde, 2-imidazolecarboxaldehyde, 2-naphthaldehyde, 2-pyridinecarboxaldehyde, 2-thiophenecarboxaldehyde, 3,4-dichlorobenzaldehyde, 3,5-bis(trifluoromethyl)benzaldehyde, 3,5-dihydroxybenzaldehyde, 3,5-dimethoxybenzaldehyde, 3,5,-dimethyl-4-hydroxybenzaldehyde, 3-(4-methoxyphenoxy) benzaldehyde, 3-furaldehyde, 3-hydroxybenzaldehyde,

REACTION SCHEME II

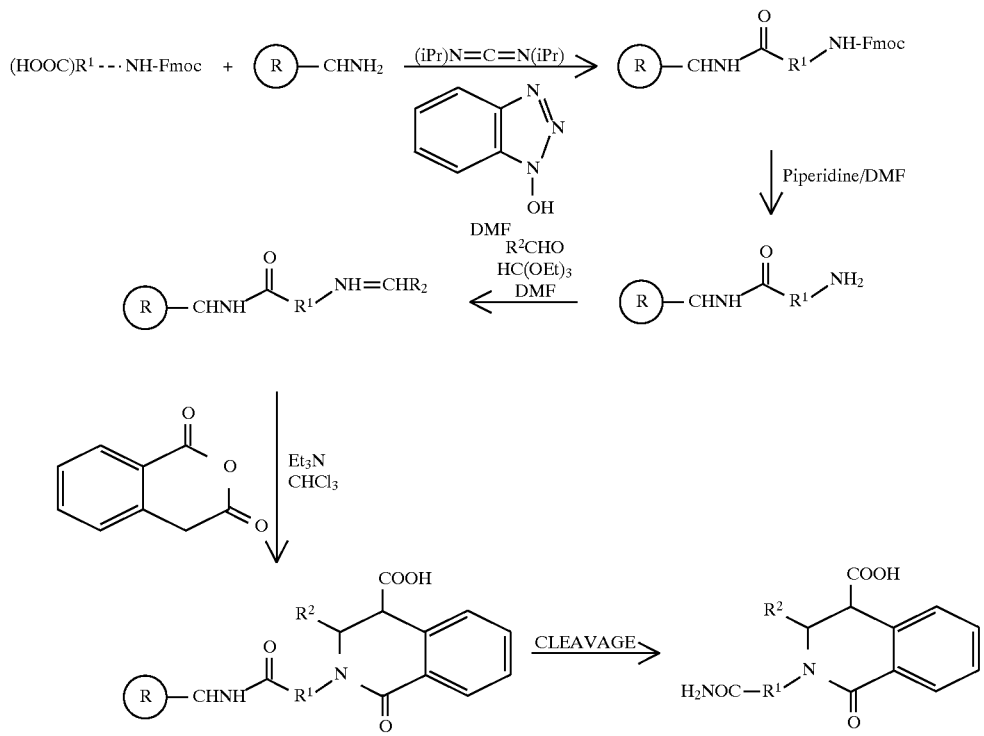

Resins which can serve as solid supports are well known in the art. Such resins include, for example, 4-methylbenzhydrylamine-copoly(styrene-1% divinylbenzene) (MBHA), 4-hydroxymethylphenoxymethyl-copoly(styrene-1%-divinylbenzene),4-oxymethyl-phenylacetamido-copoly (styrene-1% divinylbenzene) (Wang), and Tentagel™, from Rapp Polymere Gmbh, trialkoxy-diphenyl-methyl ester-copoly(styrene-1% divinylbenzene) (RINK) all of which are commercially available. Preparation of the combinatorial libraries can be by the "split resin approach." The split resin approach is described by, for example, U.S. Pat. No. 5,010, 175 to Rutter, WO PCT 91/19735 to Simon, and Gallop et al., *J. Med. Chem.*, 37:1233–1251 (1994), all of which are incorporated herein by reference.

Exemplary amino carboxylic acids used in the above Reaction Scheme II include 2-aminoethanoic acid, 3-aminopropionic acid, 5-aminopentanoic acid, 7-aminoheptanoic acid, (s)-2,3-diaminopropanoic acid, (s)-2,6-diaminohexanoic acid, (s)-3-amino-2-methylpropionic acid, (r)-3-amino-2-methylpropionic acid, 2-(2-

3-methyl-4-methoxybenzaldehyde, 3-methylbenzaldehyde, 3-nitrobenzaldehyde, 3-pyridinecarboxaldehyde, 3-thiophenecarboxaldehyde, 4-(3-dimethylaminopropoxy) benzaldehyde, 4-(dimethylamino)benzaldehyde, 4-(methylthio)benzaldehyde, 4-(trifluoromethyl) benzaldehyde, 4-biphenylcarboxaldehyde, 4-bromo-2-thiophenecarboxaldehyde, 4-cyanobenzaldehyde, 4-methoxy-1-naphthaldehyde, 4-nitrobenzaldehyde, 4-pyridinecarboxaldehyde, 5-(hydroxymethyl)-2-furaldehyde, 5-bromo-4-hydroxy-3-methoxybenzaldehyde, 5-nitro-2-furaldehyde, 6-methyl-2-pyridinecarboxaldehyde, and benzaldehyde.

Isoquinoline 4-carboxylic acids can be converted to alternatively substituted compounds having an amide or ester, or other functionality as defined by X, following Reaction Schemes III and IV. Briefly, as shown in Reaction Scheme III, condensation of the isoquinoline 4-carboxylic acid prepared by the above Reaction Schemes, is condensed with an amine or alcohol (4) in an aprotic solvent such as DMF to furnish the substituted isoquinoline (5).

REACTION SCHEME III

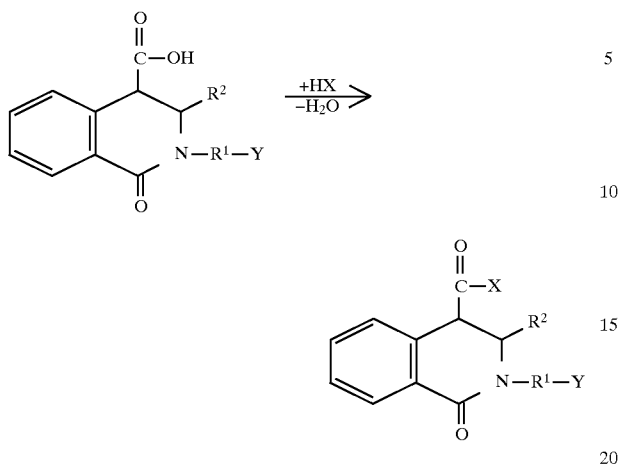

More specifically, as shown in Reaction Scheme IV, preparation of the library containing alternatively substituted isoquinolines other than 4-carboxylic acids involved the following steps described above but not performing the cleavage from the resin step once the carboxylic acid is formed. Instead the free carboxylic acid of the newly formed isoquinoline compounds is first treated with N-[(dimethylamino)-1H-1,2,3-triazolo[4,5-b]pyridin-1-ylmethylene]-N-methylmethanaminium hexafluorophosphate N-oxide (HATU, PerSeptive Biosystems, Farmingham, Mass.), and then different amines having varying R groups were added after dissolving in DMF, DMA, NMP, and the like. The reaction is allowed to proceed for 1 to 24 hrs at 20° C. to 80° C., preferably at 25° C. for 3 to 5 hrs to yield various carboxamide derivatives. Finally, the compounds were cleaved from the resin as described above and tested for biological activity.

REACTION SCHEME IV

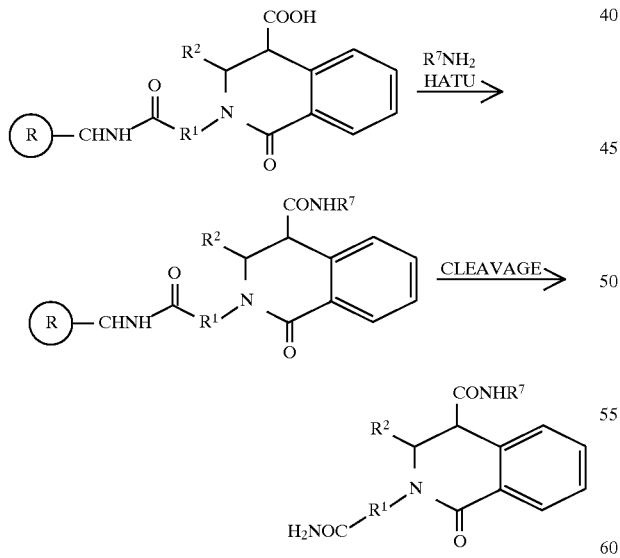

The present invention also provides libraries and individual compounds which are the corresponding amines of the above-described isoquinoline amide derivatives. Once the isoquinoline amide derivatives are prepared by above the described methods, the mixture can be further chemically transformed to extend the range and chemical diversity of the compounds. Using the "libraries from libraries" concept, as described in Ostresh et al., Proc. Natl. Acad. Sci., 91:11138–11142 (1994), various libraries of isoquinoline derivatives can be prepared by chemically altering the isoquinoline library. Such libraries and compounds will have the following structure:

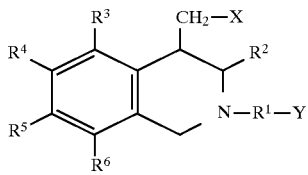

The preparation of such amines are described in Examples 48 to 50 and in one embodiment of the present invention, the substituents of the above Formula are as follows:

$R^1$ is selected from the group consisting of methylene, 1,2-ethyl, 1,3-propyl, 1,4-butyl, 1,5-pentyl, 1,6-hexyl, (S)-1-amino-1,2-ethyl, (S)-1-amino-1,5-pentyl, (R)-1-methyl-1,2-ethyl, (S)-1-methyl-1,2-ethyl,

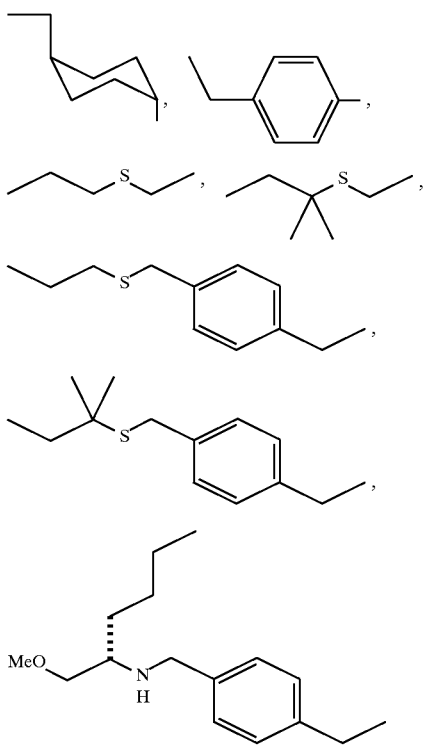

$R^2$ is selected from the group consisting of phenyl, 2-bromophenyl, 2-cyanophenyl, 2-fluorophenyl, 2-hydroxyphenyl, 2-methoxyphenyl, 3-bromophenyl, 3-(4-methoxybenzyl)phenyl, 3-cyanophenyl, 3-fluorophenyl, 3-hydroxyphenyl, 3-methoxyphenyl, 3-methylphenyl, 3-nitrophenyl, 3-(trifluoromethyl) phenyl, 4-(N-ethylamino)anilino, 4-bromophenyl, 4-(4-methoxybenzyl)phenyl, 4-cyanophenyl, 4-(3-dimethylaminopropoxy)phenyl, 4-fluorophenyl, 4-(dimethylamino)phenyl, 4-hydroxyphenyl, 4-isopropylphenyl, 4-methoxyphenyl, 4-methylphenyl, 4-methylsulphonylphenyl, 4-(methylthio)phenyl, 4-nitrophenyl, 4-propoxyphenyl, 4, (trifluoromethyl) phenyl, 3,5-bis(trifluoromethyl)phenyl, 3,5-dimethoxyphenyl, 3,5-dihydroxyphenyl, 3,5- dichlorophenyl, 2,3-difluorophenyl, 2,4-dichlorophenyl, 2-chloro-5-nitrophenyl, 2-chloro-6-fluorophenyl, 2,6-difluorophenyl, 3-bromo-4-fluorophenyl, 3,4-dihydroxyphenyl, 3,4-dichlorophenyl, 3,4-difluorophenyl, 3-fluoro-4-methoxyphenyl, 3-nitro-4-chlorophenyl, 3-hydroxy-4-methoxyphenyl, 3-hydroxy-4-nitrophenyl, 4-methoxy-3-(sulfonyl)phenyl, 3-methyl-4-methoxyphenyl, 2,3,4-trifluorophenyl, 2,3,5-trichlorophenyl, 3,5-dimethyl-4-hydroxyphenyl, 3-methoxy-4-hydroxy-5-bromophenyl, 3-methoxy-4-hydroxy-5-nitrophenyl, 1,4-benzodioxan-6-yl, 2,3-(methylenedioxy)phenyl, 3,4-(methylenedioxy)phenyl, 3,4-(methylenedioxy)-6-nitrophenyl, 8-hydroxyjulolidin-9-yl, 3-(3,4-dichlorophenoxy)phenyl, 3-(4-methoxyphenoxy) phenyl, 3-phenoxyphenyl, 4-phenoxyphenyl, 4-biphenyl, 1-naphthyl, 2-naphthyl, 4-methoxy-1-naphthyl, 2-quinolinyl, 3-quinolinyl, 4-quinolinyl, 8-hydroxyquinoline-2-yl, 9-ethyl-3-carbazolyl, 2-thiophenyl, 3-thiophenyl, 5-methyl-2-thiophen-yl, 2-furyl, 3-furyl, 5-methyl-2-furyl, 2-pyridinyl, 3-pyridinyl, 4-pyridinyl, 6-methyl-2-pyridinyl, pyrrole-2-yl, 1-methyl-2-pyrrolyl, 2-imidazolyl, 2-thiazolyl, 5-(4'-methoxybenzyl)-2-furyl, and 5-nitro-2-furyl;

$R^3$, $R^4$, $R^5$, $R^6$ are independently a hydrogen atom;

X is selected from the group consisting of anilino, 2-fluoroanilino, 2-methoxyanilino, 2-chlorobenzylamino, 2-methoxybenzylamino, 2-trifluoromethylbenzylamino, 3-fluoroanilino, 3-methylanilino, 3-trifluoromethylanilino, 3-(methylmercapto)anilino, 3-trifluoromethylbenzylamino, 3-methylbenzylamino, 4-propylanilino, 4-pentylanilino, 4-(methylmercapto) anilino, 4-fluorobenzylamino, 4-methoxybenzylamino, 4-methylbenzylamino, 3-(1-(4-methoxyphenyl)ethyl) anilino, 4-chloroanilino, 2,3-dimethylanilino, 4-methoxyanilino, 2,5-dimethoxyanilino, 3-chloro-4-fluoroanilino, 3-bromo-4-methylanilino, 3,4-dimethoxyanilino, 3,4-dimethylanilino, 3,5-dimethoxyanilino, 2-methylanilino, 3,4-dimethoxybenzylamino, 3,4-dichlorobenzylamino, 2-(3-chlorophenyl)ethylamino, 4-methoxyphenethylamino, N-benzylethanolamino, aminodiphenylmethane, 1-phenylpiperazino, 1-(α,α,α-trifluoro-m-tolyl)piperazino, 1,4-benzodioxan-6-amino, 4-(aminomethyl)pyridino, 3-(aminomethyl) pyridino, 1-(2-pyridyl)piperazino, cycloheptylamino, cyclohexylamino, 5-fluoro-2-methylanilino, 3-(aminomethyl)anilino, 1-methyl-3-phenylpropylamino, 1-adamantanemethylamino, 1,3,3-trimethyl-6-azabicyclo[3.2.1]octyl, 2-ethoxyanilino, 4-isopropylanilino, 3-phenyl-1-propylamino, trans-2-phenylcyclopropylamino, 3-nitrobenzylamino, 4-bromobenzylamino, 2-bromobenzylamino, 3-bromobenzylamino, 4-ethoxyanilino, 2-indanamino, 2,6-dimethoxypyridine-3-amino, 4-nitrobenzylamino, 4-hydroxyanilino, 5-bromo-2-fluorobenzylamino, 6,7-dimethoxy-1,2,3,4-tetrahydroisoquinolino, 2-adamantanamino, 2,4-dimethoxybenzylamino, 3-methylsulphonylanilino, 3-(dimethylamino)anilino, 4-(dimethylamino)anilino, pyridoxamino, 2-fluorophenethylamino, 3-fluorophenethylamino, 4-fluorophenethylamino, 2,4, dichlorophenethylamino, 3-iodoanilino, 3-chloro-2-methylanilino, 5-chloro-2-methoxyanilino, 4-methoxy-2-methylanilino, 2,4, dimethoxyanilino, 2,5-dimethylanilino, 2-fluoro-5-methylanilino, 2,3-dimethoxybenzylamino, 2,4-difluorobenzylamino, 2,5-difluorobenzylamino, 2,6-difluorobenzylamino, 5-chloro-2-methylanilino, 2,4-dimethylanilino, 2-fluoro-4-methylanilino, 3-phenoxyanilino, 4-phenoxyanilino, 2-fluorenamino, 1-naphthalenemethylamino, 3-hydroxyanilino, 4-aminopyridino, 4-picolinyl-2-amino, 5-indanamino 1-amino-5,6,7,8-tetrahydronaphthalenyl, tyramino, 1-(4-methoxyphenyl-1-phenylethyl-2-amino, 1-adamantanamino, 4-(4-methoxyphenyl)-4-phenylpiperidino, 4-chloro-2-methoxy-5-methylanilino, 4-morpholinoanilino, 3-chloro-4-methoxyanilino, hydroxyl, (±)-exo-2-norbornanamino, (±)-endo-2-norbornanamino, and (±)-α-methylbenzylamino; and Y is selected from the group consisting of $CH_2OH$, SH, $NHR^7$ and $CH_2NHR^7$, wherein $R^7$ is selected from the groups consisting of a hydrogen atom, $C_1$ to $C_6$ alkyl and $C_1$ to $C_6$ substituted alkyl.

The nonsupport-bound library mixtures were screened in solution in radio-receptor inhibition assays described in detail below. Deconvolution of highly active mixtures were carried out by iterative, and in one instance additionally, positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., *Nature,* 354, 84–86 (1991); and Dooley et al., *Science.* 266, 2019–2022 (1994); both of which are incorporated herein by reference. In the iterative approach, for example, sublibraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various organic libraries and for various peptide libraries (see, for example, R. Houghten et al. PCT/US91/08694 and U.S. Pat. No. 5,556,762, both of which are incorporated herein by reference). In the positional scanning approach sublibraries are made defining only one variable with each set of sublibraries- and all possible sublibraires with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the new isoquinoline derivatives, as well as methods of using the same are included within the scope of the present invention. The new isoquinoline compounds of the present invention can be used for a variety of purposes and indications and as medicaments for any such purposes and indications. For example, isoquinolines are generally known to have antimicrobial activity. Thus the isoquinolines of the present invention can be used to treat infections. The ability of the compounds to inhibit bacterial growth can be determined by methods well known in the art. An exemplary in vitro antimicrobial activity assay is described in Blondelle and Houghten, *Biochemistry* 30:4671–4678 (1991), which is incorporated herein by reference. In brief, *Staphylococcus aureus* ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 $\mu$l of the culture solution using serial dilutions (e.g., $10^{-2}$, $10^{-3}$ and $10^{-4}$) onto solid agar plates. In 96-well tissue culture plates isoquinolines, individual or in mixtures, are added to the bacterial suspension at concentrations derived from serial two-fold dilutions ranging from 1500 to 2.9 $\mu$g/ml. The plates are incubated overnight at 37° C. and the growth determined at each concentration by $OD_{620}$ nm. The $IC_{50}$ (the concentration necessary to inhibit 50% of the growth of the bacteria) can then be calculated.

Isoquinolines are also known to be antiarrhythmic and cardioprotective agents as described, for example, in published European Patent Application 0 590 455 to Lal et al., which is incorporated herein by reference. Therein is also described assays for assessing the antiarrhythmic and cardioprotective properties of isoquinolines, such as the reperfusion induced arrhythmias assay in isolated rat heart.

Additional assays can be, and have been, used to test the biological activity of the instant isoquinolines. Such assays include a competitive enzyme-linked immunoabsorbent assay and, as described in Examples 44 and 47, radio-receptor assays. The latter test, the radio-receptor assay, can be selective for any one of the $\mu$, $\kappa$, or $\delta$ opiate receptors and is, therefore, an indication of isoquinolines' analgesic properties as described, for example, in Dooley et al., *Proc. Natl. Acad. Sci.*, 90:10811–10815 (1993). Additionally, such compounds can, and have been as described in Example 47, tested in a $\sigma$ receptor assay. Ligands for the $\sigma$ receptor can be useful as antipsychotic agents, as described in Abou-Gharbia et al., *Annual Reports in Medicinal Chemistry*, 28:1–10 (1993).

Competitive Enzyme-Linked Immunosorbent Assay (ELISA): The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 $\mu$l. After blocking, 25 $\mu$l of a 1.0 mg/ml solution of each isoquinoline mixture of a synthetic combinatorial library (or individual isoquinoline) is added, followed by MAb 125-1OF3 (Appel et al., supra) (25 $\mu$l per well). The MAb is added at a fixed dilution in which the isoquinoline in solution effectively competes for MAb binding with the antigenic peptide adsorbed to the plate. The remaining steps are the same as for direct ELISA. The concentration of isoquinoline necessary to inhibit 50% of the MAb binding to the control peptide on the plate ($IC_{50}$) is determined by serial dilutions of the isoquinoline.

Radio-Receptor Assay: Particulate membranes can be prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized 40 ml Tris-HCl buffer (50 mM, pH 7.4, 4° C.) and centrifuged (Sorvall® RC5C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M. M. Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H-[D-Ala$^2$,Me-Phe$^4$,Gly-ol$^5$]enkephalin (DAMGO) (specific activity=36 Ci/mmol, 160,000 cpm per tube; which can be obtained from Multiple Peptide Systems, San Diego, Calif., through NIDA drug distribution program 271-90-7302) and 80 $\mu$g/ml of isoquinoline, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the isoquinolines, individually or in mixtures. $IC_{50}$ values (the concentration necessary to inhibit 50% of $^3$H-DAMGO binding) are then calculated. As opposed to this $\mu$ receptor selective assay, assays selective for $\kappa$ receptors can be carried out using [$^3$H]-U69,593 (3 nM, specific activity 62 Ci/mmol) as radioligand. Assays selective for $\delta$ opiate receptors can be carried out using tritiated DSLET ([D-Ser$^2$, D-Leus]-threonine-enkephalin) as radioligand. Similarly, assays for the $\sigma$ receptor assay are the same as the $\mu$ assay but use radiolabeled pentazocine as ligand.

As pharmaceutical compositions for treating infections, arrhythmia, pain, or other indications known to be treatable by isoquinolines, the isoquinoline compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active isoquinoline. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

EXAMPLE 1

Combinatorial Library Of Dihydroisoquinoline Derivatives

This Example provides a representative solid-phase combinatorial synthesis of a library which would contain approximately 525 derivatives of dihydroisoquinolines (DHQs).

Following the above Reaction Scheme II, preparation of a library containing the DHQs involves the following steps. Briefly, first, thirty five diverse amino carboxylic acid, varying at $R^1$, and including various amino-protected amino acids, are coupled to MBHA resin employing the tea-bag method of Houghten, et. al, as described, for example in U.S. Pat. No. 4,631,211 to Houghten and Houghten et al., *Proc. Natl. Acad. Sci.*, 82:5131–5135 (1985), both of which are incorporated herein by reference. After coupling and thorough washing the 35 tea-bags, each containing one resin-bound amino carboxylic acid, are opened and the resin beads combined and thoroughly mixed as a suspension in dichloromethane (DCM). The resins are isolated by filtration and dried under vacuum, then divided into 15 equal portions and resealed in 15 labeled tea-bags, each tea-bag now having a mixture of the 35 amino carboxylic acids. This is followed by condensing 15 aldehydes, each differing by their $R^2$ substituent, using triethylorthoformate as dehydrating agent with the tea-bag contained mixtures of resin-bound amino carboxylic acids. One tea-bag, each containing the 35 resin-bound carboxylic acids, is used for each aldehyde in a separate reaction. After washing with an anhydrous solvent the tea-bags are collectively reacted with homophthalic anhydride and triethylamine in anhydrous dimethylformamide (DMF) to arrive at a library of 525 derivatives of DHQ. Finally, the compounds are individually cleaved from the MBHA resin using a hydrogen fluoride (HF) procedure. The individual mixtures varying at $R^1$ and constant at $R^2$, each a mixture containing 35 individual compounds can then be tested for biological activity using any one of a variety of screening assays, such as those described above or others well known in the art.

The individual amino carboxylic acids which can be used to prepare a library of 525 DHQs include the following: Ala, Arg, Asn, Asp, Cys, Gln, Glu, Gly, His, Ile, Leu, Lys, Met, Phe, Ser, Thr, Trp, Tyr, Val, D-Ala, D-Asp, D-Cys, D-Glu, D-Ile, D-Leu, D-Lys, D-Met, D-Phe, D-Ser, D-Thr, D-Tyr, and D-Val, β-alanine, and 4-aminobutyric acid. All are amino-protected with Fmoc or Boc and carry appropriate side chain protecting group as required. Individual aldehydes which can be employed are as follows: benzaldehyde, 4-methoxybenzaldehyde, 4-nitrobenzaldehyde, 4-chlorobenzaldehyde, 2-methoxybenzaldehyde, 2-nitrobenzaldehyde, 2-chlorobenzaldehyde, 4-phenylbenzaldehyde, furfuraldehyde, 2-propionaldehyde, 2-methyl-2-buten-1-al, cyclohexane carboxaldehyde, butanal, cinnamaldehyde, acetaldehyde.

1. Coupling of Amino Carboxylic Acids to MBHA Resin

Thirty five polypropylene mesh packets (T-bags, ~2" square, 65μ; McMaster Carr, Chicago, Ill.) of (0.6 g, 0.93 meq/g) MBHA resin are prepared, washed with DCM (2×, ~5 ml each), neutralized with 5% diisopropylethylamine/ dichloromethane (DIEA/DCM) (3×, ~5 ml each), and washed with DCM (2×, ~5 ml each). Each resin packet is individually coupled overnight (~16 hrs except for Gly, 1 hr) by adding 10× amino acid in DCM (0.2M) or amino carboxylic acid in DMF followed by 10× diisopropylcarbodiimide/DCM (0.2M) for a final reagent concentration of 0.1M DMF (5%) used to solubilize the Arg and Ser derivatives. Hydroxybenzotriazole (HOBt) (10×) is added to the amino carboxylic acids couplings. Following coupling completion, resin packets are washed with DCM (1×), isopropanol (IPA) (2×), and DCM (2×). Each packet is then opened and the resin carefully washed into a common vessel using alternating DCM and methanol (MeOH) washes (final volume, ~200 ml). The resin is mixed using a magnetic stir bar for 2.5 hrs. Resin is then filtered, washed with MeOH, and dried under vacuum. Based upon synthesis and cleavage of individual controls, reaction completion should be, and generally is, >95%.

2. Condensation of Benzaldehydes to the Mixture of Resin-Bound Amino Carboxylic Acids Each packet is next shaken twice in 20% (v/v) piperidine/DMF (30 ml, 5 min, then 15 min) then washed with DMF (3×30 ml) and DCM (3×30 ml). A solution of the respective aldehyde (0.203 ml, 2 mmoles) and anhydrous trimethylorthoformate (0.438 ml, 4 mmoles) is prepared in DMF (7.5 ml) and added to the packet. After shaking for 3 hrs the packet is washed with dry (<0.03% water) DMF (5×30 ml).

3. Condensation of Homophthalic Anhydride to Yield a Library of Dihydroisoquinolines A solution of homophthalic anhydride (324 mg, 2 mmoles) and triethylamine (0.021 ml, 0.15 mmoles) is prepared in DMF (5 ml) and added to each packet. After heating at 80° C. for 16 hrs the packets are then washed with DMF (3×30 ml) and DCM (3×30 ml).

The isoquinolines are cleaved off of the resin by treatment with HF (liquid (1)) at ~15° C. for 2 hrs followed by warming to room temperature while removing HF (gaseous (g)) with a nitrogen stream.

EXAMPLE 2 trans-N-(2-acetamidoyl)-3-phenyl-4-carboxy-3,4-dihydro-1(2H)-isoquinolone

This Example provides the solid-phase synthesis of trans-N-(2-acetamidoyl)-3-phenyl-4-carboxy-3,4-dihydro-1(2H)-isoquinolone by condensing, on a TentaGel™ resin, glycine, benzaldehyde and homophthalic anhydride. The isoquinoline was cleaved from the resin by trifluoroacetic acid (TFA).

TentaGel™ S-NH$_2$ resin (Rapp Polymere Gmbh, Federal Republic of Germany; 385 mg, 0.100 milliequivalents) was placed in a porous polypropylene packet. The packet was placed in a 60 ml bottle and washed with 5% (v/v) DIEA/DCM (3×30 ml) followed by DCM (5×30 ml). A solution of Rink linker (270 mg, 0.5 mmoles), HOBt (68 mg, 0.5 mmoles), and diisopropylcarbodiimide (DIC, 0.094 ml, 0.6 mmoles) was prepared in DMF (5 ml) and added to the resin packet. After shaking for 16 hrs the packet was washed with DMF (3×30 ml) and DCM (3×30 ml).

The packet was next shaken twice in 20% (v/v) piperidine/DMF (30 ml, 5 min, then 15 min), then washed with DMF (3×30 ml) and DCM (3×30 ml). A solution of N-(9-fluorenylmethoxycarbonyl)glycine (149 mg, 0.5 mmoles), HOBt (68 mg, 0.5 mmoles), and DIC (0.094 ml, 0.6 mmoles) was prepared in DMF (5 ml) and added to the resin packet. After shaking for 2 hrs the packet was washed with DMF (3×30 ml) and DCM (3×30 ml).

The packet was next shaken twice in 20% (v/v) piperidine/DMF (30 ml, 5 min, then 15 min) then washed with DMF (3×30 ml) and DCM (3×30 ml). A solution of benzaldehyde (0.203 ml, 2 mmoles) and anhydrous trimethylorthoformate (0.438 ml, 4 mmoles) was prepared in DMF (7.5 ml) and added to the packet. After shaking for 3 hrs the packet was washed with dry (<0.03% water) DMF (5×30 ml). A solution of homophthalic anhydride (324 mg, 2 mmoles) and triethylamine (0.021 ml, 0.15 mmoles) was prepared in DMF (5 ml) and added to the packet. After heating at 80° C. for 16 hrs the packet was washed with DMF (3×30 ml) and DCM (3×30 ml).

The isoquinolone was cleaved off of the resin by addition of a solution of 75/20/5 (v/v/v) TFA/DCM/water (10 ml). After shaking for 135 min the acid solution was decanted into a round bottom flask. The packet was then washed with TFA (1×10 ml) and this wash was also added to the round bottom flask. The solvent was removed under reduced pressure providing a clear oil.

The crude oil was dissolved in DCM (20 ml and extracted with 1N hydrochloric acid (HCl; 1×10 ml). The organic layer was next extracted with aqueous saturated sodium bicarbonate (NaHCO$_3$) (2×10 ml) The NaHCO$_3$ layers were combined and the pH of the solution was brought to 1–2 by addition of 2N HCl, followed by extraction with DCM (2×10 ml). The final organic layers were combined and the solvent was removed under reduced pressure, providing a quantitative yield of a clear oil which crystallized overnight into a white solid. 1H NMR (DMSO-d6) d 7.98 (d, 1H, J=2.4 Hz), 7.46 (m, 3H), 7.25 (m, 5H), 7.11 (m, 2H), 5.41 (d, 1H, J=1.7 Hz), 4.39 (d, 1H, J=16.3 Hz), 4.14 (d, 1H, J=1.7 Hz), 3.34 (d, 1H, J=16.3 Hz). 13C NMR (DMSO-d6) d 172.98, 169.77, 163.41, 138.86, 133.46, 132.34, 129.25, 128.63, 128.21, 128.09, 127.70, 127.08, 126.28, 61.67, 50.41, 49.89. Matrix Assisted Laser Desorption Ionization-Time of Flight Mass Spectrometry (MALDI-TOF MS; Kratos (division of Shimadzu Scientific), Columbia, Md.): 364 (MW+2 Na+), (347 (MW+Na+).

EXAMPLE 3 trans-N-(2-acetamidoyl)-3-phenyl-4-carboxy-3,4-dihydro-1(2H)-isoquinolone

This Example provides the solid-phase synthesis of trans-N-(2-acetamidoyl)-3-phenyl-4-carboxy-3,4-dihydro-1(2H)-isoquinolone by condensing, on a polystyrene benzhydrylamine resin, glycine, benzaldehyde and homophthalic anhydride. The final product was cleaved from the resin using an HF procedure.

Polystyrene benzhydrylamine (BHA) resin (189 mg, 0.100 milliequivalents) was placed in a porous polypropylene packet. The packet was placed in a 60 ml bottle and washed with 5% (v/v) DIEA/DCM(3×30 ml) followed by DCM (5×30 ml). A solution of N-(9-fluorenylmethoxycarbonyl)glycine (149 mg, 0.5 mmoles), HOBt (68 mg, 0.5 mmoles), and DIC (0.094 ml, 0.6 mmoles) was prepared in DMF (5 ml) and added to the resin packet. After shaking for 2 hrs the packet was washed with DMF (3×30 ml) and DCM (3×30 ml).

The packet was next shaken twice in 20% (v/v) piperidine/DMF (30 ml, 5 min, then 15 min), then washed with DMF (3×30 ml) and DCM (3×30 ml). A solution of benzaldehyde (0.203 ml, 2 mmoles) and anhydrous trimethylorthoformate (0.438 ml, 4 mmoles) was prepared in DMF (7.5 ml) and added to the packet. After shaking for 3 hrs the packet was washed with dry (<0.03% water) DMF (5×30 ml). A solution of homophthalic anhydride (324 mg, 2 mmoles) and triethylamine (0.021 ml, 0.15 mmoles) was prepared in DMF (5 ml) and added to the packet. After heating at 80° C. for 16 hrs the packet was washed with DMF (3×30 ml) and DCM (3×30 ml).

The isoquinoline was cleaved off of the resin by treatment with HF (l) at −15° C. for 2 hrs followed by warming to room temperature while removing HF (g) with a nitrogen stream. The packet and HF tube were washed with TFA (2×8 ml) and the two washes were transferred to a round bottom flask and concentrated to a clear oil under reduced pressure.

The crude oil was dissolved in DCM (20 ml and extracted with 1N HCl (1×10 ml). The organic layer was next extracted with aqueous saturated NaHCO$_3$ (2×10 ml). The NaHCO$_3$ layers were combined and the pH of the solution was brought to 1–2 by addition of 2N HCl, followed by extraction with DCM (2×10 ml). The final organic layers were combined and the solvent was removed under reduced pressure, providing a quantitative yield of a clear oil which upon lyophilization provided a white crystalline solid. Spectral data was identical to the sample prepared in Example 2.

EXAMPLE 4 trans-N-(2-(s)-propionamidoyl)-3-phenyl-4-carboxy-3,4-dihydro-1(2H)-isoquinolone Provided by this Example is the solid-phase synthesis of trans-N-(2-(s)-propionamidoyl)-3-phenyl-4-carboxy-3,4-dihydro-1(2H)-isoquinolone prepared by condensing, on an MBHA resin, alanine, benzaldehyde and homophthalic anhydride. The final product was removed from the resin by HF cleavage.

N-(t-Butyloxycarbonyl)-L-alanine attached to MBHA resin (0.05 mmoles) was sealed in a polypropylene packet. The packet was shaken in 55% (v/v) TFA/DCM (30 ml, 30 min) then washed with DCM (1×30 ml), isopropyl alcohol (2×30 ml), 5% (v/v) DIEA/DCM (3×30 ml, 2 min each), DCM (2×30 ml), and anhydrous DMF (2×30 ml).

A solution of benzaldehyde (10 mmoles) and anhydrous trimethylorthoformate (20 mmoles) was prepared in DMF (20 ml) and added to the packet. After shaking for 3.75 hrs the packet was washed with dry (<0.03% water) DMF (5×30 ml). A solution of homophthalic anhydride (7.5 mmoles) and triethylamine (225 mmoles) was prepared in chloroform (15 ml) and added to the packet. After shaking at room temperature for 17 hrs the packet was washed with DCM (3×30 ml), DMF (3×30 ml), shaken for 20 min in water (30 ml), washed with DMF (3×30 ml) and DCM (3×30 ml).

The isoquinolone was cleaved off of the resin using HF as in Example 3, but no aqueous extraction was performed. The residue was dissolved in deuterated DMSO to obtain NMR and mass spectral data after which the solvent was removed under reduced pressure providing a 1/1 mixture of the desired product and the amide arising from homophthalic acid and L-alaninamide as a clear oil. (14 mg, 83%). MALDI-TOF MS: 338 (MW), 359 (MW+Na+).

EXAMPLE 5 trans-N-(3-propionamidoyl)-3-phenyl-4-carboxy-3,4-dihydro-1(2H)-isoquinolone

This Example provides the solid-phase synthesis of trans-N-(3-propionamidoyl)-3-phenyl-4-carboxy-3,4-dihydro-1(2H)-isoquinolone prepared by condensing, on a RINK linker derivatized TentaGel™ resin, aminopropionic acid, benzaldehyde and homophthalic anhydride. The final product was removed from the resin by TFA cleavage.

N-(9-Fluorenylmethoxycarbonyl)-3-aminopropionic acid was attached to RINK linker derivatized TentaGel™ resin as described in Example 2. The packet was next shaken twice in 20% (v/v) piperidine/DMF (30 ml, 5 min, then 15 min) then washed with DMF (3×30 ml) and DCM (3×30 ml).

A solution of benzaldehyde (0.203 ml, 2 mmoles) and anhydrous trimethylorthoformate (0.438 ml, 4 mmoles) was prepared in DMF (7.5 ml) and added to the packet. After shaking for 3 hrs the packet was washed with dry (<0.03% water) DMF (5×30 ml) followed by chloroform (3× 30 ml). A solution of homophthalic anhydride (324 mg, 2 mmoles) and triethylamine (0.021 ml, 0.15 mmoles) was prepared in chloroform (5 ml) and added to the packet. After shaking at room temperature for 18 hrs the packet was washed with DCM (3×30 ml), DMF (3×30 ml) and water (1×30 ml). The packet was then shaken in water (30 ml) for 20 min followed by washing with DMF (3×30 ml) and DCM (3×30 ml).

The isoquinolone was cleaved off of the resin by addition of a solution of 75/20/5 (v/v/v) TFA/DCM/water (10 ml). After shaking for 135 min the acid solution was decanted into a round bottom flask. The packet was then washed with TFA (1×10 ml) and this wash was also added to the round bottom flask. The solvent was removed under reduced pressure providing a clear oil.

The crude oil was dissolved in 1 ml methyl sulfoxide and half was stored at −20° C. The other half was mixed with 1N NaOH (10 ml) and stirred at room temperature for 1 hr. Water (5 ml) was then added and the solution was extracted with DCM (1×10 ml). The pH of the aqueous layer was brought to 1–2 by addition of 2N HCl, followed by extraction with DCM (2×10 ml). The final organic layers were combined and the solvent was removed under reduced pressure, providing a clear oil (15 mg, 89%). MALDI-TOF MS: 360 (MW+Na+).

EXAMPLE 6 TO EXAMPLE 28

Synthesis of Additional Substituted Isoquinolines

With the exception of the amino carboxylic acid and aldehyde starting materials, Examples 6 to 28 were done using the procedures of Example 5. In place of the starting materials 3-aminopropionic acid and benzaldehyde of Example 5, Examples 6 to 28 provide all possible combinations of four different amino carboxylic acids and six unique benzaldehydes. The amino carboxylic acids and benzaldehydes used, along with the corresponding Example number is shown in TABLE I. As a reference, the compound prepared in Example 5 is shown in Table I at upper left.

TABLE I

|  | 3-Amino-propionic acid | 4-Amino-butyric acid | 6-Amino-hexanoic acid | Glycine |
|---|---|---|---|---|
| Benzaldehyde | Example 5 | Example 11 | Example 17 | Example 23 |
| 4-Methoxy-benzaldehyde | Example 6 | Example 12 | Example 18 | Example 24 |
| 3,5-Dimethoxy-benzaldehyde | Example 7 | Example 13 | Example 19 | Example 25 |
| 4-Cyano-benzaldehyde | Example 8 | Example 14 | Example 20 | Example 26 |
| 2-Bromo-benzaldehyde | Example 9 | Example 15 | Example 21 | Example 27 |
| 3-Hydroxy-benzaldehyde | Example 10 | Example 16 | Example 22 | Example 28 |

EXAMPLE 6 trans-N-(3-propionamidoyl)-3-(4-methoxyphenyl)-4-carboxy-3,4-dihydro-1(2H)-isoquinolone Yield: 16 mg, 87%. MALDI-TOF MS: 390 (MW+Na+), 406 (MW+K+).

EXAMPLE 7 trans-N-(3-propionamidoyl)-3-(3,5-dimethoxyphenyl)-4-carboxy-3,4-dihydro-1(2H)-isoquinolone Yield: 15 mg, 75%. MALDI-TOF MS: 421 (MW+Na+).

EXAMPLE 8 trans-N-(3-propionamidoyl)-3-(4-cyanophenyl)-4-carboxy-3,4-dihydro-1(2H)-isoquinolone Yield: 9 mg, 50%. MALDI-TOF MS: 363 (MW), 385 (MW+Na+).

EXAMPLE 9 trans-N-(3-propionamidoyl)-3-(2-bromophenyl)-4-carboxy-3,4-dihydro-1(2H)-isoquinolone Yield: 17 mg, 82%. MALDI-TOF MS: 417 (MW), 439 (MW+Na+).

EXAMPLE 10 trans-N-(3-propionamidoyl)-3-(3-hydroxyphenyl)-4-carboxy-3,4-dihydro-1(2H)-isoquinolone Yield: 2 mg, 11%. MALDI-TOF MS: 354 (MW), 376 (MW+Na+).

EXAMPLE 11 trans-N-(4-butyramidoyl)-3-(phenyl)-4-carboxy-3,4-dihydro-1(2H)-isoquinolone

Yield: 17 mg, 97%. MALDI-TOF MS: 374 (MW+Na+).

EXAMPLE 12 trans-N-(4-butyramidoyl)-3-(4-methoxyphenyl)-4-carboxy-3,4-dihydro-1(2H)-isoquinolone Yield: 11 mg, 58%. MALDI-TOF MS: 382 (MW), 404 (MW+Na+).

EXAMPLE 13 trans-N-(4-butyramidoyl)-3-(3,5-dimethoxyphenyl)-4-carboxy-3,4-dihydro-1(2H)-isoquinolone Yield: 17 mg, 83%. MALDI-TOF MS: 412 (MW), 434 (MW+Na+).

EXAMPLE 14 trans-N-(4-butyramidoyl)-3-(4-cyanophenyl)-4-carboxy-3,4-dihydro-1(2H)-isoquinolone Yield: 13 mg, 69%. MALDI-TOF MS: 399 (MW+Na+).

EXAMPLE 15 trans-N-(4-butyramidoyl)-3-(2-bromophenyl)-4-carboxy-3,4-dihydro-1(2H)-isoquinolone Yield: 18 mg, 84%. MALDI-TOF MS: 453 (MW+Na+).

EXAMPLE 16 trans-N-(4-butyramidoyl)-3-(3-hydroxyphenyl)-4-carboxy-3,4-dihydro-1(2H)-isoquinolone Yield: 2 mg, 11%. MALDI-TOF MS: 389 (MW+Na+).

EXAMPLE 17 trans-N-(6-hexanamidoyl)-3-(phenyl)-4-carboxy-3,4-dihydro-1(2H)-isoquinolone

Yield: quantitative. MALDI-TOF MS: 402 (MW+Na+).

EXAMPLE 18 trans-N-(6-hexanamidoyl)-3-(4-methoxyphenyl)-4-carboxy-3,4-dihydro-1(2H)-isoquinolone Yield: 16 mg, 78%. MALDI-TOF MS: 410 (MW), 432 (MW+Na+), 448 (MW+K+).

EXAMPLE 19 trans-N-(6-hexanamidoyl)-3-(3,5-dimethoxyphenyl)-4-carboxy-3,4-dihydro-1(2H)-isoquinolone Yield: 18 mg, 82%. MALDI-TOF MS: 440 (MW), 462 (MW+Na+), 478 (MW+K+).

EXAMPLE 20 trans-N-(6-hexanamidoyl)-3-(4-cyanophenyl)-4-carboxy-3,4-dihydro-1(2H)-isoquinolone Yield: 15 mg, 74%. MALDI-TOF MS: 405 (MW), 427 (MW+Na+).

EXAMPLE 21 trans-N-(6-hexanamidoyl)-3-(2-bromophenyl)-4-carboxy-3,4-dihydro-1(2H)-isoquinolone Yield: 19 mg, 83%. MALDI-TOF MS: 481 (MW+Na+).

EXAMPLE 22 trans -N-(6-hexanamidoyl)-3-(3-hydroxyphenyl)-4-carboxy-3,4-dihydro-1(2H)-isoquinolone Yield: 3 mg, 15%. MALDI-TOF MS: 396 (MW), 418 (MW+Na+).

EXAMPLE 23 trans-N-(2-acetamidoyl)-3-(phenyl)-4-carboxy-3,4-dihydro-1(2H)-isoquinolone

Yield: 11 mg, 68%. MALDI-TOF MS: 324 (MW), 346 (MW+Na+).

EXAMPLE 24 trans-N-(2-acetamidoyl)-3-(4-methoxyphenyl)-4-carboxy-3,4-dihydro-1(2H)-isoquinolone Yield: 9 mg, 51%. MALDI-TOF MS: 376 (MW+Na+).

EXAMPLE 25 trans-N-(2-acetamidoyl)-3-(3,5-dimethoxyphenyl)-4-carboxy-3,4-dihydro-1(2H)-isoquinolone Yield: 9 mg, 47%. MALDI-TOF MS: 406 (MW+Na+).

EXAMPLE 26 trans-N-(2-acetamidoyl)-3-(4-cyanophenyl)-4-carboxy-3,4-dihydro-1(2H)-isoquinolone Yield: 9 mg, 52%. MALDI-TOF MS: 371 (MW+Na+).

EXAMPLE 27 trans-N-(2-acetamidoyl)-3-(2-bromophenyl)-4-carboxy-3,4-dihydro-1(2H)-isoquinolone Yield: quantitative. MALDI-TOF MS: 425 (MW+Na+).

EXAMPLE 28 trans-N-(2-acetamidoyl)-3-(3-hydroxyphenyl)-4-carboxy-3,4-dihydro-1(2H)-isoquinolone Yield: 3 mg, 18%. MALDI-TOF MS: 362 (MW+Na+).

EXAMPLE 29 trans-N-(2-acetamidoyl)-3-methyl-4-carboxy-3,4-dihydro-1(2H)-isoquinolone

This Example provides the solid-phase synthesis of trans-N-(2-acetamidoyl)-3-methyl-4-carboxy-3,4-dihydro-1(2H)-isoquinolone prepared by condensing, on an MBHA resin, glycine, acetaldehyde and homophthalic anhydride. The final product was removed from the resin by HF cleavage.

N-(t-Butyloxycarbonyl)glycine attached to MEHA resin (0.05 mmoles) was sealed in a polypropylene packet. The packet was shaken in 55% (v/v) TFA/DCM (30 ml, 30 min) then washed with DCM (1×30 ml), isopropyl alcohol (2×30 ml), 5% (v/v) DIEA/DCM (3×30 ml, 2 min each), DCM (2×30 ml), and anhydrous DMF (2×30 ml).

A solution of acetaldehyde (5 mmoles) and anhydrous trimethylorthoformate (10 mmoles) was prepared in DMF (10 ml) and added to the packet. After shaking for 3.75 hrs the packet was washed with dry (<0.03% water) DMF (5×30 ml). A solution of homophthalic anhydride (5 mmoles) and triethylamine (0.075 mmoles) was prepared in chloroform (10 ml) and added to the packet. After shaking at room temperature for 17 hrs the packet was washed with DCM (3×30 ml), DMF (3×30 ml), shaken for 20 min in water (30 ml), washed with DMF (3×30 ml) and DCM (3×30 ml).

The isoquinolone was cleaved off of the resin using HF as in Example 3. The residue was dissolved in deuterated DMSO to obtain NMR and mass spectra after which the solvent was removed under reduced pressure providing a 2/1 mixture of the desired product and the amide of homophthalic acid and glycinamide as a clear oil (10 mg, 77w). MALDI-TOF MS: 283 (MW+Na+).

EXAMPLE 30 trans-N-(2-acetamidoyl)-3-cyclohexyl-4-carboxy-3,4-dihydro-1(2H)-isoquinolone

Synthesis was performed as in Example 29 with the exception of substituting cyclohexanecarboxaldehyde for acetaldehyde. Obtained after cleavage was a 2/1 mixture of the desired product and the amide of homophthalic acid and glycinamide as a clear oil (12 mg, 73%). MALDI-TOF MS: 329 (MW), 351 (MW+Na+).

EXAMPLE 31 trans-N-(2-acetamidoyl)-3-(E-2-but-2-enyl)-4-carboxy-3,4-dihydro-1(2H)-isoquinolone Synthesis was performed as in Example 29, excepting substitution of trans-2-methyl-2-butanal for acetaldehyde. Obtained after cleavage was a 2/1 mixture of the desired product and the amide of homophthalic acid and glycinamide as a clear oil (15 mg, 100%). MALDI-TOF MS: 325 (MW+Na+).

EXAMPLE 32 trans-N-(2-acetamidoyl)-3-phenyl-4-(propylcarboxylate)-3,4-dihydro-1(2H)-isoquinolone Trans-N-(2-Acetamidoyl)-3-(3,5-dimethoxyphenyl)-4-carboxy-3,4-dihydro-1(2H)-isoquinolone (0.05 mmoles) was prepared on MBHA polystyrene resin using the method described in Example 4 with the following changes: glycine was substituted for alanine, 3,5-dimethoxybenzaldehyde was substituted for benzaldehyde, and the product was further modified before cleavage off resin.

A solution of [O-(7-azabenzotriazol-1-yl)-1,1,3,3-tetramethyluronium hexafluorophosphate (HATU) in anhydrous DMF (0.93 mmoles, 3.1 ml, 300 mM solution) was added to the packet and shaken for 20 min. The HATU solution was decanted off of the tea-bag and anhydrous DMF (4.7 ml) and anhydrous 1-propanol (0.374 ml, 5 mmoles) were added. After shaking for 1 hr, the propanol solution was removed and the bag washed with anhydrous DMF (2×10 ml). The HATU treatment was repeated followed by decanting and addition of a second 1-propanol solution. This reaction was shaken at room temperature for 66 hrs. The bag was then washed with DMF (4×10 ml), DCM (3×10 ml), and allowed to dry.

Standard HF cleavage as in Example 4 provided a clear oil shown by NMR and mass spectra to contain a half mixture of the desired ester and the free acid (18 mg, 85%) MALDI-TOF MS: 448 (MW+Na+).

EXAMPLE 33 trans-N-(2-acetamidoyl)-3-phenyl-4-(N-(isopropyl)carboxamido)-3,4-dihydro-1(2H)-isoquinolone This product was prepared as in Example 32 but with the substitution of isopropylamine for 1-propanol. Yield: 20 mg, 94%. MALDI-TOF MS: 425 (MW), 447 (MW+Na+).

EXAMPLE 34 trans-N-(2-acetamidoyl)-3-phenyl-4-(N,N-(diethyl)carboxamido)-3,4-dihydro-1(2H)-isoquinolone This product was prepared as in Example 32 but with the substitution of N,N-diethylamine for 1-propanol. Yield: 21 mg, 96%. MALDI-TOF MS: 439 (MW), 461 (MW+Na+).

EXAMPLE 35 trans-N-(2-acetamidoyl)-3-phenyl-4-(N-(4-aminomorpholinyl)carboxamido)-3,4-dihydro-1(2H)-isoquinolone This product was prepared as in Example 32 but with the substitution of 4-aminomorpholine for 1-propanol. Yield: 23 mg, 98%. MALDI-TOF MS: 468 (MW), 490 (MW+Na+).

EXAMPLE 36 trans-N-(2-acetamidoyl)-3-phenyl-4-(N-((±)3-aminoquinuclidyl)carboxamido)-3,4-dihydro-1(2H)-isoquinolone This product was prepared as in Example 32 but with the substitution of (±)-3-aminoquinuclidine, bis HCl salt for 1-propanol; DIEA (200 mole % versus aminoquinuclidine) was also added to neutralize the HCl salt. Yield: 23 mg, 98%. MALDI-TOF MS: 468 (MW), 490 (MW+Na+).

EXAMPLE 37

Solid-phase synthesis of a combinatorial library pool containing isoquinolines derived from five amino acids, benzaldehyde and homophthalic anhydride As described in Example 2, five porous polystyrene packets were prepared each containing TentaGel™ S-NH2 resin (385 mg, 0.100 milliequivalents) derivatized with the protected RINK linker. Following the procedure provided in Example 2, one bag each was then coupled with one each of five different amino acids, N-(9-fluorenylmethoxycarbonyl)-3-aminopropionic acid, N-(9-fluorenylmethoxycarbonyl)-4-aminobutyric acid, N-(9-fluorenylmethoxycarbonyl)-6-aminohexanoic acid, N-(9-fluorenylmethoxycarbonyl)-N-t-butoxycarbonyl-(s)-2,6-diaminohexanoic acid, and N-(9-fluorenylmethoxycarbonyl)-glycine.

The resin packets were dried at room temperature and cut open. The resin inside was pooled from all five bags and the resin was shaken in DCM (20 ml) for 75 min. The resin was filtered off and again dried before being divided into five equal portions and resealed in porous polystyrene packets. One packet was then reacted with first benzaldehyde and then homophthalic anhydride as in Example 5. The resin was cleaved and worked up as in Example 5, providing a clear oil, 11 mg, 61% yield based on average molecular weight). MALDI-TOF MS of the crude products after cleavage showed all five expected isoquinolines for each individual resin packet. Analysis of the final extract by proton NMR and MALDI-TOF MS indicated that only four isoquinolines were now present with the 2,6-(s)-diaminohexanoic acid based isoquinolone having been lost in the extraction procedure.

EXAMPLE 38

Solid-phase synthesis of a combinatorial library pool containing isoquinolines derived from five amino acids, 4-methoxybenzaldehyde and homophthalic anhydride This library pool was synthesized as in Example 37, with the exception of using 4-methoxybenzaldehyde instead of benzaldehyde. Cleavage from the resin was performed on all 100 mmoles of resin and yield and mass spectra were immediately obtained on the residue with no aqueous extraction being performed. Yield: 36 mg, 93%. MALDI-TOF MS of the crude products after cleavage showed all five expected isoquinolines for each individual resin packet.

EXAMPLE 39

Solid-phase synthesis of a combinatorial library pool containing isoquinolines derived from five amino acids, 3,5-dimethoxybenzaldehyde and homophthalic anhydride This library pool was synthesized as in Example 37, with the exception of substituting 3,5-dimethoxybenzaldehyde for benzaldehyde used in Example 37. Cleavage from the resin was performed on all 100 $\mu$moles of resin and yield and mass spectra were immediately obtained on the residue with no aqueous extraction being performed. Yield: 35 mg, 84%. MALDI-TOF MS of the crude products after cleavage showed all five expected isoquinolines for each individual resin packet.

EXAMPLE 40

Solid-phase synthesis of a combinatorial library pool containing isoquinolines derived from five amino acids, 4-cyanobenzaldehyde and homophthalic anhydride This library pool was synthesized as in Example 37, with a substitution of 4-cyanobenzaldehyde for benzaldehyde used in Example 37. Cleavage from the resin was performed on all 100 $\mu$moles of resin and yield and mass spectra were immediately obtained on the residue with no aqueous extraction being performed. Yield: 34 mg, 89%. MALDI-TOF MS of the crude products after cleavage showed all five expected isoquinolines for each individual resin packet.

EXAMPLE 41

Solid-phase synthesis of a combinatorial library pool containing isoquinolines derived from five amino acids, 2-bromobenzaldehyde and homophthalic anhydride This library pool was synthesized as in Example 37, only instead of using benzaldehyde as in that Example, 2-bromobenzaldehyde was used. Cleavage from the resin was performed on all 100 $\mu$moles of resin and yield and mass spectra were immediately obtained on the residue with no aqueous extraction being performed. Yield: 41 mg, 94%. MALDI-TOF MS of the crude products after cleavage showed all five expected isoquinolines for each individual resin packet.

EXAMPLE 42

Solid-phase synthesis of a combinatorial library pool containing isoquinolines derived from five amino acids, 3-hydroxybenzaldehyde and homophthalic anhydride This library pool was also synthesized following the procedures set forth in Example 37, with the exception of substituting 3-hydroxybenzaldehyde for the benzaldehyde. Cleavage from the resin was performed on all 100 $\mu$moles of resin and yield and mass spectra were immediately obtained on the residue with no aqueous extraction being performed. Yield: quantitative. MALDI-TOF MS of the crude products after cleavage showed all five expected isoquinolines for each individual resin packet.

EXAMPLE 43

Solid-phase synthesis of a library of 21,736 different isoquinoline amides and acids Eleven porous polypropylene tea-bags were prepared each containing polystyrene MBHA/resin (974 mg, 0.750 milliequivalents). One tea-bag was placed in a 60 ml bottle and washed with 5% (v/v) DIEA/DCM (3×30 ml) followed by DCM, 5×30 ml. A solution of N-(t-butyloxycarbonyl) glycine (657 mg, 3.75 mmoles), HOBt (507 mg, 3.75 mmoles), and DIC (0.705 ml, 4.5 mmoles) was prepared in DMF (37.5 ml) and added to the resin packet. After shaking for 16 hrs the tea-bag was washed with DMF (3×30 ml) and DCM (3×30 ml). The same coupling procedure was performed on the remaining ten tea-bags, each being reacted with a separate amino acid from the list: N-(t-butyloxycarbonyl)-3-aminopropionic acid, N-(t-butyloxycarbonyl)-5-aminopentanoic acid, N-(t-butyloxycarbonyl)-7-aminoheptanoic acid, (s)-2-N-(t-butyloxycarbonyl)-3-N-(9-fluorenylmethoxycarbonyl)-diaminopropionoic acid, (s)-2-N-(t-butyloxycarbonyl)-6-N-(9-fluorenylmethoxycarbonyl)-diaminohexanoic acid, (s)-(t-butyloxycarbonyl)-2-methyl-3-aminopropionic acid, (r)-(t-butyloxycarbonyl)-2-methyl-3-aminopropionic acid, N-(t-butyloxycarbonyl)-2-(2-aminoethoxyethoxy)acetic acid, N-(t-butyloxycarbonyl)-trans-4-(aminomethyl) cyclohexanecarboxylic acid, N-(t-butyloxycarbonyl)-4-(aminomethyl)benzoic acid. The tea-bags with attached (s)-

2-N-(t-butyloxycarbonyl)-3-N-(9-fluorenylmethoxycarbonyl)-diaminopropionic acid, and (s)-2-N-(t-butyloxycarbonyl)-6-N-(9-fluorenylmethoxycarbonyl)-diaminohexanoic acid were washed with DCM (2×50 ml), shaken twice in 20% (v/v) piperidine/DMF (30 ml, 5 min then 15 min), then washed with DMF (4×50 ml) and DCM (4×50 ml). The remaining nine tea-bags were placed in one bottle and washed with DCM (150 ml, 15 min) and then treated with 55% (v/v) TFA/DCM (150 ml, 30 min). The bags were then washed with DCM (150 ml), isopropyl alcohol (2×150 ml), DCM (2×150 ml), 5% (v/v) DIEA/DCM (3×150 ml, 2 min each) and DCM (3×150 ml). After drying at room temperature the eleven tea-bags were cut open and the contents pooled in a bottle containing DCM (70 ml). The bottle was shaken for 90 min to thoroughly mix the resin. The DCM/resin slurry was then poured into a large (12×18 cm) tea-bag to separate the resin from the DCM and the resin was dried at 50° C. The resulting 11.042 g of resin (8.25 mmoles total of mixed amino acids) was divided into 39 tea-bags containing 38×0.241 g resin (each 180 micromoles total of mixed amino acids) and 1×1.204 g (900 micromoles total of mixed amino acids). Also prepared for use as a control were 38 additional tea-bags each containing 23 mg (18 micromoles) of glycine (containing a free amino group) attached to MBHA resin (coupled and deprotected as in Example 1, subheading 1, hereinafter referred to as the "glycine control tea-bags").

Placed in a 20 ml bottle were one of the small (0.241 g of mixed amino acid resin) tea-bags and one of the control (18 micromoles of glycine) tea-bags. The two tea-bags were treated with a solution of benzaldehyde (0.508 ml, 5 mmoles) and anhydrous trimethylorthoformate (1.094 ml, 10 mmoles) in anhydrous DMF (9 ml). After shaking for 3 hrs the packet was washed with anhydrous DMF (3×8 ml). A solution of homophthalic anhydride (801 mg, 5 mmoles) and triethylamine (0.044 ml, 0.3 mmoles) was prepared in chloroform (10 ml) and added to the tea-bag. After shaking at room temperature for 15.5 hrs the packet was washed with DMF (6×30 ml) and DCM (4×30 ml) and dried at room temperature. The remaining 37 tea-bags of mixed resin were each paired with one glycine control tea-bag and reacted as above in 37 separate reactions with the following aldehydes: 1, 4-benzodioxan-6-carboxaldehyde, 1-methylindole-3-carboxaldehyde, 2,3-difluorobenzaldehyde, 2-bromobenzaldehyde, 2-chloro-5-nitrobenzaldehyde, 2-furaldehyde, 2-imidazolecarboxaldehyde, 2-naphthaldehyde, 2-pyridinecarboxaldehyde, 2-thiophenecarboxaldehyde, 3,4-dichlorobenzaldehyde, 3,5-bis(trifluoromethyl)benzaldehyde, 3,5-dihydroxybenzaldehyde, 3,5-dimethoxybenzaldehyde, 3,5-dimethyl-4-hydroxybenzaldehyde, 3-(4-methoxyphenoxy) benzaldehyde, 3-furaldehyde, 3-hydroxybenzaldehyde, 3-methyl-4-methoxybenzaldehyde, 3-methylbenzaldehyde, 3-nitrobenzaldehyde, 3-pyridinecarboxaldehyde, 3-thiophenecarboxaldehyde, 4-(3-dimethylaminopropoxy) benzaldehyde, 4-(dimethylamino)benzaldehyde, 4-(methylthio)benzaldehyde, 4-(trifluoromethyl) benzaldehyde, 4-biphenylcarboxaldehyde, 4-bromo-2-thiophenecarboxaldehyde, 4-cyanobenzaldehyde, 4-methoxy-1-naphthaldehyde, 4-nitrobenzaldehyde, 4-pyridinecarboxaldehyde,5-(hydroxymethyl)-2-furaldehyde, 5-bromo-4-hydroxy-3-methoxybenzaldehyde, 5-nitro-2-furaldehyde and 6-methyl-2-pyridine-carboxaldehyde. The large tea-bag containing 1.204 g (900 micromoles total of mixed amino acids) of resin was reacted with 3,5-dimethoxybenzaldehyde in the same manner, but on a five times larger scale of all reagents and solvents and with no control tea-bag.

The 38 tea-bags containing mixed amino acid resin (now containing mixed isoquinolines after the anhydride condensation reaction) were cut open and the contents pooled in a bottle containing DCM (70 ml). The bottle was shaken for 75 min to thoroughly mix the resin. The DCM/resin slurry was then poured into a large (12×18 cm) tea-bag to separate the resin from the DCM and the resin was dried at room temperature. The resulting 10.144 g of resin (6.84 mmoles total of mixed isoquinolines) was divided into 52 tea-bags each containing 0.178 g resin (120 micromoles total of mixed isoquinolines). For use as a control the large tea-bag containing 900 micromoles total of mixed amino acid resin (now mixed isoquinolines) was cut open, weighed (1.331 g=900 micromoles) and divided into 52 tea-bags each containing 22 mg (15 micromoles) of resin. Placed in a 20 ml bottle were one of the small (0.178 g of mixed isoquinoline resin) tea-bags and one of the second set of control (15 micromoles of mixed isoquinoline) tea-bags. The two tea-bags were treated with a solution of HATU in anhydrous DMF (2.4 mmoles, 8 ml, 300 mM solution) and shaken for 20 min. The HATU solution was decanted off of the tea-bags and anhydrous DMF (6.9 ml) and cyclopropyl amine (0.52 ml, 7.5 mmoles) were added. After shaking for 1 hr the cyclopropyl amine solution was removed and the bags were washed with anhydrous DMF (2×8 ml). The HATU treatment was repeated followed by decanting and addition of a second cyclopropyl amine solution. This reaction was shaken at room temperature for 24 hrs. The bags were then washed with DMF (3×8 ml), water (8 ml, 60 min), DMF (3×8 ml), DCM (3×8 ml), and allowed to dry.

Fifty of the remaining tea-bags (each 0.178 g resin, 120 micromoles total of mixed isoquinolines) were each paired with one control tea-bag and reacted as above in 50 separate reactions with the following amines isopropylamine, propylamine, ethanolamine, (aminomethyl)cyclopropane, pyrrolidine, diethylamine, 2-methoxyethylamine, cyclopentylamine, piperidine, 3-pyrrolidinol, amylamine, N,N-dimethylethylenediamine, azetidine, furfurylamine, diallylamine, 2-aminothiazole, 1-aminopiperidine, 1-methylpiperazine, 4-aminomorpholine, diethanolamine, 2-(aminomethyl)pyridine, histamine, 1-(2-aminoethyl) pyrrolidine, 1-amino-4-methylpiperazine, tris (hydroxymethyl)aminomethane, 1-aminopyrrolidine, 1-(3-aminopropyl)imidazole, 1-(2-hydroxyethyl)piperazine, (s)-1-amino-2-(methoxymethyl)pyrrolidine, (+)-3-hydroxypiperidine, 1-amino-4-(2-hydroxyethyl)piperazine, trans-2-aminocyclohexanol, tryptamine, 1-adamantanemethylamine, (2-aminoethyl)-trimethylammonium chloride, (s)-O-t-butyl serine t-butyl ester, glycine benzyl ester, (s)-O-benzyl tyrosine benzyl ester, (s)-N'-carbobenzyloxy lysine benzyl ester, (s)-aspartic acid dibenzyl ester, (+)-3-amino-1,2-propanediol, (−)-3-amino-1,2-propanediol, (+)-tetrahydrofurfurylamine, (−)-tetrahydrofurfurylamine, (+)-exo-2-aminonorbornane, (−)-exo-2-aminonorbornane, cis-decahydroquinoline, trans-decahydroquinoline, (+)-3-aminoquinuclidine, (−)-3-aminoquinuclidine. The one remaining tea-bag was left as the free carboxylic acid. Also reacted with isopropyl amine in the same manner but on a 12.5 times larger scale were the 38 glycine control tea-bags.

The above procedures produced 52 tea-bags each containing a mixture of 418 isoquinoline amides or acids for a total library size of 21,736 compounds.

Also prepared as a control for the aldehyde reaction were 38 single compounds from the building blocks: glycine, one of 38 aldehydes and isopropyl amine. As described above, an additional control for the amine reaction was performed resulting in 51 pools of 11 isoquinolines each prepared from the following building blocks: a mixture of the eleven amino acids, 3,5-dimethoxybenzaldehyde and, separately, each of the 51 amines. Each tea-bag prepared was cleaved separately via standard HF procedures with the addition of 0.2 ml anisole to each HF cleavage reaction as a scavenger and dissolved in an appropriate solvent and for testing in a variety of assays. The control tea-bags were cleaved in the same manner and characterized by NMR or mass spectra.

EXAMPLE 44

Biological radioreceptor assay of 21,736 different isoquinoline amides and acids This example describes the identification of individual compounds contained within the synthetic combinatorial library of Example 43 which are selective inhibitors of the $\mu$ and $\kappa$-opioid ligands, [$^3$H]-DAMGO and [$^3$H]-U69,593, respectively and the $\sigma$ receptor ligand, radiolabeled pentazocine. Compounds were identified using the iterative approach and radioreceptor assays as described above.

Initially, libraries prepared according to Example 43, which are subsetted according to the X substituent, each subset having a unique X and every possible combination of $R^1$ and $R^2$, were screened in each of the $\mu$, $\kappa$-opioid and $\sigma$ receptor assays. The subsets, identified by its pool number, and the chemical reagent used to provide the X variables are provided in Table II along with the results of the assays. Therefore, Table II identifies the relative importance of X's contribution to the activity.

TABLE II

| Pool # | X | MU 1/% bound | Kappa 1/% bound | Sigma 1/% bound |
|---|---|---|---|---|
| 257 | Cyclopropylamine | 0.01640 | 0.01674 | 0.02 |
| 258 | Isopropylamine | 0.01254 | 0.01450 | 0.02073 |
| 259 | Propylamine | 0.01147 | 0.01365 | 0.02337 |
| 260 | Ethanolamine | 0.01151 | 0.01290 | 0.02270 |
| 261 | (Aminomethyl)cyclopropane | 0.01322 | 0.01404 | 0.02606 |
| 262 | Pyrrolidine | 0.01172 | 0.01539 | 0.01664 |
| 263 | Diethylamine | 0.01124 | 0.01419 | 0.01606 |
| 264 | 2-Methoxyethylamine | 0.01223 | 0.01464 | 0.01899 |
| 265 | Cyclopentylamine | 0.01416 | 0.03893 | 0.01841 |
| 266 | Piperidine | 0.01250 | 0.01772 | 0.01616 |
| 267 | 3-Pyrrolidinol | 0.01059 | 0.01444 | 0.01716 |
| 268 | Amylamine | 0.02391 | 0.02101 | 0.02851 |
| 269 | N,N-Dimethylethylenediamine | 0.02309 | 0.01593 | 0.02870 |
| 270 | Azetidine | 0.01179 | 0.01481 | 0.02273 |
| 271 | Furfurylamine | 0.02161 | 0.01794 | 0.03440 |
| 272 | Diallylamine | 0.01263 | 0.01692 | 0.02539 |
| 273 | 2-Aminothiazole | 0.01645 | 0.03261 | 0.01971 |
| 274 | 1-Aminopiperidine | 0.01031 | 0.01577 | 0.01751 |
| 275 | 1-Methylpiperazine | 0.01000 | 0.01652 | 0.01508 |
| 276 | 4-Aminomorpholine | 0.01000 | 0.01188 | 0.02046 |
| 277 | Diethanolamine | 0.02391 | 0.01421 | 0.02500 |
| 278 | 2-(Aminomethyl)-pyridine | 0.02034 | 0.01744 | 0.01680 |
| 279 | Histamine | 0.02381 | 0.01591 | 0.02064 |
| 280 | 1-(2-aminoethyl)-pyrrolidine | 0.02606 | 0.01800 | 0.07710 |
| 281 | 1-Amino-4-methylpiperazine | 0.01039 | 0.01497 | 0.01463 |
| 282 | tris(Hydroxymethyl)-aminomethane | 0.01193 | 0.01113 | 0.01808 |
| 283 | 1-Aminopyrrolidine | 0.01080 | 0.01381 | 0.02244 |
| 284 | 1-(3-Aminopropyl)-imidazole | 0.01429 | 0.01258 | 0.01484 |
| 285 | 1-(2-Hydroxyethyl)-piperazine | 0.01096 | 0.01382 | 0.01447 |
| 286 | (S)-1-Amino-2-(methoxymethyl)-pyrrolidine | 0.01081 | 0.01185 | 0.01617 |
| 287 | (+)-3-Hydroxy-piperidine | 0.01000 | 0.01222 | 0.02219 |
| 288 | 1-Amino-4-(2-hydroxyethyl)-piperazine | 0.01153 | 0.01418 | 0.02048 |
| 289 | trans-2-Aminocyclohexanol | 0.01228 | 0.01515 | 0.02217 |
| 290 | Tryptamine | 0.08613 | 0.02747 | 0.04335 |
| 291 | 1-Adamantanemethyl-amine | 0.01730 | 0.03842 | 1.13636 |
| 292 | (2-Aminoethyl)-trimethylammonium | 0.01238 | 0.01511 | 0.02483 |
| 293 | (L)-Serine | 0.01115 | 0.01321 | 0.02116 |
| 294 | Glycine | 0.01113 | 0.01185 | 0.02100 |
| 295 | (L)-Tyrosine | 0.01129 | 0.01226 | 0.01500 |
| 296 | (L)-Lysine | 0.01078 | 0.01160 | 0.01611 |
| 297 | (L)-Aspartic Acid | 0.01171 | 0.01245 | 0.01503 |
| 298 | (+/−)-3-Amino-1,2-propanediol | 0.01228 | 0.01372 | 0.02352 |
| 299 | (+/−)-3-Amino-1,2-propanediol | 0.01237 | 0.02064 | 0.02179 |
| 300 | (+/−)-Tetrahydrofurfurylamine | 0.01383 | 0.02073 | 0.02443 |
| 301 | (+/−)-Tetrahydrofurfurylamine | 0.01394 | 0.02337 | 0.02210 |
| 302 | (+/−)-exo-2-Aminonorbornane | 0.01689 | 0.02270 | 0.03473 |
| 303 | (+/−)-exo-2-Aminonorbornane | 0.01566 | 0.02606 | 0.03446 |
| 304 | ci/trans-Decahydroquinoline | 0.01327 | 0.01664 | 0.02764 |
| 305 | ci/trans-Decahydroquinoline | 0.01254 | 0.01606 | 0.02958 |
| 306 | (+/−)-3-Aminoquinuclidine | 0.01608 | 0.01899 | 0.02530 |
| 307 | (+/−)-3-Aminoquinuclidine | 0.01640 | 0.01841 | 0.02342 |

The results of the screen provide evidence that there is selectivity of certain compounds for one opioid receptor or over another. More importantly, the assays identify certain classes of compounds which are particularly active. For instance, those compounds made from cyclopentylamine for X (pool # 265) are particularly good inhibitors of the [$^3$H]-U69,593 ligand at the $\kappa$-opioid receptor. Compounds made from 1-adamantanemethylamine at the X position (pool # 291) were identified as significant inhibitors of pentazocine ligand at the a receptor.

From these results, additional subsets of compounds, keeping X constant as adamantanemethylamine and varying at $R^2$ and $R^1$, were prepared and screened in the a receptor assay to determine their relative contribution to the compounds' activity. As described below, an additional 418 compounds were prepared, subsetted by varying $R^2$ substituents, and screened, followed by the synthesis of 11 compounds varying only at the $R^1$ position to identify the lead compound.

Solid-phase synthesis of an iterative library of 418 different isoquinoline amides Thirty-eight tea-bags each containing a mixture of 11 amino acids on resin (7 mg, 5 micromoles) were prepared as in Example 43. Each tea-bag was reacted with a single aldehyde from the list: 1,4-benzodioxan-6-carboxaldehyde, 1-methylindole-3-carboxaldehyde, 2,3-difluorobenzaldehyde, 2-bromobenzaldehyde, 2-chloro-5- nitrobenzaldehyde, 2-furaldehyde, 2-imidazolecarboxaldehyde, 2-naphthaldehyde, 2-pyridinecarboxaldehyde, 2-thiophenecarboxaldehyde, 3,4-dichlorobenzaldehyde, 3,5-bis(trifluoromethyl) benzaldehyde, 3,5-dihydroxybenzaldehyde, 3,5-dimethoxybenzaldehyde, 3,5-dimethyl-4-hydroxybenzaldehyde, 3-(4-methoxyphenoxy) benzaldehyde, 3-furaldehyde, 3-hydroxybenzaldehyde, 3-methyl-4-methoxybenzaldehyde, 3-methylbenzaldehyde, 3-nitrobenzaldehyde, 3-pyridinecarboxaldehyde, 3-thiophenecarboxaldehyde, 4-(3-dimethylaminopropoxy) benzaldehyde, 4-(dimethylamino)benzaldehyde, 4-(methylthio)benzaldehyde, 4-(trifluoromethyl) benzaldehyde, 4-biphenylcarboxaldehyde, 4-bromo-2-thiophenecarboxaldehyde, 4-cyanobenzaldehyde, 4-methoxy-1-naphthaldehyde, 4-nitrobenzaldehyde, 4-pyridinecarboxaldehyde, 5-(hydroxymethyl)-2-furaldehyde, 5-bromo-4-hydroxy-3-methoxybenzaldehyde, 5-nitro-2-furaldehyde, 6-methyl-2-pyridinecarboxaldehyde, and benzaldehyde as in Example 43, but scaled down to 80% as much aldehyde, TMOF, and solvent.

The dried tea-bags were all placed in a 60 ml bottle and washed with anhydrous DMF (2×30 ml). Anhydrous DMF (30 ml) was then added to the tea-bags followed by HATU (3.5 g, 9.2 mmoles) and the tea-bags were shaken for 20 min. The HATU solution was next decanted and the tea-bags were washed with anhydrous DMF (1×20 ml). Anhydrous DMF (18.7 ml) was added to the tea-bags followed by 1-adamantanemethylamine (2.0 g, 12 mmoles). After shaking for 1 hour, the tea-bags were washed with anhydrous DMF (2×20 ml) and the HATU and 1-adamantanemethylamine treatments were repeated. After shaking for 16 hrs. the tea-bags were washed with DMF (4×20 ml), water (1×20 ml for 15 min., DMF (4×20 ml), and DCM (4×20 ml). After drying the tea-bags were cleaved as in Example 43, extracted into 1:1 water/acetonitrile, examined by mass spectrometry, and tested in the a receptor assay as described above. Table III provides the results of that assay and evidences that pool # M367, derived from 5-hydroxymethylfuraldehyde, are the most active compounds. It was discovered in the course of identifying the individual compounds that the $R^2$ group resulting from 5-(hyrdoxymethyl)furanaldehhyde, 5-(hydroxymethyl)furan-2-yl, reacted with the anisole scavenger during HF cleavage to yield the Freidel-Crafts alkylation product, 5-(4'-methoxybenzyl)furan-2-yl.

TABLE III

| Pool | R2 | 1/IC50 | IC50 (nM) |
| --- | --- | --- | --- |
| C291 | all mixed | 0.00175 | 573 |
| M250 | 3,5-Dimethoxybenzaldehyde | 0.00065 | 1,534 |
| M334 | 1,4-Benzodioxan-6-carboxaldehyde | 0.00103 | 973 |
| M335 | 1-Methylindole-3-carboxaldehyde | 0.00104 | 963 |
| M336 | 2,3-Difluorobenzaldehyde | 0.00081 | 1,241 |
| M337 | 2-Bromobenzaldehyde | 0.00096 | 1,043 |
| M338 | 2-Chloro-5-nitrobenzaldehyde | 0.00065 | 1,527 |
| M339 | 2-Furaldehyde | 0.00147 | 682 |
| M340 | 2-Imidazolecarboxaldehyde | 0.00065 | 1,541 |
| M341 | 2-Naphthaldehyde | 0.00050 | 2,018 |
| M342 | 2-Pyridinecarboxaldehyde | 0.00063 | 1,579 |
| M343 | 2-Thiophenecarboxaldehyde | 0.00056 | 1,775 |
| M344 | 3,4-Dichlorobenzaldehyde | 0.00098 | 1,016 |
| M345 | 3,5-Bis(trifluoromethyl)benzaldehyde | 0.00094 | 1,063 |
| M346 | 3,5-Dihydroxybenzaldehyde | 0.00091 | 1,095 |
| M347 | 5-Bromo-4-hydroxy-3-methoxybenzaldehyde | 0.00109 | 921 |

TABLE III-continued

| Pool | R2 | 1/IC50 | IC50 (nM) |
| --- | --- | --- | --- |
| M348 | 3,5-Dimethyl-4-hydroxybenzaldehyde | 0.00071 | 1,415 |
| M349 | 3-(4-Methoxyphenoxy)benzaldehyde | 0.00102 | 977 |
| M350 | 3-Furaldehyde | 0.00091 | 1,099 |
| M351 | 3-Hydroxybenzaldehyde | 0.00108 | 926 |
| M352 | 3-Methyl-4-methoxybenzaldehyde | 0.00078 | 1,286 |
| M353 | 3-Methylbenzaldehyde | 0.00073 | 1,366 |
| M354 | 3-Nitrobenzaldehyde | 0.00062 | 1,623 |
| M355 | 3-Pyridinecarboxaldehyde | 0.00063 | 1,575 |
| M356 | 3-Thiophenecarboxaldehyde | 0.00088 | 1,136 |
| M357 | 4-(3-Dimethylaminopropoxy)benzaldehyde | 0.00075 | 1,325 |
| M358 | 4-(Dimethylamino)benzaldehyde | 0.00115 | 869 |
| M359 | 4-(Methylthio)benzaldehyde | 0.00120 | 834 |
| M360 | 4-(Trifluoromethyl)benzaldehyde | 0.00105 | 950 |
| M361 | 4-Biphenylcarboxaldehyde | 0.00091 | 1,096 |
| M362 | 4-Bromo-2-thiophene carboxaldehyde | 0.00093 | 1,071 |
| M363 | 4-Cyanobenzaldehyde | 0.00067 | 1,490 |
| M364 | 4-Methoxy-1-naphthaldehyde | 0.00084 | 1,187 |
| M365 | 4-Nitrobenzaldehyde | 0.00091 | 1,103 |
| M366 | 4-Pyridinecarboxaldehyde | 0.00101 | 995 |
| M367 | 5-(Hydroxymethyl)-2-furaldehyde | 0.00234 | 428 |
| M369 | 5-Nitro-2-furaldehyde | 0.00163 | 613 |
| M370 | 6-Methyl-2-pyridinecarboxaldehyde | 0.00086 | 1,162 |
| M371 | Benzaldehyde | 0.00103 | 969 |

Solid-phase synthesis of an iterative library of 11 different isoquinoline amides Ten tea-bags each containing one amino acid on resin (75 micromoles) were prepared as in Example 43. As identified in Example 43, one amino acid was in a racemic mixture, therefor accounting for 11 different compounds in 10 bags. All of the tea-bags were placed in a 125 ml bottle and washed with anhydrous DMF (1×60 ml). Added to the tea-bags were anhydrous DMF (27 ml), 5-hydroxymethylfurfural (1.893 g, 15 mmoles), and anhydrous TMOF (3.282 ml, 30 mmoles). After shaking for 3.25 hr the tea-bags were washed with anhydrous DMF (3×50 ml) and anhydrous chloroform (1×50 ml). Next added to the tea-bags were anhydrous chloroform (30 ml), homophthalic anhydride (2.432 g, 15 mmoles), and triethylamine (0.133 ml, 1 mmole). After shaking for 15.5 hrs., the tea-bags were washed with DMF (5×50 ml) and DCM (4×50 ml). The tea-bags were next washed with anhydrous DMF (2×50 ml). Added to the tea-bags were anhydrous DMF (48 ml) and HATU (5.47 g, 14.4 mmoles). After shaking for 20 min., the HATU solution was decanted and the tea-bags were washed with anhydrous DMF (1×50 ml). Anhydrous DMF (25 ml) was added to the tea-bags followed by 1-adamantanemethylamine (4.429 g, 25 mmoles). After shaking for 1 hr, the tea-bags were washed with anhydrous DMF (2×50 ml) and the HATU and 1-adamantanemethylamine treatments were repeated. After shaking for 18 hrs. the tea-bags were washed with DMF (4×50 ml), water (1×50 ml for 40 min., DMF (4×50 ml), and DCM (4×50 ml). After drying the tea-bags were cleaved as in Example 43, extracted into 1:1 water/acetonitrile, examined by mass spectrometry, and screened in the σ receptor assay, the results of which are shown in Table IV.

TABLE IV

|   | R1 | IC50 (nM) |
|---|---|---|
| 1 | 7-Aminoheptanoic acid | 56 |
| 2 | trans-4-(Aminomethyl)cyclohexanecarboxylic acid | 68 |
| 3 | (S)-2,4-Diaminopropionic acid | 71 |
| 4 | (R/S)-3-Amino-2-methylpropionic acid | 86 |
| 5 | 2-(2-Aminoethoxy(ethoxy))acetic acid | 117 |
| 6 | 2-Aminoacetic acid | 124 |
| 7 | 4-(Aminomethyl)benzoic acid | 130 |
| 8 | (S)-2,6-Diaminohexanoic acid | 150 |
| 9 | 5-Aminopentanoic acid | 231 |
| 10 | 3-Aminopropionic acid | 355 |

From the results of the iterative approach and these screens as evidenced in Table IV, the most active compound from the library of Example 43 is one for which $R^1$ is 1,6-hexyl, $R^2$ is 5-(4'-methoxybenzyl)-furan-2-yl, $R^3$ through $R^6$ are, independently a hydrogen atom, X is 1-aminomethyladamantanyl, and Y is $C(O)NH_2$.

EXAMPLE 45

Solid-phase synthesis of a library of 20,900 different isoquinoline amides and acids Eleven porous polypropylene tea-bags are prepared each containing polystyrene MBHA/resin (974 mg, 0.750 milliequivalents). One tea-bag is placed in a 60 ml bottle and washed with 5% (v/v) N,N,-diisopropylethylamine/dichloromethane (3×30 ml) followed by dichloromethane (DCM, 5×30 ml). A solution of N-(t-butyloxycarbonyl) glycine (657 mg, 3.75 mmoles), HOBt (507 mg, 3.75 mmoles), and DIC (0.705 ml, 4.5 mmoles) is prepared in DMF (37.5 ml) and added to the resin packet. After shaking for 16 hrs the tea-bag is washed with DMF (3×30 ml) and DCM (3×30 ml). The same coupling procedure is performed on the remaining ten tea-bags, each being reacted with a separate amino acid from the list: N-(t-butyloxycarbonyl)-3-aminopropionic acid, N-(t-butyloxycarbonyl)-5-aminopentanoic acid, N-(t-butyloxycarbonyl)-7-aminoheptanoic acid, (s)-2-N-(t-butyloxycarbonyl)-3-N-(9-fluorenylmethoxycarbonyl)-diaminopropionic acid, (s)-2-N-(t-butyloxycarbonyl)-6-N-(9-fluorenylmethoxycarbonyl)-diaminohexanoic acid, (s)-(t-butyloxycarbonyl)-2-methyl-3-aminopropionic acid, (r)-(t-butyloxycarbonyl)-2-methyl-3-aminopropionic acid, N-(t-butyloxycarbonyl)-2-(2-aminoethoxyethoxy)acetic acid, N-(t-butyloxycarbonyl)-trans-4-(aminomethyl)cyclohexanecarboxylic acid, N-(t-butyloxycarbonyl)-4-(aminomethyl)benzoic acid. The tea-bags with attached (s)-2-N-(t-butyloxycarbonyl)-3-N-(9-fluorenylmethoxycarbonyl)-diaminopropionic acid, and (s)-2-N-(t-butyloxycarbonyl)-6-N-(9-fluorenylmethoxycarbonyl)-diaminohexanoic acid are washed with DCM (2×50 ml), shaken twice in 20% (v/v) piperidine/DMF (30 ml, 5 min then 15 min), then washed with DMF (4×50 ml) and DCM (4×50 ml). The remaining nine tea-bags are placed in one bottle and washed with DCM (150 ml, 15 min) and then treated with 55% (v/v) TFA/DCM (150 ml, 30 min). The bags are then washed with DCM (150 ml), isopropyl alcohol (2×150 ml), DCM (2×150 ml), 5% (v/v) DIEA/DCM (3×150 ml, 2 min each) and DCM (3×150 ml). After drying at room temperature the eleven tea-bags are cut open and the contents pooled in a bottle containing DCM (70 ml). The bottle is shaken for 90 min to thoroughly mix the resin. The DCM/resin slurry is then poured into a large (12×18 cm) tea-bag to separate the resin from the DCM and the resin is dried at 50° C. The resulting 11.042 g of resin (8.25 mmoles total of mixed amino acids) is divided into 39 tea-bags containing 38×0.241 g resin (each 180 micromoles total of mixed amino acids) and 1×1.204 g (900 micromoles total of mixed amino acids). Also prepared for use as a control are 38 additional tea-bags each containing 23 mg (18 micromoles) of glycine (containing a free amino group) attached to MBHA resin (coupled and deprotected as in Example 43).

Placed in a 20 ml bottle are one of the small (0.241 g of mixed amino acid resin) tea-bags and one of the control (18 micromoles of glycine) tea-bags. The two tea-bags are treated with a solution of benzaldehyde (0.508 ml, 5 mmoles) and anhydrous trimethylorthoformate (1.094 ml, 10 mmoles) in anhydrous DMF (9 ml). After shaking for 3 hrs the packet is washed with anhydrous DMF (3×8 ml). A solution of homophthalic anhydride (801 mg, 5 mmoles) and triethylamine (0.044 ml, 0.3 mmoles) is prepared in chloroform (10 ml) and added to the tea-bag. After shaking at room temperature for 15.5 hrs the packet is washed with DMF (6×30 ml) and DCM (4×30 ml) and dried at room temperature. The remaining 37 tea-bags of mixed resin are each paired with one glycine control tea-bag and reacted as in Example 43 in 37 separate reactions with the following aldehydes: 1,4-benzodioxan-6-carboxaldehyde, 1-methylindole-3-carboxaldehyde, 2,3-difluorobenzaldehyde, 2-bromobenzaldehyde, 2-chloro-5-nitrobenzaldehyde, 2-furaldehyde, 2-imidazolecarboxaldehyde, 2-naphthaldehyde, 2-pyridinecarboxaldehyde, 2-thiophenecarboxaldehyde, 3,4-dichlorobenzaldehyde, 3,5-bis(trifluoromethyl) benzaldehyde, 3,5-dihydroxybenzaldehyde, 3,5-dimethoxybenzaldehyde, 3,5-dimethyl-4-hydroxybenzaldehyde, 3-(4-methoxyphenoxy) benzaldehyde, 3-furaldehyde, 3-hydroxybenzaldehyde, 3-methyl-4-methoxybenzaldehyde, 3-methylbenzaldehyde, 3-nitrobenzaldehyde, 3-pyridinecarboxaldehyde, 3-thiophenecarboxaldehyde, 4-(3-dimethylaminopropoxy) benzaldehyde, 4-(dimethylamino)benzaldehyde, 4-(methylthio)benzaldehyde, 4-(trifluoromethyl) benzaldehyde, 4-biphenylcarboxaldehyde, 4-bromo-2-thiophenecarboxaldehyde, 4-cyanobenzaldehyde, 4-methoxy-1-naphthaldehyde, 4-nitrobenzaldehyde, 4-pyridinecarboxaldehyde, 5-(hydroxymethyl)-2-furaldehyde, 5-bromo-4-hydroxy-3-methoxybenzaldehyde, 5-nitro-2-furaldehyde and 6-methyl-2-pyridinecarboxaldehyde. The large tea-bag containing 1.204 g (900 micromoles total of mixed amino acids) of resin is reacted with 3,5-dimethoxybenzaldehyde in the same manner, but on a five times larger scale of all reagents and solvents and with no control tea-bag. The 38 tea-bags containing mixed amino acid resin (now containing mixed isoquinolines after the above reaction) are cut open and the contents pooled in a bottle containing DCM (70 ml). The bottle is shaken for 75 min to thoroughly mix the resin. The DCM/resin slurry is then poured into a large (12×18 cm) tea-bag to separate the resin from the DCM and the resin is dried at room temperature. The resulting 10.144 g of resin (6.84 mmoles total of mixed isoquinolines) is divided into 49 tea-bags each containing 0.178 g resin (120 micromoles total of mixed isoquinolines). For use as a control the large tea-bag containing 900 micromoles total of mixed amino acid resin (now mixed isoquinolines) is cut open, weighed (1.331 g=900 micromoles) and divided into 50 tea-bags each containing 22 mg (15 micromoles) of resin. Placed in a 20 ml bottle are one of the small (0.178 g of mixed isoquinoline resin) tea-bags and one of the second set of control (15 micromoles of mixed isoquinoline) tea-bags. The two tea-bags are treated with a solution of HATU in anhydrous DMF (2.4 mmoles, 8 ml, 300 mM solution) and shaken for 20 min. The HATU solution is decanted off of the tea-bags and anhydrous DMF (6.9 ml) and aniline (0.683 ml, 7.5 mmoles) are added. After shaking for 1 hr the aniline solution is removed and the bags are washed with anhydrous DMF (2×8 ml). The HATU treatment is repeated followed by decanting and addition of a second aniline solution. This reaction is shaken at room temperature for 24 hrs. The bags are then washed with DMF (3×8 ml), water (8 ml, 60 min), DMF (3×8 ml), DCM (3×8 ml), and allowed to dry. Forty eight of the remaining tea-bags (each 0.178 g resin, 120 micromoles total of mixed isoquinolines) are each paired with one control tea-bag and reacted as in Example 43 in 48 separate reactions with the following amines : 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-methoxyaniline, 3-methoxyaniline, 4-methoxyaniline, 2-hydroxyaniline, 3-hydroxyaniline, 4-hydroxyaniline, 2-carboethoxyaniline, 3-carboethoxyaniline, 4-carboethoxyaniline, 2-trifluoromethylaniline, 3-trifluoromethylaniline, 4-trifluoromethylaniline, 2-dimethylaminoaniline, 3-dimethylaminoaniline, 4-dimethylaminoaniline, 2-phenoxyaniline, 3-phenoxyaniline, 4-phenoxyaniline, 3,4-methylenedioxyaniline, 2,3-methylenedioxyaniline, 2,3-difluoroaniline, 3,4-difluoroaniline, 2,3-dichloroaniline, 3,4-dichloroaniline, 2,3-dibromoaniline, 3,4-dibromoaniline, 2,3-dimethoxyaniline, 3,4-dimethoxyaniline, 1-amino-5,6,7,8-tetrahydronaphthalelene, 2-hydroxy-3-amino-5,6,7,8-tetrahydronaphthalelene, 2-aminonaphthalene, 1-amino-4-chloronaphthalene, 1-amino-4-bromonaphthalene, 5-amino-1-hydroxynaphthalene, 1-amino-2-hydroxynaphthalene, 5-aminoindane, 1-aminofluorene, 2-aminofluorine, N-methylaniline. The remaining tea-bag is left as the free carboxylic acid. Also reacted with aniline in the same manner but on a 12.5 times larger scale are the 38 glycine control tea-bags as in Example 43. The above procedures produced 50 tea-bags each containing a mixture of 418 isoquinoline amides or acids for a total library size of 20900 compounds.

Also prepared as a control for the aldehyde reaction are 38 single compounds from the building blocks: glycine, one of 38 aldehydes and aniline. An additional control for the amine reaction is performed resulting in 49 pools of 11 isoquinolines each prepared from the following building blocks: a mixture of the eleven amino acids, 3,5-dimethoxybenzaldehyde and, separately, each of the 49 amines. Each tea-bag prepared is cleaved separately via standard HF procedures (Example 3), dissolved in an appropriate solvent and tested in a variety of assays. The control tea-bags are cleaved in the same manner and characterized by NMR or mass spectra.

EXAMPLE 46

Solid-phase synthesis of a library of 459,000 different isoguinoline amides and acids This example describes an expanded library compared to that provided in Example 43, having even more possibilities at $R^1$, $R^2$ and X positions.

Seventy-two porous polypropylene tea-bags were prepared each containing polystyrene MEHA/resin (1.111 g, 1.0 milliequivalents). Six tea-bags were placed in a 500 ml bottle. A solution of N-(t-butyloxycarbonyl)-3-aminopropionic acid (beta alanine) (6.237 g, 33 mmoles), HOBt (4.458 g, 33 mmoles), and DIC (6.2 ml, 39.6 mmoles) was prepared in DMF (275 ml) and added to the resin packet. After shaking for 22 hrs N,N-dimethylaminopyridine (164 mg, 1.3 mmoles) was added and the solution shaken for an additional 18 hrs. The tea-bags were then washed with DMF (3×300 ml) and DCM (3×300 ml). The same coupling procedure was performed on the remaining 66 tea-bags in groups of six at a time, each six being reacted with a separate amino acid from the list: N-(t-butyloxycarbonyl)glycine, N-(t-butyloxycarbonyl)-5-aminopentanoic acid, N-(t-butyloxycarbonyl)-7-aminoheptanoic acid, (s)-2-N-(t-butyloxycarbonyl)-3-N-(9-fluorenylmethoxycarbonyl)-diaminopropionic acid, (s)-2-N-(t-butyloxycarbonyl)-6-N-(9-fluorenylmethoxycarbonyl)-diaminohexanoic acid, (s)-(t-butyloxycarbonyl)-2-methyl-3-aminopropionic acid, (r)-(t-butyloxycarbonyl)-2-methyl-3-aminopropionic acid, N-(t-butyloxycarbon(aminomethyl) cyclohe(aminomethyl)cyclohexanecarboxylic acid, N-(t-butyloxycarbonyl)-4-(aminomethyl)benzoic acid, (t-butyloxycarbonyl)-6-aminohexanoic acid, and (t-butyloxycarbonyl)-4-aminobutyric acid.

An additional 36 tea-bags, each containing 1.111 g of MBHA resin (1.0 mmole) were also prepared. Eighteen of these bags were added to a preformed solution of 4-(bromomethyl)phenylacetic acid (20.61 g, 90 mmoles) and DIC (4.29 ml, 108 mmoles) in DMF (200 ml) and shaken at room temperature for 16 hrs. Eighteen additional bags were coupled identically, but to bromoacetic acid. After 16 hrs the two sets of tea-bags were each washed with DMF (3×300 ml) and DCM (3×300 ml) and allowed to dry at room temperature. Six bags of bromoacetic acid on resin were paired with six bags of 4-(bromomethyl)phenylacetic acid on resin and added to a preformed solution of the HCl salt of 2-aminoethanethiol (19.88 g, 175 mmoles) in DMF (200 ml). After shaking 116 hrs DIEA (33.53 ml, 193 mmoles) was added and the bags shaken an additional 126 hrs. Identical conditions were used for the attachment of two other nucleophiles (1-amino-2-methyl-2-propanethiol and delta-Boc-ornithine methyl ester) to the bromoalkyl derivatized resins. Cleavage of a small aliquot of each and characterization by NMR and mass spectroscopy showed that the expected amino-derivatized resin had formed in 5 of the 6 examples. The reaction between bromoacetic-derivatized resin and the Boc-ornithine nucleophile provided only low yields of product; these tea-bags were therefore discarded. The 30 tea-bags resulting from the five successful reactions were used for further synthesis as described below.

The tea-bags with attached (s)-2-N-(t-butyloxycarbonyl)-3-N-(9-fluorenylmethoxycarbonyl)-diaminopropionic acid, and (s)-2-N-(t-butyloxycarbonyl)-6-N-(9-fluorenylmethoxycarbonyl)-diaminohexanoic acid were washed with DCM (2×300 ml), shaken twice in 20% (v/v) piperidine/DMF (300 ml, 5 min then 15 min), then washed with DMF (4×300 ml) and DCM (4×300 ml).

The 24 tea-bags containing amino-derivatized resin prepared from the two thiol nucleophiles required no deprotection. All of the remaining 66 tea-bags carried Boc-protected derivatives on resin and were therefore deprotected. These tea-bags were placed in two bottles, each of which was treated identically as follows. Each set of bags were first washed with DCM (900 ml, 15 min) and then treated with 55% (v/v) TFA/DCM (900 ml, 30 min). The bags were then washed with DCM (900 ml for each set), isopropyl alcohol (2×900 ml for each set), DCM (2×900 ml for each set), 5% (v/v) DIEA/DCM (3×900 ml, 2 min each set) and DCM (3×900 ml for each set).

After drying at room temperature all 102 of the tea-bags were cut open and 5.85 mmoles of each acid attached to resin was pooled in a bottle containing DCM (600 ml). The bottle was shaken for 180 min to thoroughly mix the resin. The DCM/resin slurry was then poured into two large (12×18 cm) tea-bag to separate the resin from the DCM and the resin was dried at room temperature. The resulting 121.6 g of resin (99.45 mmoles of mixed amino acids) was divided into 90 tea-bags each containing 0.673 g resin (each 550 micromoles total of mixed amino acids). An additional identical 90 bags were prepared for use in later iterational deconvolution. Also prepared for use as a control were 90 additional tea-bags each containing 49 mg (45 micromoles) of glycine (containing a free amino group) attached to MBHA resin (coupled and deprotected as described previously in this example).

Placed in a 60 ml bottle were one of the library (0.673 g, 550 μmoles of mixed amino acid resin) tea-bags and one of the control (45 micromoles of glycine) tea-bags. The two tea-bags were treated with a solution of benzaldehyde (2.135 ml, 21 mmoles) and anhydrous trimethylorthoformate (4.6 ml, 42 mmoles) in anhydrous DMF (38 ml). After shaking for 4 hrs the packets were washed with anhydrous DMF (3×20 ml) and anhydrous chloroform (1×20 ml). A solution of homophthalic anhydride (2.4 g, 15 mmoles) and triethylamine (0.132 ml, 0.9 mmoles) was prepared in chloroform (30 ml) and added to the tea-bag. After shaking at room temperature for 16 hrs the packets were washed with DMF (4×30 ml) followed by DCM (3×30 ml) and dried at room temperature. The remaining 89 tea-bags of mixed resin were each paired with one glycine control tea-bag and reacted as described for benzaldehyde in 89 separate reactions with the following aldehydes: 2-bromobenzaldehyde, 2-cyanobenzaldehyde, 2-fluorobenzaldehyde, 2-hydroxybenzaldehyde(salicylaldehyde), 2-methoxybenzaldehyde(o-anisaldehyde), 3-bromobenzaldehyde, 3-carboxybenzaldehyde, 3-cyanobenzaldehyde, 3-fluorobenzaldehyde, 3-hydroxybenzaldehyde, 3-methoxybenzaldehyde(m-anisaldehyde), 3-methylbenzaldehyde(m-tolualdehyde), 3-nitrobenzaldehyde, 3-(trifluoromethyl)benzaldehyde, 4-acetamidobenzaldehyde, 4-bromobenzaldehyde, 4-carboxybenzaldehyde, 4-cyanobenzaldehyde, 4-(3-dimethylaminopropoxy)benzaldehyde, 4-fluorobenzaldehyde, 4-(dimethylamino)benzaldehyde, 4-hydroxybenzaldehyde, 4-isopropylbenzaldehyde, 4-methoxybenzaldehyde(p-anisaldehyde), 4-methylbenzaldehyde(p-tolualdehyde), 4-(methylcarboxylate)benzaldehyde, 4-methylsulphonylbenzaldehyde, 4-(methylthio)benzaldehyde, 4-nitrobenzaldehyde, 4-propoxybenzaldehyde, 4-(trifluoromethyl)benzaldehyde, 3,5-bis(trifluoromethyl)benzaldehyde, 3,5-dimethoxybenzaldehyde, 3,5-dibenzyloxybenzaldehyde, 3,5-dichlorobenzaldehyde, 2,3-difluorobenzaldehyde, 2,4-dichlorobenzaldehyde, 2-chloro-5-nitrobenzaldehyde, 2-chloro-6-fluorobenzaldehyde, 2,6-difluorobenzaldehyde, 3-bromo-4-fluorobenzaldehyde, 3,4-dibenzyloxybenzaldehyde, 3,4-dichlorobenzaldehyde, 3,4-difluorobenzaldehyde, 3-fluoro-4-methoxybenzaldehyde, 3-nitro-4-chlorobenzaldehyde, 3-hydroxy-4-methoxybenzaldehyde, 3-hydroxy-4-nitrobenzaldehyde, 4-methoxy-3-(sulfonic acid sodium salt)benzaldehyde, 3-methyl-4-methoxybenzaldehyde, 2,3,4-trifluorobenzaldehyde, 2,3,5-trichlorobenzaldehyde, 3,5-dimethyl-4-hydroxybenzaldehyde, 3-methoxy-4-hydroxy-5-bromobenzaldehyde, 3-methoxy-4-hydroxy-5-nitrobenzaldehyde, 1,4-benzodioxan-6-carboxaldehyde, 2,3-(methylenedioxy)benzaldehyde, 3,4-(methylenedioxy)benzaldehyde, 3,4-(methylenedioxy)-6-nitrobenzaldehyde, 9-formyl-8-hydroxyjulolidine, 3-(3,4-dichlorophenoxy)benzaldehyde, 3-(4-methoxyphenoxy)benzaldehyde, 3-phenoxybenzaldehyde, 4-phenoxybenzaldehyde, 4-biphenylcarboxaldehyde, 1-napthaldehyde, 2-naphthaldehyde, 4-methoxy-1-naphthaldehyde, 2-quinolinecarboxaldehyde, 3-quinolinecarboxaldehyde, 4-quinolinecarboxaldehyde, 8-hydroxyquinoline-2-carboxaldehyde, 9-ethyl-3-carbazolecarboxaldehyde, 2-thiophenecarboxaldehyde, 3-thiophenecarboxaldehyde, 5-methyl-2-thiophenecarboxaldehyde, 2-furaldehyde, 3-furaldehyde, 5-methyl-2-furaldehyde, 2-pyridinecarboxaldehyde, 3-pyridinecarboxaldehyde, 4-pyridinecarboxaldehyde, 6-methyl-2-pyridinecarboxaldehyde, pyrrole-2-carboxaldehyde, 1-methyl-2-pyrrolecarboxaldehyde, 2-imidazolecarboxaldehyde, 2-thiazolecarboxaldehyde, 5-(hydroxymethyl)-2-furaldehyde, and 5-nitro-2-furaldehyde.

Twelve additional tea-bags each containing 1 mmole of glycine on MBHA resin (prepared as described previously in this example) was reacted with benzaldehyde in the same manner, but on a ten times larger scale of all reagents and solvents and with no control tea-bag. The 90 tea-bags containing mixed amino acid resin (now containing mixed isoquinolines after the above reaction) were cut open and the contents pooled in a bottle containing DCM (400 ml). The bottle was shaken for 70 min to thoroughly mix the resin. The DCM/resin slurry was then poured into a large (45×23 cm) tea-bag to separate the resin from the DCM and the resin was dried at room temperature. The resulting 76.58 g of resin (49.5 mmoles total of mixed isoquinolines) was divided into 160 tea-bags each containing 0.154 g resin (100 micromoles each of mixed isoquinolines) and 160 tea-bags each containing 0.309 g resin (200 micromoles each of mixed isoquinolines) for use in preparation of a reduced library (Example 50).

For use as controls the twelve tea-bags containing a total of 12 mmoles of the isoquinoline prepared from glycine, homophthalic anhydride and benzaldehyde were cut open, weighed (total 17.17 g=12 mmoles) and divided into 160 tea-bags each containing 72 mg (50 micromoles) of resin (35 tea-bags each containing 144 mg (100 micromoles) of resin were also prepared for use as controls in the reduced library synthesis (Example 50).

Placed in a 20 ml bottle were one of the library (154 mg, 100 μmoles of mixed isoquinoline resin) tea-bags and one of the second set of control tea-bags containing 72 mg of the isoquinoline prepared from glycine, homophthalic anhydride and benzaldehyde. The two tea-bags were treated with a solution of HATU in anhydrous DMF (6 mmoles, 20 ml, 300 mM solution) and shaken for 20 min. The HATU solution was decanted off of the tea-bags and anhydrous DMF (20 ml) and aniline (1.823 ml, 20 mmoles) were added. After shaking for 1 hr the aniline solution was removed and the bags were washed with anhydrous DMF (2×20 ml). The HATU treatment was repeated followed by decanting and addition of a second aniline solution as before. This reaction was shaken at room temperature for 14 hrs. The bags were then washed with DMF (4×20 ml), water (20 ml, 2×20 min), DMF (4×20 ml), DCM (4×20 ml), and allowed to dry at room temperature. One hundred forty-two of the remaining tea-bags (each 154 mg resin, 100 micromoles total of mixed isoquinolines) were each paired with one control tea-bag and reacted as described above for aniline in 148 separate reactions with the following amines : 2-fluoroaniline, 2-methoxyaniline(o-anisidine), 2-(methylmercapto)aniline, benzylamine, 2-methylbenzylamine, 2-chlorobenzylamine, 2-methoxybenzylamine, 2-trifluoromethylbenzylamine, 3-fluoroaniline, 3-trifluoromethylaniline(3-aminobenzotrifluoride), 3-methoxyaniline(m-anisidine), 3-(methylmercapto)aniline, 3-trifluoromethylbenzylamine, 3-methylbenzylamine, 3-fluorobenzylamine, 4-fluoroaniline, 4-methylaniline(p-toluidine), 4-propylaniline, 4-pentylaniline, 4-(methylmercapto) aniline, 4-fluorobenzylamine, 4-chlorobenzylamine, 4-methoxybenzylamine, 4-methylbenzylamine, 3-(1-hydroxyethyl)aniline, 4-bromoaniline, 4-chloroaniline, 2,3-dimethylaniline, 4-methoxyaniline(p-anisidine), 4-carboxamidoaniline(4-aminobenzamide), 2,4-difluoroaniline, 4-bromo-2-methylaniline, 2,5-dimethoxyaniline, 2-methoxy-5-methylaniline, 2-methoxy-5-nitroaniline, 3,4,5-trimethoxyaniline, 3-chloro-4-fluoroaniline, 3-bromo-4-methylaniline, 4-bromo-3-methylaniline, 3,4-dimethoxyaniline(4-aminoveratrole), 3,4-dimethylaniline, 3,5-dimethoxyaniline, 2-methylaniline (o-toluidine), 3-ethoxyaniline (m-phenetidine), 3,4-difluorobenzylamine, 3,4-dimethoxybenzylamine (veratrylamine), 3,4-dichlorobenzylamine, 3,4,5-trimethoxybenzylamine, phenethylamine, 2-(2-chlorophenyl)ethylamine, 2-(3-chlorophenyl)ethylamine, 2-(4-chlorophenyl)ethylamine, 4-methoxyphenethylamine, 3,4-dimethoxyphenethylamine, N-benzylmethylamine, N-benzylethanolamine, aminodiphenylmethane, 1,2,3,4-tetrahydroisoquinoline, 1-phenylpiperazine, 1-(α,α,α-trifluoro-m-tolyl)piperazine, 1,4-benzodioxan-6-amine, 4-(aminomethyl)pyridine, 3-(aminomethyl)pyridine, 1-(2-pyridyl)piperazine, cycloheptylamine, cyclohexylamine, 2-bromo-4-methylaniline, 5-fluoro-2-methylaniline, 3-carboxamidoaniline(3-aminobenzamide), 1-methyl-3-phenylpropylamine, 1-adamantanemethylamine, 1,3,3-trimethyl-6-azabicyclo[3.2.1]octane, 2-ethoxyaniline(o-phenetidine), 4-isopropylaniline, 3-phenyl-1-propylamine, trans-2-phenylcyclopropylamine, 3-nitrobenzylamine, 4-bromobenzylamine, 2-bromobenzylamine, 3-bromobenzylamine, 4-ethoxyaniline(p-phenetidine), 2-aminoindan, 3-amino-2,6-dimethoxypyridine, 4-nitrobenzylamine, 4-benzyloxyaniline, 5-bromo-2-fluorobenzylamine, 6,7-dimethoxy-1,2,3,4-tetrahydroisoquinoline, 2,4-dimethoxybenzylamine, 3-methylsulphonylaniline, 4-(dimethylamino)benzylamine, 4-(dimethylamino)aniline(N,N-dimethyl-1,4-phenylenediamine), pyridoxamine, 2-fluorophenethylamine, 3-fluorophenethylamine, 4-fluorophenethylamine, 2,4-dichlorophenethylamine, 3-iodoaniline, 3-chloro-2-methylaniline, 5-chloro-2-methoxyaniline(5-chloro-o-anisidine), 2-chloro-4-fluoroaniline, 4-methoxy-2-methylaniline, 2,4-dimethoxyaniline, 2,5-dimethylaniline, 2-fluoro-5-methylaniline, 3,5-dimethylaniline, 2,3-dimethoxybenzylamine, 2,4-difluorobenzylamine, 2,5-difluorobenzylamine, 2,6-difluorobenzylamine, 5-chloro-2-methylaniline, 2,4-dimethylaniline, 2-fluoro-4-methylaniline, 4-(diethylamino)aniline(N,N-diethyl-1,4-phenylenediamine), cytosine, 2-aminobenzothiazole, 2-amino-6-fluorobenzothiazole, 2-amino-6-methoxybenzothiazole, 2-(4-aminophenyl)-6-methylbenzothiazole, 3-phenoxyaniline, 4-phenoxyaniline, 1-amino-4-bromonaphthalene, 2-aminofluorene, 1-naphthalenemethylamine, 3-benzyloxyaniline, 4-aminopyridine, 2-amino-4-picoline, 5-aminoindan, 1-amino-5,6,7,8-tetrahydronaphthalene, tyramine, 2-amino-1-phenylethanol, 1-adamantanamine, tryptamine, 2-aminothiazole, 2-iodoaniline, 4-iodoaniline, 2-chloro-5-methylaniline, 4-hydroxy-4-phenylpiperidine, 4-chloro-2-methoxy-5-methylaniline, 4-morpholinoaniline, 3-chloro-4-methoxyaniline(3-chloro-p-anisidine). Four additional library tea-bags were each paired with a control tea-bag and each coupled as above, but to a racemic mixture of two amines from the following list: (±)-alpha-methylbenzylamine, (±)-exo-2-aminonorbornane, (±)-alpha-(methylaminomethyl)benzyl alcohol and (±)-endo-2-aminonorbornane. One additional library tea-bag was left as the free carboxylic acid.

Reacted with p-toluidine in the same manner but on a 40.5 times larger scale were the 90 glycine control tea-bags (45 micromoles each of the isoquinoline formed from glycine and, separately, each of the 90 aldehydes used for imine formation). The above procedures produced 142 tea-bags each containing a mixture of 3060 isoquinoline amides or acids plus 4 tea-bags each containing a mixture of 6120 isoquinoline amides for a total library size of 459,000 compounds.

Each tea-bag prepared was cleaved separately via standard HF procedures (Example 3 with the modification of an addition of 0.2 ml anisole to each HF cleavage reaction as a scavenger), extracted into 45:45:10 water/acetonitrile/acetic acid, examined by HPLC coupled with mass spectrometry, and tested in a variety of assays. The control tea-bags were cleaved in the same manner and characterized by NMR or HPLC and mass spectra.

EXAMPLE 47

Biological radioreceptor assay of 459,000 different isoquinoline amides and acids This example describes an initial screen of libraries prepared according to Example 46 in the δ-opioid receptor assay and the a receptor assay described above. The results of those screens are provided in ensuing Tables V and VI.

TABLE V

| Pool # | X | Percent Bound |
|---|---|---|
| 95 | Pyridoxamine | 0.4 |
| 93 | 4-(Dimethylamino)benzylamine | 2 |
| 103 | 2-Chloro-4-fluoroaniline | 4 |
| 65 | 3-(Aminomethyl)pyridine | 5 |
| 94 | 4-(Dimethylamino)aniline (N,N-dimethyl-1,4-phenylenediamine) | 5 |
| 73 | 1-Adamantanemethylamine | 5 |
| 76 | 4-Isopropylaniline | 5 |
| 49 | 3,4-Dichlorobenzylamine | 5 |
| 58 | N-Benzylethanolamine | 5 |
| 62 | 1-(α,α,α-Trifluro-m-tolyl)piperazine | 6 |
| 87 | 4-Nitrobenzylamine | 6 |
| 132 | 5-Aminoindan | 6 |
| 68 | Cyclohexylamine | 6 |
| 66 | 1-(2-Pyridyl)piperazine | 6 |
| 55 | 4-Methoxyphenethylamine | 6 |
| 127 | 1-Naphthalenemethylamine | 7 |
| 91 | 2,4-Dimethoxybenzylamine | 7 |
| 116 | (+/−)-exo-2-Aminonorbornane | 7 |
| 52 | 2-(2-Chlorophenyl)ethylamine | 7 |
| 135 | 2-Amino-1-phenylethanol | 7 |
| 63 | 1,4-Benzodioxan-6-amine | 7 |
| 89 | 5-Bromo-2-fluorobenzylamine | 7 |
| 64 | 4-(Aminomethyl)pyridine | 7 |
| 61 | 1-Phenylpiperazine | 7 |
| 126 | 2-Aminofluorene | 8 |
| 48 | 3,4-Dimethoxybenzylamine | 8 |

TABLE V-continued

| Pool # | X | Percent Bound |
|---|---|---|
|  | (veratrylamine) |  |
| 54 | 2-(4-Chlorophenyl)ethylamine | 8 |
| 59 | Aminodiphenylmethane | 8 |
| 51 | Phenethylamine | 8 |
| 57 | N-Benzylmethylamine | 8 |
| 140 | 4-Iodoaniline | 8 |
| 79 | 3-Nitrobenzylamine | 8 |
| 81 | (+/−)-endo-2-Aminonorbornane | 8 |
| 53 | 2-(3-Chlorophenyl)ethylamine | 8 |
| 77 | 3-Phenyl-1-propylamine | 8 |
| 108 | 3,5-Dimethylaniline | 9 |
| 60 | 1,2,3,4-Tetrahydroisoquinoline | 9 |
| 74 | 1,3,3-Trimethyl-6-azabicyclo[3.2.1] octane | 9 |
| 141 | 2-Chloro-5-methylaniline | 9 |
| 145 | 3-Chloro-4-methoxyaniline (3-chloro-p-anisidine) | 9 |
| 142 | 4-Hydroxy-4-phenylpiperidine | 10 |
| 70 | 5-Fluoro-2-methylaniline | 10 |
| 124 | 4-Phenoxyaniline | 10 |
| 137 | Tryptamine | 10 |
| 67 | Cycloheptylamine | 10 |
| 110 | 2,4-Difluorobenzylamine | 10 |
| 107 | 2-Fluoro-5-methylaniline | 10 |
| 47 | 3,4-Difluorobenzylamine | 10 |
| 72 | 1-Methyl-3-phenylpropylamine | 10 |
| 99 | 2,4-Dichlorophenethylamine | 10 |
| 85 | 2-Aminoindan | 10 |
| 50 | 3,4,5-Trimethoxybenzylamine | 10 |
| 82 | 2-Bromobenzylamine | 11 |
| 69 | 2-Bromo-4-methylaniline | 11 |
| 78 | trans-2-Phenylcyclopropylamine | 11 |
| 86 | 3-Amino-2,6-dimethoxypyridine | 11 |
| 102 | 5-Chloro-2-methoxyaniline (5-chloro-o-anisidine) | 12 |
| 139 | 2-Iodoaniline | 12 |
| 109 | 2,3-Dimethoxybenzylamine | 12 |
| 112 | 2,6-Difluorobenzylamine | 12 |
| 105 | 2,4-Dimethoxyaniline | 12 |
| 143 | 4-Chloro-2-methoxy-5-methylaniline | 12 |
| 125 | 1-Amino-4-bromonaphthalene | 12 |
| 14 | 3-Trifluoromethylbenzylamine | 13 |
| 101 | 3-Chloro-2-methylaniline | 13 |
| 71 | 3-Carboxamidoaniline (3-aminobenzamide) | 13 |
| 96 | 2-Fluorophenethylamine | 13 |
| 83 | 3-Bromobenzylamine | 14 |
| 100 | 3-Iodoaniline | 15 |
| 123 | 3-Phenoxyaniline | 15 |
| 56 | 3,4-Dimethoxyphenethylamine | 15 |
| 144 | 4-Morpholinoaniline | 16 |
| 75 | 2-Ethoxyaniline(o-phenetidine) | 16 |
| 134 | Tyramine | 16 |
| 9 | 2-Trifluoromethylbenzylamine | 16 |
| 80 | 4-Bromobenzylamine | 16 |
| 20 | 4-Pentylaniline | 17 |
| 90 | 6,7-Dimethoxy-1,2,3,4-Tetrahydroisoquinoline | 17 |
| 26 | 3-(1-Hydroxyethyl)aniline | 18 |
| 136 | 1-Adamantanamine | 18 |
| 138 | 2-Aminothiazole | 18 |
| 129 | 3-Benzyloxyaniline | 19 |
| 122 | 2-(4-Aminophenyl)-6-methylbenzothiazole | 19 |
| 92 | 3-Methylsulphonylaniline | 19 |
| 19 | 4-Propylaniline | 19 |
| 115 | 2-Fluoro-4-methylaniline | 22 |
| 23 | 4-Chlorobenzylamine | 22 |
| 16 | 3-Fluorobenzylamine | 22 |
| 40 | 4-Bromo-3-methylaniline | 22 |
| 128 | (±) - a-(Methylaminomethyl)benzyl alcohol | 22 |
| 133 | 1-Amino-5,6,7,8-tetrahydronapthalene | 23 |
| 15 | 3-Methylbenzylamine | 24 |
| 21 | 4-(Methylmercapto)aniline | 24 |
| 113 | 5-Chloro-2-methylaniline | 25 |
| 117 | 4-(Diethylamino)aniline (N,N-diethyl-1,4-phenylenediamine) | 25 |
| 44 | (±)-α-Methylbenzylamine | 26 |
| 7 | 2-Chlorobenzylamine | 26 |
| 22 | 4-Fluorobenzylamine | 27 |
| 8 | 2-Methoxybenzylamine | 27 |
| 6 | 2-Methylbenzylamine | 27 |
| 39 | 3-Bromo-4-methylaniline | 27 |
| 98 | 4-Fluorophenethylamine | 28 |
| 84 | 4-Ethoxyaniline (p-phenetidine) | 29 |
| 111 | 2,5-Difluorobenzylamine | 29 |
| 29 | 2,3-Dimethylaniline | 29 |
| 5 | Benzylamine | 29 |
| 130 | 4-Aminopyridine | 30 |
| 28 | 4-Chloroaniline | 30 |
| 97 | 3-Fluorophenethylamine | 30 |
| 27 | 4-Bromoaniline | 30 |
| 88 | 4-Benzyloxyaniline | 30 |
| 33 | 4-Bromo-2-methylaniline | 30 |
| 119 | 2-Aminobenzothiazole | 31 |
| 121 | 2-Amino-6-methoxybenzothiazole | 32 |
| 25 | 4-Methylbenzylamine | 32 |
| 114 | 2,4-Dimethylaniline | 32 |
| 120 | 2-Amino-6-fluorobenzothiazole | 32 |
| 13 | 3-(Methylmercapto)aniline | 33 |
| 45 | 2-Methylaniline (o-toluidine) | 34 |
| 131 | 2-Amino-4-picoline | 34 |
| 38 | 3-Chloro-4-fluoroaniline | 36 |
| 17 | 4-Fluoroaniline | 37 |
| 24 | 4-Methoxybenzylamine | 38 |
| 46 | 3-Ethoxyaniline (m-phenetidine) | 38 |
| 104 | 4-Methoxy-2-methylaniline | 38 |
| 18 | 4-Methylaniline (p-toluidine) | 39 |
| 106 | 2,5-Dimethylaniline | 39 |
| 3 | 2-Methoxyaniline (o-anisidine) | 40 |
| 2 | 2-Fluoroaniline | 42 |
| 43 | 3,5-Dimethoxyaniline | 43 |
| 35 | 2-Methoxy-5-methylaniline | 43 |
| 36 | 2-Methoxy-5-nitroaniline | 43 |
| 4 | 2-(Methylmercapto)aniline | 43 |
| 118 | Cytosine | 43 |
| 11 | 3-Trifluoromethylaniline (3-aminobenzotrifluoride) | 43 |
| 1 | Aniline | 44 |
| 42 | 3,4-Dimethylaniline | 46 |
| 37 | 3,4,5-Trimethoxyaniline | 48 |
| 34 | 2,5-Dimethoxyaniline | 52 |
| 10 | 3-Fluoroaniline | 56 |
| 41 | 3,4-Dimethoxyaniline (4-aminoveratrole) | 56 |
| 31 | 4-Carboxamidoaniline (4-aminobenzamide) | 61 |
| 32 | 2,4-Difluoroaniline | 63 |
| 12 | 3-Methoxyaniline (m-anisidine) | 64 |
| 30 | 4-Methoxyaniline (p-anisidine) | 66 |

TABLE VI

| Pool # | R3 | Percent Bound |
|---|---|---|
| 27 | 4-Bromoaniline | 6 |
| 137 | Tryptamine | 7 |
| 140 | 4-Iodoaniline | 7 |
| 49 | 3,4-Dichlorobenzylamine | 8 |
| 142 | 4-Hydroxy-4-phenylpiperidine | 8 |
| 97 | 3-Fluorophenethylamine | 8 |
| 51 | Phenethylamine | 10 |
| 98 | 4-Fluorophenethylamine | 11 |
| 96 | 2-Fluorophenethylamine | 11 |
| 99 | 2,4-Dichlorophenethylamine | 12 |
| 129 | 3-Benzyloxyaniline | 12 |
| 43 | 3,5-Dimethoxyaniline | 12 |

TABLE VI-continued

| Pool # | R3 | Percent Bound |
|---|---|---|
| 53 | 2-(3-Chlorophenyl)ethylamine | 12 |
| 130 | 4-Aminopyridine | 12 |
| 135 | 2-Amino-1-phenylethanol | 13 |
| 21 | 4-(Methylmercapto)aniline | 14 |
| 76 | 4-Isopropylaniline | 14 |
| 41 | 3,4-Dimethoxyaniline (4-aminoveratrole) | 15 |
| 73 | 1-Adamantanemethylamine | 15 |
| 89 | 5-Bromo-2-fluorobenzylamine | 15 |
| 52 | 2-(2-Chlorophenyl)ethylamine | 15 |
| 66 | 1-(2-Pyridyl)piperazine | 16 |
| 40 | 4-Bromo-3-methylaniline | 16 |
| 18 | 4-Methylaniline (p-toluidine) | 16 |
| 139 | 2-Iodoaniline | 17 |
| 28 | 4-Chloroaniline | 17 |
| 42 | 3,4-Dimethylaniline | 17 |
| 132 | 5-Aminoindan | 17 |
| 94 | 4-(Dimethylamino)aniline (N,N-dimethyl-1,4-phenylenediamine) | 17 |
| 123 | 3-Phenoxyaniline | 17 |
| 37 | 3,4,5-Trimethoxyaniline | 18 |
| 128 | (±)- a-(Methylaminomethyl)benzyl alcohol | 18 |
| 100 | 3-Iodoaniline | 19 |
| 127 | 1-Naphthalenemethylamine | 19 |
| 138 | 2-Aminothiazole | 19 |
| 131 | 2-Amino-4-picoline | 19 |
| 119 | 2-Aminobenzothiazole | 20 |
| 107 | 2-Fluoro-5-methylaniline | 20 |
| 54 | 2-(4-Chlorophenyl)ethylamine | 20 |
| 13 | 3-(Methylmercapto)aniline | 20 |
| 17 | 4-Fluoroaniline | 20 |
| 93 | 4-(Dimethylamino)benzylamine | 20 |
| 134 | Tyramine | 20 |
| 145 | 3-Chloro-4-methoxyaniline (3-chloro-p-anisidine) | 20 |
| 108 | 3,5-Dimethylaniline | 20 |
| 10 | 3-Fluoroaniline | 21 |
| 19 | 4-Propylaniline | 21 |
| 12 | 3-Methoxyaniline (m-anisidine) | 21 |
| 58 | N-Benzylethanolamine | 21 |
| 111 | 2,5-Difluorobenzylamine | 21 |
| 143 | 4-Chloro-2-methoxy-5-methylaniline | 21 |
| 78 | trans-2-Phenylcyclopropylamine | 21 |
| 117 | 4-(Diethylamino)aniline (N,N-diethyl-1,4-phenylenediamine) | 22 |
| 102 | 5-Chloro-2-methoxyaniline (5-chloro-o-anisidine) | 22 |
| 141 | 2-Chloro-5-methylaniline | 22 |
| 90 | 6,7-Dimethoxy-1,2,3,4-Tetrahydroisoquinoline | 22 |
| 114 | 2,4-Dimethylaniline | 22 |
| 8 | 2-Methoxybenzylamine | 22 |
| 11 | 3-Trifluoromethylaniline (3-aminobenzotrifluoride) | 23 |
| 20 | 4-Pentylaniline | 23 |
| 106 | 2,5-Dimethylaniline | 23 |
| 55 | 4-Methoxyphenethylamine | 23 |
| 26 | 3-(1-Hydroxyethyl)aniline | 23 |
| 25 | 4-Methylbenzylamine | 23 |
| 110 | 2,4-Difluorobenzylamine | 23 |
| 101 | 3-Chloro-2-methylaniline | 23 |
| 133 | 1-Amino-5,6,7,8-tetrahydronapthalene | 23 |
| 47 | 3,4-Difluorobenzylamine | 24 |
| 109 | 2,3-Dimethoxybenzylamine | 24 |
| 112 | 2,6-Difluorobenzylamine | 24 |
| 30 | 4-Methoxyaniline (p-anisidine) | 24 |
| 69 | 2-Bromo-4-methylaniline | 24 |
| 23 | 4-Chlorobenzylamine | 25 |
| 92 | 3-Methylsulphonylaniline | 25 |
| 103 | 2-Chloro-4-fluoroaniline | 25 |
| 9 | 2-Trifluoromethylbenzylamine | 25 |
| 33 | 4-Bromo-2-methylaniline | 25 |
| 72 | 1-Methyl-3-phenylpropylamine | 25 |
| 91 | 2,4-Dimethoxybenzylamine | 25 |
| 77 | 3-Phenyl-1-propylamine | 25 |
| 71 | 3-Carboxamidoaniline (3-aminobenzamide) | 26 |
| 105 | 2,4-Dimethoxyaniline | 26 |
| 82 | 2-Bromobenzylamine | 26 |
| 83 | 3-Bromobenzylamine | 26 |
| 64 | 4-(Aminomethyl)pyridine | 26 |
| 144 | 4-Morpholinoaniline | 26 |
| 74 | 1,3,3-Trimethyl-6-azabicyclo[3.2.1]octane | 26 |
| 120 | 2-Amino-6-fluorobenzothiazole | 26 |
| 15 | 3-Methylbenzylamine | 27 |
| 50 | 3,4,5-Trimethoxybenzylamine | 27 |
| 24 | 4-Methoxybenzylamine | 27 |
| 3 | 2-Methoxyaniline (o-anisidine) | 27 |
| 39 | 3-Bromo-4-methylaniline | 27 |
| 65 | 3-(Aminomethyl)pyridine | 28 |
| 7 | 2-Chlorobenzylamine | 28 |
| 115 | 2-Fluoro-4-methylaniline | 28 |
| 44 | (±)-a-Methylbenzylamine | 28 |
| 57 | N-Benzylmethylamine | 28 |
| 63 | 1,4-Benzodioxan-6-amine | 28 |
| 38 | 3-Chloro-4-fluoroaniline | 28 |
| 121 | 2-Amino-6-methoxybenzothiazole | 28 |
| 46 | 3-Ethoxyaniline (m-phenetidine) | 28 |
| 124 | 4-Phenoxyaniline | 28 |
| 22 | 4-Fluorobenzylamine | 29 |
| 60 | 1,2,3,4-Tetrahydroisoquinoline | 29 |
| 86 | 3-Amino-2,6-dimethoxypyridine | 29 |
| 29 | 2,3-Dimethylaniline | 29 |
| 68 | Cyclohexylamine | 29 |
| 80 | 4-Bromobenzylamine | 29 |
| 34 | 2,5-Dimethoxyaniline | 30 |
| 85 | 2-Aminoindan | 30 |
| 5 | Benzylamine | 30 |
| 16 | 3-Fluorobenzylamine | 30 |
| 62 | 1-(α,α,α,-Trifluro-m-tolyl)piperazine | 30 |
| 122 | 2-(4-Aminophenyl)-6-methylbenzothiazole | 30 |
| 126 | 2-Aminofluorene | 30 |
| 125 | 1-Amino-4-bromonaphthalene | 31 |
| 4 | 2-(Methylmercapto)aniline | 32 |
| 45 | 2-Methylaniline (o-toluidine) | 32 |
| 1 | Aniline | 32 |
| 14 | 3-Trifluoromethylbenzylamine | 32 |
| 79 | 3-Nitrobenzylamine | 32 |
| 116 | (+/−) -exo-2-Aminonorbornane | 33 |
| 67 | Cycloheptylamine | 33 |
| 35 | 2-Methoxy-5-methylaniline | 33 |
| 56 | 3,4-Dimethoxyphenethylamine | 33 |
| 48 | 3,4-Dimethoxybenzylamine (Veratrylamine) | 33 |
| 87 | 4-Nitrobenzylamine | 33 |
| 113 | 5-Chloro-2-methylaniline | 33 |
| 6 | 2-Methylbenzylamine | 34 |
| 136 | 1-Adamantanamine | 34 |
| 59 | Aminodiphenylmethane | 34 |
| 95 | Pyridoxamine | 35 |
| 75 | 2-Ethoxyaniline (o-phenetidine) | 35 |
| 88 | 4-Benzyloxyaniline | 35 |
| 104 | 4-Methoxy-2-methylaniline | 35 |
| 70 | 5-Fluoro-2-methylaniline | 37 |
| 81 | (+/−)-endo-2-Aminonorbornane | 38 |
| 84 | 4-Ethoxyaniline (p-phenetidine) | 38 |
| 32 | 2,4-Difluoroaniline | 39 |
| 2 | 2-Fluoroaniline | 39 |
| 61 | 1-Phenylpiperazine | 39 |
| 31 | 4-Carboxamidoaniline (4-Aminobenzamide) | 45 |
| 36 | 2-Methoxy-5-nitroaniline | 52 |
| 118 | Cytosine | 54 |

EXAMPLE 48

Solid-phase synthesis of a library of 21,318 different isoquinoline amines

Fifty one tea-bags are prepared as in Example 43 with each containing a mixture of 418 isoquinoline amides. While still attached to the resin the isoquinoline amides are reduced to the isoquinoline amines via the procedure of Cuervo et al., Peptides 1994, Proceedings of the 23rd European Peptide Symposium, H. L. S. Maia, Editor, Escom Publishers, Leiden, pp 465–466 (1995), which is incorporated herein by reference, modified for solid-phase use as described in published WO 94/26775, which is incorporated herein by reference. One tea-bag (0.178 g resin, 120 micromoles total of mixed isoquinolines) is placed in a 50 ml KIMAX glass tube and treated under nitrogen gas with a solution of: 1M BH3 in anhydrous tetrahydrofuran (15 ml), boric acid (315 mg) and trimethyl borate (0.5 ml). After the solution is bubbling slows to a slight fizz the tube is capped tightly and heated at 65° C. for 96 hrs. After cooling the borane solution is decanted and the bag washed with methanol (1×25 ml), tetrahydrofuran (1×25 ml), and again with methanol (4×25 ml). After drying the bag is returned to a 50 ml KIMAX glass tube, submerged completely in piperidine, sealed and heated at 65° C. for 16 hrs. After cooling the piperidine is decanted off of the tea-bag and the bag is washed with DMF (2×25 ml), DCM (2×25 ml), methanol (1×25 ml), DMF (2×25 ml), DCM (2×25 ml), and again with methanol (1×25 ml). After drying the tea-bag is cleaved via the HF protocols described in Example 43, but for 9 hrs instead of 2 hrs. The remaining 50 tea-bags are treated in the same manner resulting in 51 pools of 418 isoquinoline amines, for a total library size of 21,318.

EXAMPLE 49

Solid-phase synthesis of a library of 20,482 different isoquinoline aromatic amines Forty nine tea-bags are prepared as in Example 45 with each containing a mixture of 418 isoquinoline amides. While still attached to the resin the isoquinoline amides are reduced to the isoquinoline amines and cleaved off the resin as in Example 48, resulting in 49 pools of 418 isoquinoline amines for a total library size of 20,482.

EXAMPLE 50

Solid-phase synthesis of a library of 332,860 different isoquinoline amines

One-hundred seven tea-bags were prepared as in Example 46 but on two-fold larger scale (each bag containing 200 micromoles of resin) with each containing a mixture of isoquinoline amides or acids. A subset of the amines used in Example 44 were used consisting of aniline, 2-fluoroaniline, 2-methoxyaniline, 2-chlorobenzylamine, 2-methoxybenzylamine, 2-trifluoromethylbenzylamine, 3-fluoroaniline, 3-methylaniline, 3-trifluoromethylaniline, 3-(methylmercapto)aniline, 3-trifluoromethylbenzylamine, 3-methylbenzylamine, 4-propylaniline, 4-pentylaniline, 4-(methylmercapto)aniline, 4-fluorobenzylamine, 4-methoxybenzylamine, 4-methylbenzylamine, 3-(1-hydroxyethyl)aniline, 4-chloroaniline, 2,3-dimethylaniline, 4-methoxyaniline, 2,5-dimethoxyaniline, 3-chloro-4-fluoroaniline, 3-bromo-4-methylaniline, 3,4-dimethoxyaniline, 3,4-dimethylaniline, 3,5-dimethoxyaniline, 2-methylaniline, 3,4-dimethoxybenzylamine, 3,4-dichlorobenzylamine, 2-(3-chlorophenyl)ethylamine, 4-methoxyphenethylamine, N-benzylethanolamine, aminodiphenylmethane, 1-phenylpiperazine, 1-(α,α,α-trifluoro-m-tolyl)piperazine, 1,4-benzodioxan-6-amine, 4-(aminomethyl)pyridine, 3-(aminomethyl)pyridine, 1-(2-pyridyl)piperazine, cycloheptylamine, cyclohexylamine, 5-fluoro-2-methylaniline, 3-carboxamidoaniline, 1-methyl-3-phenylpropylamine, 1-adamantanemethylamine, 1,3,3-trimethyl-6-azabicyclo[3.2.1]octane, 2-ethoxyaniline, 4-isopropylaniline, 3-phenyl-1-propylamine, trans-2-phenylcyclopropylamine, 3-nitrobenzylamine, 4-bromobenzylamine, 2-bromobenzylamine, 3-bromobenzylamine, 4-ethoxyaniline, 2-aminoindan, 3-amino-2,6-dimethoxypyridine, 4-nitrobenzylamine, 4-benzyloxyaniline, 5-bromo-2-fluorobenzylamine, 6,7-dimethoxy-1,2,3,4-tetrahydroisoquinoline, 2-adamantanamine, 2,4-dimethoxybenzylamine, 3-methylsulphonylaniline, 3-(dimethylamino)aniline, 4-(dimethylamino)aniline, pyridoxamine, 2-fluorophenethylamine, 3-fluorophenethylamine, 4-fluorophenethylamine, 2,4-dichlorophenethylamine, 3-iodoaniline, 3-chloro-2-methylaniline, 5-chloro-2-methoxyaniline(5-chloro-o-anisidine), 4-methoxy-2-methylaniline, 2,4-dimethoxyaniline, 2,5-dimethylaniline, 2-fluoro-5-methylaniline, 2,3-dimethoxybenzylamine, 2,4-difluorobenzylamine, 2,5-difluorobenzylamine, 2,6-difluorobenzylamine, 5-chloro-2-methylaniline, 2,4-dimethylaniline, 2-fluoro-4-methylaniline, 3-phenoxyaniline, 4-phenoxyaniline, 2-aminofluorene, 1-naphthalenemethylamine, 3-benzyloxyaniline, 4-aminopyridine, 2-amino-4-picoline, 5-aminoindan, 1-amino-5,6,7,8-tetrahydronaphthalene, tyramine, 2-amino-1-phenylethanol, 1-adamantanamine, 4-hydroxy-4-phenylpiperidine, 4-chloro-2-methoxy-5-methylaniline, 4-morpholinoaniline, 3-chloro-4-methoxyaniline(3-chloro-p-anisidine), carboxyl group, (±)-exo-2-aminonorbornane, (±)-endo-2-aminonorbornane, and (±)-α-methylbenzylamine. One bag was left as the carboxylic acid.

While still attached to the resin, the isoquinoline amides and acids were reduced to the isoquinoline amines and alcohols via the procedure of Cuervo et al., supra, modified for solid-phase use. One-half of the library tea-bags and one-half of the control tea-bags were placed in a 5 L glass reactor vessel under nitrogen gas containing boric acid (66.1 g, 1.07 moles) and anhydrous trimethyl borate (107 mL, 0.955 moles). A 1M solution of borane-tetrahydrofuran complex in tetrahydrofuran (3.2 L) was added slowly to the reaction. After sealing the reaction vessel was heated at 65° C. for 96 hrs. After cooling the borane solution was decanted and the bag washed with methanol (1×25 ml), tetrahydrofuran (1×25 ml), and again with methanol (4×25 ml). After drying the bags were returned to the reaction vessel, submerged completely in piperidine, sealed and heated at 65° C. for 16 hrs. After cooling the piperidine was decanted off of the tea-bags and the bags were washed with DMF (2×25 ml), DCM (2×25 ml), methanol (1×25 ml), DMF (2×25 ml), and DCM (3×25 ml).

After drying the tea-bags were cleaved as in Example 48, extracted into 45:45:10 water/acetonitrile/acetic acid and examined by HPLC coupled with mass spectrometry. The control tea-bags were cleaved in the same manner and characterized by NMR or HPLC and mass spectra.

EXAMPLE 51

Isoquinoline Library Positional Scan Format

In this example the positional scan format, as described above, is used to identify additional compounds which are significant inhibitors of the σ receptor ligand, pentazocine. Subsets of compounds were prepared as described below and screened in the σ receptor assay.

The experimental procedure was as follows. Two 0.30 μmol bags each of either FMOC or BOC protected aminoacids were prepared using MBHA resin (0.90 μmol/g) as previously described (DIC, HOBt, DMF/DCM). The amino acids used were: N-(t-butyloxycarbonyl)glycine, N-(t-butyloxycarbonyl)-3-aminopropionic acid, N-(t-butyloxycarbonyl)-5-aminopentanoic acid, N-(t-butyloxycarbonyl)-7-aminoheptanoic acid, (s)-2-N-(t-butyloxycarbonyl)-3-N-(9-fluorenylmethoxy-carbonyl)-diaminopropionoic acid, (s)-2-N-(t-butyloxycarbonyl)-6-N-(9-fluorenylmethoxy carbonyl)-diaminohexanoic acid, (s)-(t-butyloxycarbonyl)-2-methyl-3-aminopropionic acid, (r)-(t-butyloxycarbonyl)-2-methyl-3-aminopropionic acid, N-(t-butyloxycarbonyl)-2-(2-aminoethoxyethoxy)acetic acid, N-(t-butyloxycarbonyl)-trans-4-(aminomethyl) cyclohexanecarboxylic acid, N-(t-butyloxycarbonyl)-4-(aminomethyl)benzoic acid. After standard deprotection procedures (DOC: 1×15 min DCM, 1×30 min 55% TFA/DCM, 1×5 min DCM, 2×5 min IPA, 2×5 min DCM, 3×2 min 5% DIEA/DCM, 3×5 min DCM; FMOC: 1×15 min DCM, 1×5 min 20% piperidine/DMF, 1×15 min 20% piperidine/DMF, 4×5 min DMF, 4×5 min DCM) and drying under vacuum the resin-bound-aminoacids were selectively portioned into three subsets in order to prepare the library in the desired postional scan format. Control bags for library analysis were prepared using Resin-Glycine.

Subset 1 consisted of 11 bags containing 55 μmol of a mixture of all 11 the resin-aminoacids. Subset 2 contained 11 bags of 240 μmol of the 11 resin-aminoacids mixture. Subset 3 had each individual resin-aminoacid subdivided into 11×11 22 μmol bags for a total of 121 bags.

For reaction with each of the benzaldehydes and homophatlic anhydride, the bags from Subset 1,2 and 3 were divided into 11 groups. The aldehydes used were benzaldehyde, 5-nitro-2-furaldehyde, 4-nitrobenzaldehyde, 5-(hydroxymethyl)-2-furaldehyde, 4-(dimethylamino)-benzaldehyde, 3-methylbenzaldehyde, 3,5-dimethoxybenzaldehyde, 2-pyridinecarboxaldehyde, 2-naphthaldehyde, 2-furaldehyde, and 2-bromobenzaldehyde. Each group was composed of one bag each from Subset 1 and 2 and 11 bags of each individual resin-aminoacid from Subset 3 and at least one sibling bag (total 14 bags, 520 μmol). The formation of the imine intermediate was performed by placing a series of bags in 75 ml of a 0.5M solution (37.5 mmol) of the benzaldehyde. The solution contained 8.2 ml (75 mmol) of trimethylorthoformate as a dehydrating agent. The resin bags were shaken in the reaction solution for 3 to 3½ hrs at room temperature then the solution decanted and bags quickly washed 1× with 30 ml anhydrous DMF and 1×30 ml anhydrous $CHCl_3$. Seventy-five ml of a stock solution of 0.5M homophatlic anhydride in $CHC_3$ (66.88 g in 825 ml plus 2.6 ml triethylamine catalyst) was added to each of the reaction vessels which were shaken at room temperature for 18 hrs. The reaction solution was decanted and the resin-bags washed 3×30 ml DMF, 3×30 ml DCM, 1×30 ml MeOH and the bags dried 3–4 hrs under vacuum.

The Subsets now contained the intermediate tetrahydroisoquinoline acids with a single benzaldehyde derived fragment in combination with either a mixture of all the 11 aminoacid derived fragment (Subset 1 and 2) or a single aminoacid derived fragment (Subset 3). The Subsets where reapportioned according to the following scheme. Subset 1: all the resin-bound intermediates from original Subset 1, mixed into a single portion by combining the dry solids into a large (5 cm×5 cm) resin bag and mixing for 30 min in DCM. After a MeOH wash and vacuum drying the mixed resin was divided into 12 equal portions to provide 50 μmol scale bags. Subset 1 now represented mixtures from both the aminoacid and benzaldehyde building blocks. Subset 2: each of the 240 μmol bags from original Subset 2 was divided into 12 equal portions of 20 μmol to create bags which were mixed aminoacid fragments but contained sets of individual benzaldehyde fragments. Subset 3: for every individual resin-aminoacid set from original Subset 3 all the different benzaldehyde derived fragments were pooled into separate bags, mixed by treatment with DCM, then MeOH and dried under vacuum. These 11 new mixtures were subdivided into 12 equal portions to generate 20 μmol bags that contained a single aminoacid fragment and a mixture of the 11 benzaldehyde fragments.

The bags were once again separated into 11 groups which contained 1 bag from Subset 1, 11 bags from Subset 2, and 11 bags from Subset 3, and a sibling bag prepared from resin-glycine-3,5-dimethoxybenzaldehyde. The groups of bags were treated with 30 ml of a 0.3M DMF stock solution of (O-(7-azabenzotriazol-1-yl)-1,1,3,3-tetramethyluronium hexafluorophosphate (HATU: 79.84 g in 700 ml anhydrous DMF) by shaking for 30 min. The HATU solution was decanted and the bags shaken for 2 hrs in 40 ml of a 1M DMF solution of an amine (75 mmol in 75 ml). The amines used were 1-(2-aminoethyl)pyrrolidine, 1-adamantanemethylamine, 1-(2-hydroxyethyl)piperazine, piperidine, (aminomethyl)cyclohexane, 4-aminomorpholine, amylamine, aniline, cyclopentylamine, ethanolamine, and tryptamine. The amine solution was decanted and the bags washed 2×30 ml DMF. The HATU treatments was repeated with an additional 30 ml of a 0.3M DMF stock solution and 1 hr on the shaker then pouring off the solutions. Thirty-five ml of 1M amine/DMFsolution was added and the reactions allowed to shake for 24 hrs. The solutions were decanted and the bags washed with 3×30 ml DMF, 3×30 ml DCM and 1×30 ml MeOH. After drying under vacuum the resin was distributed according to the following scheme. Subset 1: The bags from Subset 1 contained mixtures from both the aminoacid and benzaldehyde building blocks but had a single amine fragment. These 50 μmol bags were used directly in the HF cleavage step. Subset 2: The 11 amine bags of the same resin-benzaldehyde-mixed amino acid fragments were combined into a bag in order to create a mixture of all the amines. After shaking for 30 min in DCM, then 30 min in MeOH, the resin was dried 3–4 hrs under vacuum. A 50 μmol sample bag was prepared from each of the fixed benzaldehyde mixtures for HF cleavage. Subset 3: The 11 amine bags containing the same resin-aminoacid-mixed benzaldehyde were mixed with the DCM/MeOH/vacuum drying procedure. Fifty μmol sample bags were created from each of the mixtures with the fixed amino acid position.

Standard liquid HF/anisole MBHA-resin cleavage was carried out on the 33 bags and the product mixtures extracted 3×5 ml of 50% acetonitrile/water. The solvent was removed by lypholization (2×) to yield 12 to 26 mg of solids. Each sample represented a 50 μmol mixture of 242 compounds with one of the variable building blocks (aminoacid, benzaldehyde, amine) as a defined compentent of the library thus producing the postional scan format.

The results of the positional scan approach and the σ receptor screen evidenced the most active compound similar to that in Example 44, wherein $R^1$ is 1,6-hexyl, $R^2$ is 5-(4'-methoxybenzyl)-furan-2-yl, $R^3$ through $R^6$ is, independently, a hydrogen atom, Y is C(O)NH$_2$, and the one distinction being at the X position, (aminomethyl)cyclohexyl in place of 1-aminomethyladamantanyl. The compound having (aminomethyl)cyclohexyl at the X position was seen to have virtually equal activity.

Although the invention has been described with reference to the examples provided above, it should be understood that various modifications can be made by those skilled in the art without departing from the invention. Accordingly, the invention is set out in the following claims.

We claim:

1. A single isoquinoline compound of the formula:

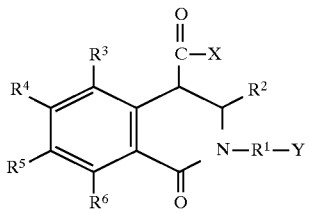

FORMULA I wherein:

R$^1$ is selected from the group consisting of C$_1$ to C$_6$ alkyl, C$_1$ to C$_6$ substituted alkyl, C$_2$ to C$_7$ alkenyl, C$_2$ to C$_7$ substituted alkenyl, C$_2$ to C$_7$ alkynyl, C$_2$ to C$_7$ substituted alkynyl, C$_3$ to C$_7$ cycloalkyl, C$_3$ to C$_7$ substituted cycloalkyl, C$_5$ to C$_7$ cycloalkenyl, C$_5$ to C$_7$ substituted cycloalkenyl, phenyl, substituted phenyl, substituted naphthyl, C$_7$ to C$_{12}$ phenylalkyl, C$_7$ to C$_{12}$ substituted phenylalkyl and a group of the formula:

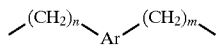

wherein:

n and m are independently selected from a number 0 to 6; and Ar is an aryl group selected from the group consisting of phenyl, substituted phenyl, heteroaryl and substituted heteroaryl;

R$^2$ is selected from the group consisting of hydrogen atom, C$_1$ to C$_6$ alkyl, C$_1$ to C$_6$ substituted alkyl, C$_2$ to C$_7$ alkenyl, C$_2$ to C$_7$ substituted alkenyl, C$_2$ to C$_7$ alkynyl, C$_2$ to C$_7$ substituted alkynyl, phenyl, substituted phenyl, naphthyl, substituted naphthyl, C$_3$ to C$_7$ cycloalkyl, C$_3$ to C$_7$ substituted cycloalkyl, C$_5$ to C$_7$ cylcoalkenyl, C$_5$ to C$_7$ substituted cycloalkenyl, C$_7$ to C$_{12}$ phenylalkyl, C$_7$ to C$_{12}$ substituted phenylalkyl and a heterocyclic ring;

R$^3$, R$^4$, R$^5$ and R$^6$ are independently selected from the group consisting of a hydrogen atom, halo, hydroxy, protected hydroxy, cyano, nitro, carboxylic acid, C$_1$ to C$_6$ alkyl, C$_2$ to C$_7$ alkenyl, C$_2$ to C$_7$ alkynyl, C$_1$ to C$_6$ substituted alkyl, C$_2$ to C$_7$ substituted alkenyl, C$_2$ to C$_7$ substituted alkynyl, C$_1$ to C$_7$ alkoxy, C$_1$ to C$_7$ acyloxy, C$_1$ to C$_7$ acyl, C$_3$ to C$_7$ cycloalkyl, C$_3$ to C$_7$ substituted cycloalkyl, C$_5$ to C$_7$ cycloalkenyl, C$_5$ to C$_7$ substituted cycloalkenyl, C$_3$ to C$_7$ substituted cycloalkenyl, a heterocyclic ring, C$_7$ to C$_{12}$ phenylalkyl, C$_7$ to C$_{12}$ substituted phenylalkyl, phenyl, substituted phenyl, naphthyl, substituted naphthyl, cyclic C$_2$ to C$_7$ alkylene, substituted cyclic C$_2$ to C$_7$ alkylene, cyclic C$_2$ to C$_7$ heteroalkylene, substituted cyclic C$_2$ to C$_7$ heteroalkylene, carboxy, protected carboxy, hydroxymethyl, protected hydroxymethyl, amino, protected amino, (monosubstituted)amino, protected (monosubstituted) amino, (disubstituted) amino, carboxamide, protected carboxamide, C$_1$ to C$_4$ alkylthio, C$_1$ to C$_4$ alkylsulfonyl, C$_1$ to C$_4$ alkylsulfoxide, phenylthio, substituted phenylthio, phenylsulfoxide, substituted phenylsulfoxide, phenylsulfonyl and substituted phenylsulfonyl;

X is selected from the group consisting of hydroxy, protected carboxy, amino, protected amino, (monosubstituted)amino, (disubstituted)amino, an amino acid, aniline, substituted aniline and an amino-substituted heterocyclic ring;

Y is selected from the group consisting of CO$_2$H, SH, NHR$^7$ and C(O)NHR$^7$, wherein R$^7$ is selected from the groups consisting of a hydrogen atom, C$_1$ to C$_6$ alkyl and C$_1$ to C$_6$ substituted alkyl; or a salt of the isoquinoline compound.

2. The single isoquinoline compound of claim 1, wherein:

R$^1$ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2 ethyl),

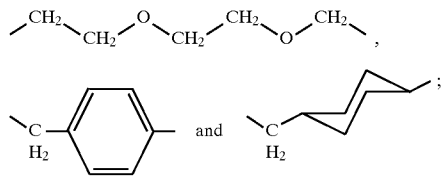

R$^2$ is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophen-yl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophen-yl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophenyl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

R$^3$, R$^4$, R$^5$, R$^6$ are independently a hydrogen atom;

X is selected from the group consisting of aminocyclopropyl, aminoisopropyl, 3-aminopropyl, aminoethanolyl, (aminomethyl)cyclopropyl, pyrrolidyl, aminodiethyl, amino-2-methoxyethyl, aminocyclopentyl, piperidinyl, 1-(pyrrolidin-3-ol), aminoamyl, amino-2-(N,N-dimethyl)ethyl, azetidinyl, 2-aminofurfuryl, aminodiallyl, 2-aminothiazolyl, 1-aminopiperidinyl, 4-methylpiperazinyl, 4-aminomorpholinyl, aminodiethanol, 2-(aminomethyl)pyridinyl, histaminyl, 1-(2-aminoethyl)pyrrolidinyl, 1-amino-4-methylpiperazinyl, tris(hydroxymethyl)aminomethyl, 1-aminopyrrolidinyl, 1-(3-aminopropyl)imidazolyl, 1-(2-hydroxyethyl)piperazinyl, (+)-3-hydroxy piperidine, (s)-1-amino-2-(methoxymethyl) pyrrolidine, 1-amino-4-(2-hydroxyethyl)piperazinyl, trans-aminocyclohexan-2-olyl, tryptaminyl, 1-aminomethyladamantanyl, amino-2-(trimethylammonium)ethyl, α-N-glycinyl, α-N- lysinyl, α-N-aspartyl, α-N-tyrosinyl, α-N-serinyl, (+)-3-aminopropyl-1,2-diol, (−)-3-amino-propyl-1,2-diol, (+)-aminotetrahydrofurfuryl, (−)-aminotetrahydrofurfuryl, (+)-exo-2-aminonorbornanyl, (−)-exo-2-aminonorbornanyl, cis-decahydroquinolinyl, trans-decahydroquinolinyl, (+)-3-aminoquinuclidinyl and (−)-3-aminoquinuclidinyl; and Y is C(O)NH$_2$.

3. The isoquinoline compound of claim 2, wherein X is 1-aminomethyladamantanyl.

4. A single isoquinoline compound of the formula:

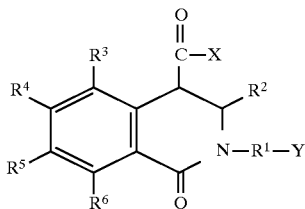

FORMULA I wherein:

R$^1$ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2 ethyl),

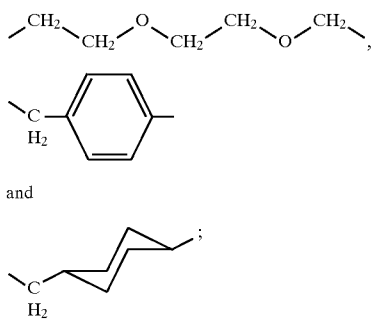

R$^2$ is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophen-yl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophen-yl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophen-yl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

R$^3$, R$^4$, R$^5$, R$^6$ are independently a hydrogen atom;

X is (aminomethyl)cyclohexyl; and

Y is C(O)NH$_2$.

5. The isoquinoline compound of claims 3 or 4, wherein R$^2$ is 5-(4'-methoxybenzyl)-furan-2-yl.

6. The isoquinoline compound of claim 5, wherein R$^1$ is 1,6-hexyl.

7. The isoquinoline compound of claim 1, wherein:

R$^1$ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2-ethyl),

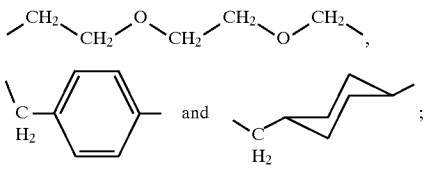

R$^2$ is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophen-yl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophen-yl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophen-yl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

R$^3$, R$^4$, R$^5$, R$^6$ are independently a hydrogen atom;

X is selected from the group consisting of anilinyl, 2-fluoroanilinyl, 3-fluoroanilinyl, 4-fluoroanilinyl, 2-chloroanilinyl, 3-chloroanilinyl, 4-chloroanilinyl, 2-bromoanilinyl, 3-bromoanilinyl, 4-bromoanilinyl, 2-methoxyanilinyl, 3-methoxyanilinyl, 4-methoxyanilinyl, 2-hydroxyanilinyl, 3-hydroxyanilinyl, 4-hydroxyanilinyl, 2-carboethoxyanilinyl, 3-carboethoxyanilinyl, 4-carboethoxyanilinyl, 2-trifluoromethylanilinyl, 3-trifluoromethylanilinyl, 4-trifluoromethylanilinyl, 2-dimethylaminoanilinyl, 3-dimethylaminoanilinyl, 4-dimethylaminoanilinyl, 2-phenoxyanilinyl, 3-phenoxyanilinyl, 4-phenoxyanilinyl, 3,4-methylenedioxyanilinyl, 2,3-methylenedioxyanilinyl, 2,3-difluoroanilinyl, 2,3-dibromoanilinyl, 3,4-dibromoanilinyl, 2,3-dimethoxyanilinyl, 3,4-dimethoxyanilinyl, 1-amino-5,6,7,8-tetrahydronaphthyl, 2-hydroxy-3-amino 5,6,7,8-tetrahydronaphthyl, 2-aminonaphthyl, 1-amino-4-chloronaphthyl, 1-amino-4-bromonaphthyl, 5-amino-1-hydroxynaphthyl, 1-amino-2-hydroxynaphthyl, 5-aminoindanyl, 1-aminofluorenyl, 2-aminofluorenyl and N-methylanilinyl; and Y is C(O)NH$_2$.

8. A single isoquinoline compound or a library of an approximately equimolar mixture of two or more compounds of the formula:

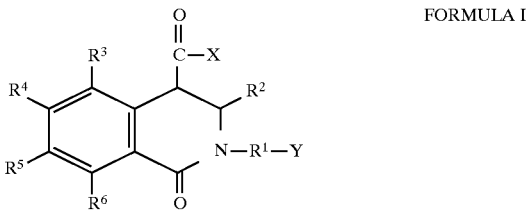

FORMULA I wherein:

R$^1$ is selected from the group consisting of methylene, 1,2-ethyl, 1,3-propyl, 1,4-butyl, 1,5-pentyl, 1,6-hexyl, (S)-1-amino-1,2-ethyl, (S)-1-amino-1,5-pentyl, (R)-1-methyl-1,2-ethyl, (S)-1-methyl-1,2-ethyl,

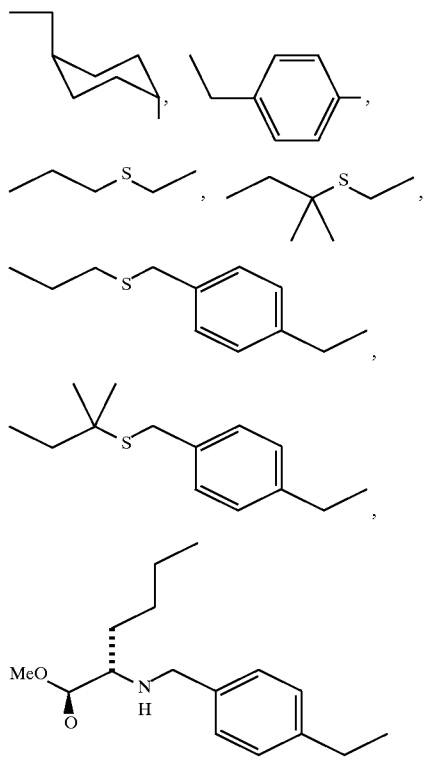

R² is selected from the group consisting of phenyl, 2-bromophenyl, 2-cyanophenyl, 2-fluorophenyl, 2-hydroxyphenyl, 2-methoxyphenyl, 3-bromophenyl, 3-carboxyphenyl, 3-cyanophenyl, 3-fluorophenyl, 3-hydroxyphenyl, 3-methoxyphenyl, 3-methylphenyl, 3-nitrophenyl, 3-(trifluoromethyl)phenyl, 4-acetamidophenyl, 4-bromophenyl, 4-carboxyphenyl, 4-cyanophenyl, 4-(3-dimethylaminopropoxy)phenyl, 4-fluorophenyl, 4-(dimethylamino)phenyl, 4-hydroxyphenyl, 4-isopropylphenyl, 4-methoxyphenyl, 4-methylphenyl, 4-(methylcarboxylate)phenyl, 4-methylsulphonylphenyl, 4-(methylthio)phenyl, 4-nitrophenyl, 4-propoxyphenyl, 4, (trifluoromethyl)phenyl, 3,5-bis(trifluoromethyl)phenyl, 3,5-dimethoxyphenyl, 3,5-dihydroxyphenyl, 3,5-dichlorophenyl, 2,3-difluorophenyl, 2,4-dichlorophenyl, 2-chloro-5-nitrophenyl, 2-chloro-6-fluorophenyl, 2,6-difluorophenyl, 3-bromo-4-fluorophenyl, 3,4-dihydroxyphenyl, 3,4-dichlorophenyl, 3,4-difluorophenyl, 3-fluoro-4-methoxyphenyl, 3-nitro-4-chlorophenyl, 3-hydroxy-4-methoxyphenyl, 3-hydroxy-4-nitrophenyl, 4-methoxy-3-(sulfonyl)phenyl, 3-methyl-4-methoxyphenyl, 2,3,4-trifluorophenyl, 2,3,5-trichlorophenyl, 3,5-dimethyl-4-hydroxyphenyl, 3-methoxy-4-hydroxy-5-bromophenyl, 3-methoxy-4-hydroxy-5-nitrophenyl, 1,4-benzodioxan-6-yl, 2,3-(methylenedioxy)phenyl, 3,4-(methylenedioxy)phenyl, 3,4-(methylenedioxy)-6-nitrophenyl, 8-hydroxyjulolidin-9-yl, 3-(3,4-dichlorophenoxy)phenyl, 3-(4-methoxyphenoxy)phenyl, 3-phenoxyphenyl, 4-phenoxyphenyl, 4-biphenyl, 1-naphthyl, 2-naphthyl, 4-methoxy-1-naphthyl, 2-quinolinyl, 3-quinolinyl, 4-quinolinyl, 8-hydroxyquinolin-2-yl, 9-ethyl-3-carbazolyl, 2-thiophen-yl, 3-thiophen-yl, 5-methyl-2-thiophen-yl, 2-furyl, 3-furyl, 5-methyl-2-furyl, 2-pyridinyl, 3-pyridinyl, 4-pyridinyl, 6-methyl-2-pyridinyl, pyrrole-2-yl, 1-methyl-2-pyrrolyl, 2-imidazolyl, 2-thiazolyl, 5-(4'-methoxybenzyl)-2-furyl, and 5-nitro-2-furyl;

R³, R⁴, R⁵, R⁶ are independently a hydrogen atom;

X is selected from the group consisting of pyridoxamino, 4-(dimethylamino)benzylamino, 2-chloro-4-fluoroanilino, 3-pyridylmethylamino, 4-(dimethylamino)anilino, 1-adamantanemethylamino, 4-isopropylanilino, 3,4-dichlorobenzylamino, N-benzylethanolamino, 1-(α,α,α-trifluoro-m-tolyl)piperazino, 4-nitrobenzylamino, 5-indanylamino, cyclohexylamino, 1-(2-pyridyl)piperazino, 4-methoxyphenethylamino, 1-naphthalenemethylamino, 2,4-dimethoxybenzylamino, (±)-exo-2-norbornaneamino, 2-(2-chlorophenyl)ethylamino, 2-(4-methoxyphenyl)-2-phenylethylamino, 1,4-benzodioxan-6-amino, 5-bromo-2-fluorobenzylamino, 4-pyridylmethylamino, 1-phenylpiperazino, 2-fluoreneamino, 3,4-dimethoxybenzylamino, 2-(4-chlorophenyl)ethylamino, diphenylmethylamino, phenethylamino, N-benzylmethylamino, 4-iodoanilino, 3-nitrobenzylamino, (±)-endo-2-norbornaneamino, 2-(3-chlorophenyl)ethylamino, 3-phenyl-1-propylamino, 3,5-dimethylanilino, 1,2,3,4-tetrahydroisoquinolino, 1,3,3-trimethyl-6-azabicyclo[3.2.1]octyl, 2-chloro-5-methylanilino, 3-chloro-4-methoxyanilino, 4-(4-methoxyphenyl)-4-phenylpiperidino, 5-fluoro-2-methylanilino, 4-phenoxyanilino, tryptamino, cycloheptylamino, 2,4-difluorobenzylamino, 2-fluoro-5-methylanilino, 3,4-difluorobenzylamino, 1-methyl-3-phenylpropylamino, 2,4-dichlorophenethylamino, 2-indanamino, 3,4,5-trimethoxybenzylamino, 2-bromobenzylamino, 2-bromo-4-methylanilino, trans-2-phenylcyclopropylamino, 3-amino-2,6-dimethoxypyridino, 5-chloro-2-methoxyanilino, 2-iodoanilino, 2,3-dimethoxybenzylamino, 2,6-difluorobenzylamino, 2,4-dimethoxyanilino, 4-chloro-2-methoxy-5-methylanilino, 1-amino-4-bromonaphthalene, 3-trifluoromethylbenzylamino, 3-chloro-2-methylanilino, 3-carboxamidoanilino, 2-fluorophenethylamino, 3-bromobenzylamino, 3-iodoanilino, 3-phenoxyanilino, 3,4-dimethoxyphenethylamino, 4-morpholinoanilino, 2-ethoxyanilino, tyramino, 2-trifluoromethylbenzylamino, 4-bromobenzylamino, 4-pentylanilino, 6,7-dimethoxy-1,2,3,4-tetrahydroisoquinolino, 3-(1-(4-methoxyphenyl)ethyl)anilino, 1-adamantanamino, 2-thiazoleamino, 3-hydroxyanilino, 2-(4-aminophenyl)-6-methylbenzothiazolo, 3-methylsulphonylanilino, 4-propylanilino, 2-fluoro-4-methylanilino, 4-chlorobenzylamino, 3-fluorobenzylamino, 4-bromo-3-methylanilino, (±)-α-(methylaminomethyl)benzyl alcohol, 5,6,7,8-tetrahydronaphthalene-1-amino, 3-methylbenzylamino, 4-(methylmercapto)anilino, 5-chloro-2-methylanilino, 4-(diethylamino)anilino, (±)-α-methylbenzylamino, 2-chlorobenzylamino, 4-fluorobenzylamino, 2-methoxybenzylamino, 2-methylbenzylamino, 3-bromo-4-methylanilino, 4-fluorophenethylamino, 4-ethoxyanilino, 2,5-difluorobenzylamino, 2,3-dimethylanilino, benzylamino, 4-aminopyridino, 4-chloroanilino, 3-fluorophenethylamino, 4-bromoanilino, 4-hydroxyanilino, 4-bromo-2-methylanilino, 2-benzothiazolamino, 6-methoxybenzothiazol-2-amino, 4-methylbenzylamino, 2,4-dimethylanilino, 6-fluorobenzothiazol-2-amino, 3-(methylmercapto) anilino, 2-methylanilino, 4-picolin-2-amino, 3-chloro-4-fluoroanilino, 4-fluoroanilino, 4-methoxybenzylamino, 3-ethoxyanilino, 4-methoxy-2-methylanilino, 4-methylanilino, 2,5-dimethylanilino, 2-methoxyanilino, 2-fluoroanilino, 3,5-dimethoxyanilino, 2-methoxy-5-methylanilino, 2-methoxy-5-nitroanilino, 2-(methylmercapto)anilino, cytosino, 3-trifluoromethylanilino, anilino, 3,4-dimethylanilino, 3,4,5-trimethoxyanilino, 2,5-dimethoxyanilino, 3-fluoroanilino, 3,4-dimethoxyanilino, 4-carboxamidoanilino, 2,4-difluoroanilino, 3-methoxyanilino, and 4-methoxyanilino; and Y is C (O) NH$_2$.

9. A single isoquinoline compound or a library of an approximately equimolar mixture of two or more compounds of the formula:

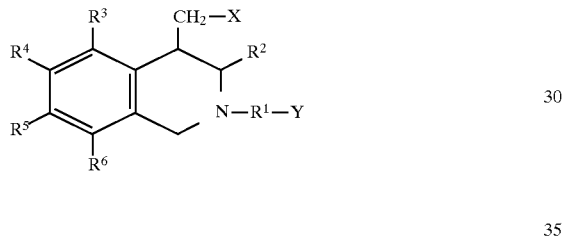

wherein:

R$^1$ is selected from the group consisting of methylene, 1,2-ethyl, 1,3-propyl, 1,4-butyl, 1,5-pentyl, 1,6-hexyl, (S)-1-amino-1,2-ethyl, (S)-1-amino-1,5-pentyl, (R)-1-methyl-1,2-ethyl, (S)-1-methyl-1,2-ethyl,

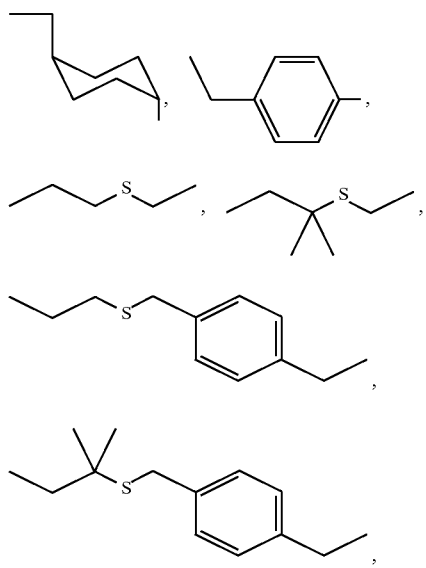

-continued

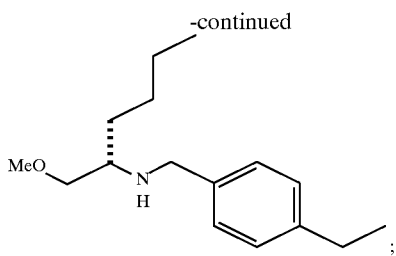

R$^2$ is selected from the group consisting of phenyl, 2-bromophenyl, 2-cyanophenyl, 2-fluorophenyl, 2-hydroxyphenyl, 2-methoxyphenyl, 3-bromophenyl, 3-(4-methoxybenzyl)phenyl, 3-cyanophenyl, 3-fluorophenyl, 3-hydroxyphenyl, 3-methoxyphenyl, 3-methylphenyl, 3-nitrophenyl, 3-(trifluoromethyl) phenyl, 4-(N-ethylamino)anilino, 4-bromophenyl, 4-(4-methoxybenzyl)phenyl, 4-cyanophenyl, 4-(3-dimethylaminopropoxy)phenyl, 4-fluorophenyl, 4-(dimethylamino)phenyl, 4-hydroxyphenyl, 4-isopropylphenyl, 4-methoxyphenyl, 4-methylphenyl, 4-methylsulphonylphenyl, 4-(methylthio)phenyl, 4-nitrophenyl, 4-propoxyphenyl, 4-(trifluoromethyl) phenyl, 3,5-bis(trifluoromethyl)phenyl, 3,5-dimethoxyphenyl, 3,5-dihydroxyphenyl, 3,5-dichlorophenyl, 2,3-difluorophenyl, 2,4-dichlorophenyl, 2-chloro-5-nitrophenyl, 2-chloro-6-fluorophenyl, 2,6-difluorophenyl, 3-bromo-4-fluorophenyl, 3,4-dihydroxyphenyl, 3,4-dichlorophenyl, 3,4-difluorophenyl, 3-fluoro-4-methoxyphenyl, 3-nitro-4-chlorophenyl, 3-hydroxy-4-methoxyphenyl, 3-hydroxy-4-nitrophenyl, 4-methoxy-3-(sulfonyl)phenyl, 3-methyl-4-methoxyphenyl, 2,3,4-trifluorophenyl, 2,3,5-trichlorophenyl, 3,5-dimethyl-4-hydroxyphenyl, 3-methoxy-4-hydroxy-5-bromophenyl, 3-methoxy-4-hydroxy-5-nitrophenyl, 1,4-benzodioxan-6-yl, 2,3-(methylenedioxy)phenyl, 3,4-(methylenedioxy)phenyl, 3,4-(methylenedioxy)-6-nitrophenyl, 8-hydroxyjulolidin-9-yl, 3-(3,4-dichlorophenoxy)phenyl, 3-(4-methoxyphenoxy) phenyl, 3-phenoxyphenyl, 4-phenoxyphenyl, 4-biphenyl, 1-naphthyl, 2-naphthyl, 4-methoxy-1-naphthyl, 2-quinolinyl, 3-quinolinyl, 4-quinolinyl, 8-hydroxyquinolin-2-yl, 9-ethyl-3-carbazolyl, 2-thiophen-yl, 3-thiophen-yl, 5-methyl-2-thiophen-yl, 2-furyl, 3-furyl, 5-methyl-2-furyl, 2-pyridinyl, 3-pyridinyl, 4-pyridinyl, 6-methyl-2-pyridinyl, pyrrole-2-yl, 1-methyl-2-pyrrolyl, 2-imidazolyl, 2-thiazolyl, 5-(4'-methoxybenzyl)-2-furyl, and 5-nitro-2-furyl;

R$^3$, R$^4$, R$^5$, R$^6$ are independently a hydrogen atom;

X is selected from the group consisting of anilino, 2-fluoroanilino, 2-methoxyanilino, 2-chlorobenzylamino, 2-methoxybenzylamino, 2-trifluoromethylbenzylamino, 3-fluoroanilino, 3-methylanilino, 3-trifluoromethylanilino, 3-(methylmercapto)anilino, 3-trifluoromethylbenzylamino, 3-methylbenzylamino, 4-propylanilino, 4-pentylanilino, 4-(methylmercapto) anilino, 4-fluorobenzylamino, 4-methoxybenzylamino, 4-methylbenzylamino, 3-(1-(4-methoxyphenyl)ethyl) anilino, 4-chloroanilino, 2,3-dimethylanilino, 4-methoxyanilino, 2,5-dimethoxyanilino, 3-chloro-4-fluoroanilino, 3-bromo-4-methylanilino, 3,4-dimethoxyanilino, 3,4-dimethylanilino, 3,5-dimethoxyanilino, 2-methylanilino, 3,4- dimethoxybenzylamino, 3,4-dichlorobenzylamino, 2-(3-chlorophenyl)ethylamino, 4-methoxyphenethylamino, N-benzylethanolamino, aminodiphenylmethane, 1-phenylpiperazino, 1-(α,α,α-trifluoro-m-tolyl)piperazino, 1,4-benzodioxan-6-amino, 4-(aminomethyl)pyridino, 3-(aminomethyl)pyridino, 1-(2-pyridyl)piperazino, cycloheptylamino, cyclohexylamino, 5-fluoro-2-methylanilino, 3-(aminomethyl)anilino, 1-methyl-3-phenylpropylamino, 1-adamantanemethylamino, 1,3,3-trimethyl-6-azabicyclo[3.2.1]octyl, 2-ethoxyanilino, 4-isopropylanilino, 3-phenyl-1-propylamino, trans-2-phenylcyclopropylamino, 3-nitrobenzylamino, 4-bromobenzylamino, 2-bromobenzylamino, 3-bromobenzylamino, 4-ethoxyanilino, 2-indanamino, 2,6-dimethoxypyridine-3-amino, 4-nitrobenzylamino, 4-hydroxyanilino, 5-bromo-2-fluorobenzylamino, 6,7-dimethoxy-1,2,3,4-tetrahydroisoquinolino, 2-adamantanamino, 2,4-dimethoxybenzylamino, 3-methylsulphonylanilino, 3-(dimethylamino)anilino, 4-(dimethylamino)anilino, pyridoxamino, 2-fluorophenethylamino, 3-fluorophenethylamino, 4-fluorophenethylamino, 2,4, dichlorophenethylamino, 3-iodoanilino, 3-chloro-2-methylanilino, 5-chloro-2-methoxyanilino, 4-methoxy-2-methylanilino, 2,4, dimethoxyanilino, 2,5-dimethylanilino, 2-fluoro-5-methylanilino, 2,3-dimethoxybenzylamino, 2,4-difluorobenzylamino, 2,5-difluorobenzylamino, 2,6-difluorobenzylamino, 5-chloro-2-methylanilino, 2,4-dimethylanilino, 2-fluoro-4-methylanilino, 3-phenoxyanilino, 4-phenoxyanilino, 2-fluorenamino, 1-naphthalenemethylamino, 3-hydroxyanilino, 4-aminopyridino, 4-picolin-2-amino, 5-indanamino 1-amino-5,6,7,8-tetrahydronaphthalene, tyramino, 1-(4-methoxyphenyl-1-phenylethyl-2-amino, 1-adamantanamino, 4-(4-methoxyphenyl)-4-phenylpiperidino, 4-chloro-2-methoxy-5-methylanilino, 4-morpholinoanilino, 3-chloro-4-methoxyanilino, hydroxyl, (±)-exo-2-norbornanamino, (±)-endo-2-norbornanamino, and (±)-α-methylbenzylamino; and Y is selected from the group consisting of CH₂OH, SH, NHR⁷ and CH₂NHR⁷, wherein R⁷ is selected from the groups consisting of a hydrogen atom, C₁ to C₆ alkyl and C₁ to C₆ substituted alkyl.

10. An isoquinoline library of an approximately equimolar mixture of two or more compounds of the formula:

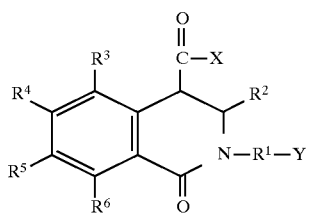

FORMULA I wherein:

R¹ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2 ethyl),

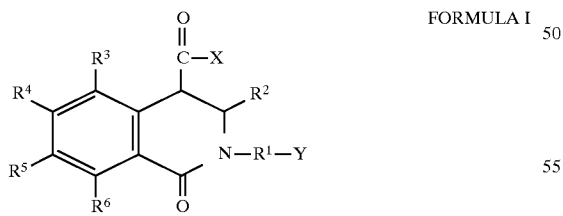

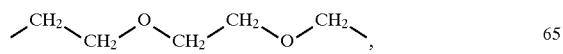

R² is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophen-yl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophen-yl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophenyl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

R³, R⁴, R⁵, R⁶ are independently a hydrogen atom;

X is 1-aminomethyladamantanyl; and

Y is C(O)NH₂.

11. An isoquinoline library of an approximately equimolar mixture of two or more compounds of the formula:

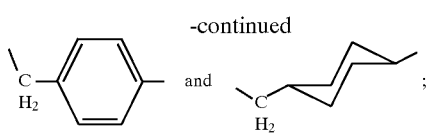

FORMULA I wherein:

R¹ is selected from the group consisting of methylene, 1,2-ethyl, 1,4-butyl, 1,6-hexyl, (s)-1-(amino)-1,2-ethyl, (s)-1-(amino)-1,5-pentyl, (r)-(1-methyl)-1,2-ethyl, (s)-(1-(methyl)-1,2 ethyl),

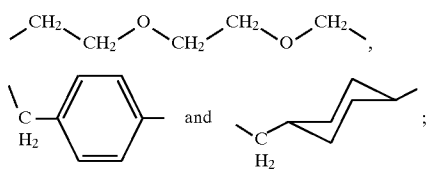

R² is selected from the group consisting of 1,4-benzodioxan-6-yl, 1-methylindole-3-yl, 2,3-difluorophenyl, 2-bromophenyl, 2-chloro-5-nitrophenyl, 2-furyl, 2-imidazolyl, 2-naphthyl, 2-pyridinyl, 2-thiophen-yl, 3,4-dichlorophenyl, 3,5-bis(trifluoromethyl)phenyl, 3,5-dihydroxyphenyl, 3,5-dimethoxyphenyl, 3,5-dimethyl-4-hydroxyphenyl, 3-(4-methoxyphenoxy)phenyl, 3-furyl, 3-hydroxyphenyl, 3-methyl-4-methoxyphenyl, 3-methylphenyl, 3-nitrophenyl, 3-pyridinyl, 3-thiophen-yl, 4-(3-dimethylaminopropoxy)phenyl, 4-(dimethylamino)phenyl, 4-(methylthio)phenyl, 4-(trifluoromethyl)phenyl, 4-biphenyl, 4-bromo-2-thiophenyl, 4-cyanophenyl, 4-methoxy-1-naphthyl, 4-nitrophenyl, 4-pyridinyl, 5-(4'-methoxybenzyl)-furan-2-yl, 5-bromo-4-hydroxy-3-methoxyphenyl, 5-nitro-2-furyl, 6-methyl-2-pyridinyl and phenyl;

$R^3$, $R^4$, $R^5$, $R^6$ are independently a hydrogen atom;

X is (aminomethyl)cyclohexyl; and

Y is $C(O)NH_2$.

12. The library of claims 10 or 11 wherein $R^2$ is 5-(4'-methoxybenzyl)-furan-2-yl.

* * * * *